US012286452B2

(12) United States Patent
Altenberg et al.

(10) Patent No.: US 12,286,452 B2
(45) **Date of Patent: *Apr. 29, 2025**

(54) AMPHIPHILIC AMINOGLYCOSIDE CONNEXIN HEMICHANNEL INHIBITORS

(71) Applicants: Texas Tech University System, Lubbock, TX (US); Utah University, Logan, UT (US)

(72) Inventors: Guillermo A. Altenberg, Lubbock, TX (US); Cheng-Wei Tom Chang, Logan, UT (US)

(73) Assignees: TEXAS TECH UNIVERSITY SYSTEM, Lubbock, TX (US); UTAH STATE UNIVERSITY, Logan, UT (US)

( * ) Notice: Subject to any disclaimer, the term of this patent is extended or adjusted under 35 U.S.C. 154(b) by 644 days.

This patent is subject to a terminal disclaimer.

(21) Appl. No.: 17/119,301

(22) Filed: Dec. 11, 2020

(65) Prior Publication Data

US 2021/0163521 A1 Jun. 3, 2021

Related U.S. Application Data

(63) Continuation-in-part of application No. PCT/US2019/036714, filed on Jun. 12, 2019.

(60) Provisional application No. 62/683,673, filed on Jun. 12, 2018.

(51) Int. Cl.
*C07H 15/234* (2006.01)

(52) U.S. Cl.
CPC .................................. *C07H 15/234* (2013.01)

(58) Field of Classification Search
None
See application file for complete search history.

(56) References Cited

U.S. PATENT DOCUMENTS

| | | | | |
|---|---|---|---|---|
| 9,485,983 | B2 | 11/2016 | Leybaert | |
| 2012/0316125 | A1* | 12/2012 | Chang | C07H 11/00 536/13.7 |
| 2014/0256666 | A1* | 9/2014 | Sinha | A61P 27/02 560/102 |
| 2016/0060285 | A1* | 3/2016 | Chang | A61K 31/415 536/13.7 |
| 2017/0049761 | A1 | 2/2017 | Kielian | |

OTHER PUBLICATIONS

Subedi, Med. Chem. Commun. 2018, 9, 909-919. (Year: 2018).*
Matsuda, The Journal of Antibiotics, vol. XXXIX No. 10, 1985. (Year: 1985).*
Abascal, F. et al. "Evolutionary analyses of gap junction protein families". Biochem. Biophys. Acta 2013, 1828 (1), 4-14.
Bennett, B. C. et al. "An electrostatic mechanism for Ca(2+)-mediated regulation of gap junction channels". Nat Commun 2016, 7, 8770.
Beyer, E. C. et al. "Connexin hemichannels in the lens". Front Physiol 2014, 5, 20.
Buurman, E. T. et al. "Multiple paths for nonphysiological transport of K+ in *Escherichia coli*". J. Bacteriol. 2004, 186 (13), 4238-4245.
Chang, C.-W. T. et al. "Antibacterial to antifungal conversion of neamine aminoglycosides through alkyl modification". Strategy for reviving old drugs into agrofungicides. J. Antibiot. 2010, 63 (11), 667-672.
Contreras, J. E. "Metabolic inhibition induces opening of unapposed connexin 43 gap junction hemichannels and reduces gap junctional communication in cortical astrocytes in culture". PNAS 2002, 99 (1), 495-500.
Dalamon, V. et al. "Gap-junctional channel and hemichannel activity of two recently identified connexin 26 mutants associated with deafness". Pflugers Archiv : European journal of physiology 2016.
De Vuyst, E. et al. "Pharmacological modulation of connexin-formed channels in cardiac pathophysiology". British journal of pharmacology 2011, 163 (3), 469-83.
Figueroa, V. A. et al. "Extracellular gentamicin reduces the activity of connexin hemichannels and interferes with purinergic Ca(2+) signaling in HeLa cells". Frontiers in cellular neuroscience 2014, 8, 265.
Fiori, M. C. et al. "Functional analysis and regulation of purified connexin hemichannels". Front Physiol 2014, 5, 71.
Fiori, M. C. et al. "Functional hemichannels formed by human connexin 26 expressed in bacteria". Bioscience Rep. 2015, 35 (2), e00177.
Fiori, M. C et al. "Inhibition by Commercial Aminoglycosides of Human Connexin Hemichannels Expressed in Bacteria". Molecules 2017, 22 (12), 2063.
Fosso, M. et al. "Structure-Activity Relationships for Antibacterial to Antifungal Conversion of Kanamycin to Amphiphilic Analogues". J. Org. Chem. 2015, 80 (9), 4398-4411.
Harris, A. et al. "Connexins: A Guide". Humana Press: 2009; vol. Ch. 7, pp. 165-207.
Herve, J. C. et al. "Peptides targeting gap junctional structures". Current pharmaceutical design 2010, 16 (28), 3056-70.
Kotra, L. P. et al. "Aminoglycosides: perspectives on mechanisms of action and resistance and strategies to counter resistance". Antimicrob. Agents Chemother. 2000, 44 (12), 3249-3256.
Krishnan, S. et al. "An *Escherichia coli*-Based Assay to Assess the Function of Recombinant Human Hemichannels". SLAS Discov 2017, 22 (2), 135-143.
Lee, J. R. et al. "Connexin-26 mutations in deafness and skin disease". Expert reviews in molecular medicine 2009, 11, e35.
Leithe, E. et al. "Inhibition of connexin 43 gap junction channels by the endocrine disruptor ioxynil". Toxicol. Appl. Pharm. 2010, 247 (1), 10-17.
Maeda, S. et al. "Structure of the connexin 26 gap junction channel at 3.5 A resolution". Nature 2009, 458 (7238), 597-602.

(Continued)

*Primary Examiner* — Layla D Berry
(74) *Attorney, Agent, or Firm* — Edwin S. Flores; Daniel J. Chalker; Chalker Flores, LLP

(57) ABSTRACT

The present invention includes novel molecules and methods of using an amphiphilic kanamycin molecule having substitutions at the O-4", O-6", or O-4" and O-6" positions having reduced antimicrobial activity for targeting Connexin Hemichannels.

5 Claims, 8 Drawing Sheets

(56) References Cited

OTHER PUBLICATIONS

Meşe, G. et al. "Gap junctions: basic structure and function". J. Invest. Dermatol. 2007, 127 (11), 2516-2524.
Mingeot-Leclercq, M.-P. et al. "Aminoglycosides: nephrotoxicity". Antimicrob. Agents Chemother. 1999, 43 (5), 1003-1012.
Nielsen, M. S. et al. "Gap junctions". Comprehensive Physiology 2012, 2 (3), 1981-2035.
Orellana, J. A. et al. "Role of connexins and pannexins in ischemic stroke". Curr Med Chem 2014, 21 (19), 2165-82.
Paulis, L. E. et al. "Embryonic cardiomyocyte, but not autologous stem cell transplantation, restricts infarct expansion, enhances ventricular function, and improves long-term survival". PloS one 2013, 8 (4), e61510.
Sagar, G. et al. "Carbenoxolone inhibits junctional transfer and upregulates connexin43 expression by a protein kinase A-dependent pathway". J. Cel. Biochem. 2006, 98 (6), 1543-1551.
Schulz, R. et al. "Connexin 43 is an emerging therapeutic target in ischemia/reperfusion injury, cardioprotection and neuroprotection". Pharmacol Ther 2015, 153, 90-106.
Shintani-Ishida, K. et al. "Hemichannels in cardiomyocytes open transiently during ischemia and contribute to reperfusion injury following brief ischemia". American journal of physiology. Heart and circulatory physiology 2007, 293 (3), H1714-20.
Shrestha, J. P. et al. "Synthesis and bioactivity investigation of quinone-based dimeric cationic triazolium amphiphiles selective against resistant fungal and bacterial pathogens" Eur. J. Med. Chem. 2017, 126, 696-704.
Shrestha, S. et al. "Membrane lipid-modulated mechanism of action and non-cytotoxicity of novel fungicide aminoglycoside FG08". PloS one 2013, 8 (9), e73843.
Shrestha, S. K. et al. "Antifungal amphiphilic aminoglycoside K20: bioactivities and mechanism of action". Front. Microbiol. 2014, 5 (671).
Shrestha, S. K. et al. "In vitro antifungal synergy between amphiphilic aminoglycoside K20 and azoles against *Candida* species and Cryptococcus neoformans". Med. Mycol. 2015, 53 (8), 837-844.
Stumpe, S. et al. "Requirement of a large K+-uptake capacity and of extracytoplasmic protease activity for protamine resistance of *Escherichia coli*". Arch. Microbiol. 1997, 167 (2-3), 126-136.
Tao, L. et al. "2-aminoethoxydiphenyl borate directly inhibits channels composed of connexin26 and/or connexin32". Mol. Pharmacol. 2007, 71 (2), 570-579.
Vakulenko, S. B. et al. "Versatility of aminoglycosides and prospects for their future". Clin. Microbiol. Rev. 2003, 16 (3), 430-450.
Vergara, L. et al. "Do connexin 43 gap-junctional hemichannels activate and cause cell damage during ATP depletion of renal-tubule cells?" Acta physiologica Scandinavica 2003, 179 (1), 33-8.
Wang, N. et al. "Paracrine signaling through plasma membrane hemichannels". Biochimica et biophysica acta 2013, 1828 (1), 35-50.
Willebrords, J. et al. "Inhibitors of connexin and pannexin channels as potential therapeutics". Pharmacol Ther 2017, 180, 144-160.
Zhang, Q. et al. "Divergent Synthesis of Three Classes of Antifungal Amphiphilic Kanamycin Derivatives". J. Org. Chem. 2016, 81 (22), 10651-10663.
Zhao, K. et al. "Inhibition of gap junction channel attenuates the migration of breast cancer cells". Mol. Biol. Rep. 2012, 39 (3), 2607-2613.
Subedi et al. "Antifungal amphiphilic kanamycins: new life for an old drug", Med. Chem. Commun . . . Apr. 17, 2018, vol. 9, pp. 909-919.
Alfindee et al. "Inhibition of Connexin Hemichannels by New Amphiphilic Aminoglycosides without Antibiotic Activity", ACS Med. Chem. Lett. Jun. 19, 2018. vol. 9, pp. 697-701.
International Search Report [ISA/US] PTC/US2019/036714 dated Oct. 22, 2019.

* cited by examiner

AMPHIPHILIC AMINOGLYCOSIDE CONNEXIN HEMICHANNEL INHIBITORS

CROSS-REFERENCE TO RELATED APPLICATIONS

This application claims priority to and is a continuation-in-part of International Application No. PCT/US2019/036714, filed Jun. 12, 2019, which claims priority to U.S. Provisional Application Ser. No. 62/683,673, filed Jun. 12, 2018, the entire contents of which are incorporated herein by reference.

STATEMENT OF FEDERALLY FUNDED RESEARCH

This invention was made with government support under CHE-1429195 awarded by the National Science Foundation. The government has certain rights in the invention.

TECHNICAL FIELD OF THE INVENTION

The present invention relates in general to the field of inhibitors of connexin hemichannels.

BACKGROUND OF THE INVENTION

Without limiting the scope of the invention, its background is described in connection with connexin hemichannels.

Connexins hemichannels (HCs) from adjacent cells form gap junctional channels (GJCs) that mediate cell-to-cell communication. Abnormal opening of "free" undocked HCs can produce cell damage and participate in the mechanism of disorders such as cardiac infarct, stroke, deafness, skin diseases, and cataracts. Therefore, inhibitors of connexin HCs have great pharmacological potential. Antibiotic aminoglycosides (AGs) have been recently identified as connexin HC inhibitors, however, their antibiotic effect is an issue for the treatment of disorders where infections do not play a role (e.g., cardiac infarcts).

One such invention is taught in U.S. Pat. No. 9,485,983, issued to Leybaert and entitled "Use of connexin channel inhibitors to protect grafts". Briefly, this inventor is said to teach methods to protect grafts against cell death due by preservation of the grafts prior to transplanting into patients. Connexin channel inhibitors are used to protect against cell death associated with preservation and temporary storage of cells, tissues and organs. Preservation is said to include any procedure that involves a lowering of the temperature below the normal body temperature, including hypothermia (cold storage), cryopreservation and vitrification, thereby protecting grafts with an improved biological function.

Another such invention is taught in U.S. Patent Publication No. 20170049761, filed by Kielian entitled, "Compositions and methods for the treatment of juvenile neuronal ceroid lipofuscinosis and related disorders". Briefly, this application is said to provide materials and methods for the prevention and treatment of Juvenile Neuronal Ceroid Lipofuscinosis by providing an effective amount of at least one hemichannel inhibitor or a phosphodiesterase-4 inhibitor. The hemichannel inhibitors are said to include INI-0602, glycyrrhizic acid, 18α-glycyrrhetinic acid, carbenoxolone, a carbenoxolone derivative, a carbenoxolone analog, a fenamate, flufenemic acid, a flufenemic acid derivative, a flufenemic acid analog, heptanol, octanol, arachidonic acid, quinine, a quinine derivative, a connexin (Cx) fragment, a connexin mimetic peptide, a connexin inhibitor, an anti-connexin antibody, a connexin expression modulator, a lysophosphatidic acid, an inhibitor of arachidonic acid metabolism, niflumic acid, 5-nitro-2(3-phenylpropylamino) benzoic acid and a heavy metal.

Thus, a need remains for novel composition and methods for the treatment of diseases associated with, or exacerbated by, a connexin hemichannel dysfunction.

SUMMARY OF THE INVENTION

In one embodiment, the present invention includes an amphiphilic kanamycin molecule having substitutions at the O-4", O-6", or O-4" and O-6" positions having reduced antimicrobial activity. In one aspect, the substitutions comprise linear alkyl chains. In another aspect, the substitutions comprise a benzyl group. In another aspect, the molecule has the formula:

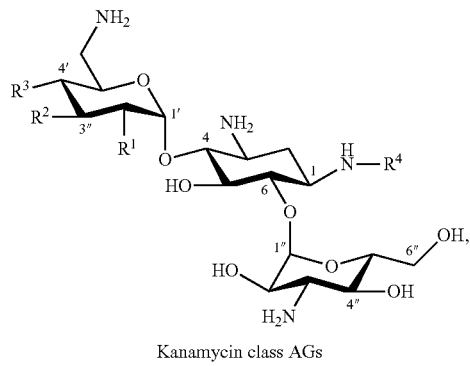

Kanamycin class AGs wherein $R^1$, $R^2$, $R^3$ and $R^4$ are methyl, ethyl, propyl, butyl, or linear alkyl, alkylcarbonyl chains or cyclic groups. In another aspect, the molecules have substantially no antimicrobial activity. In another aspect, the molecules have no antibacterial activity. In another aspect, the molecules have moderate antifungal activity. In another aspect, the molecule inhibits connexin hemichannels. In another aspect, the molecule has hydrophobic groups at positions O-4", O-6". In another aspect, the molecule has formula:

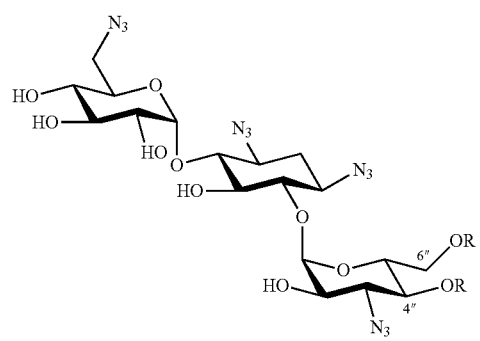

7b-h wherein R in compounds 7b to 7h is selected from:
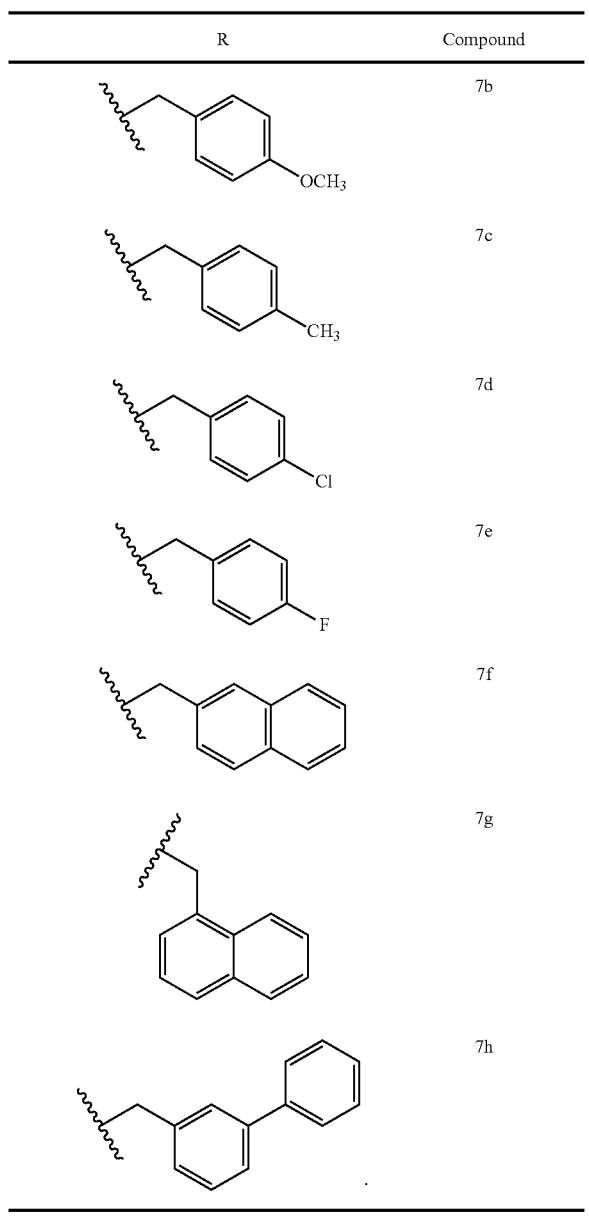
In another aspect, the molecule has formula:
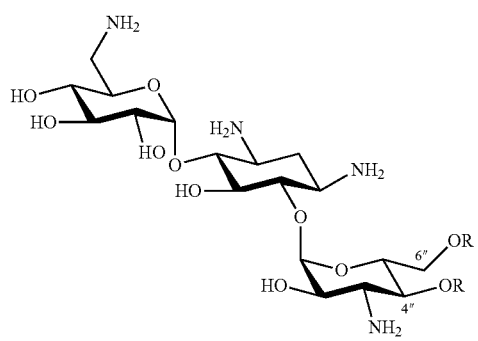
wherein R in compounds 10-16 comprises:
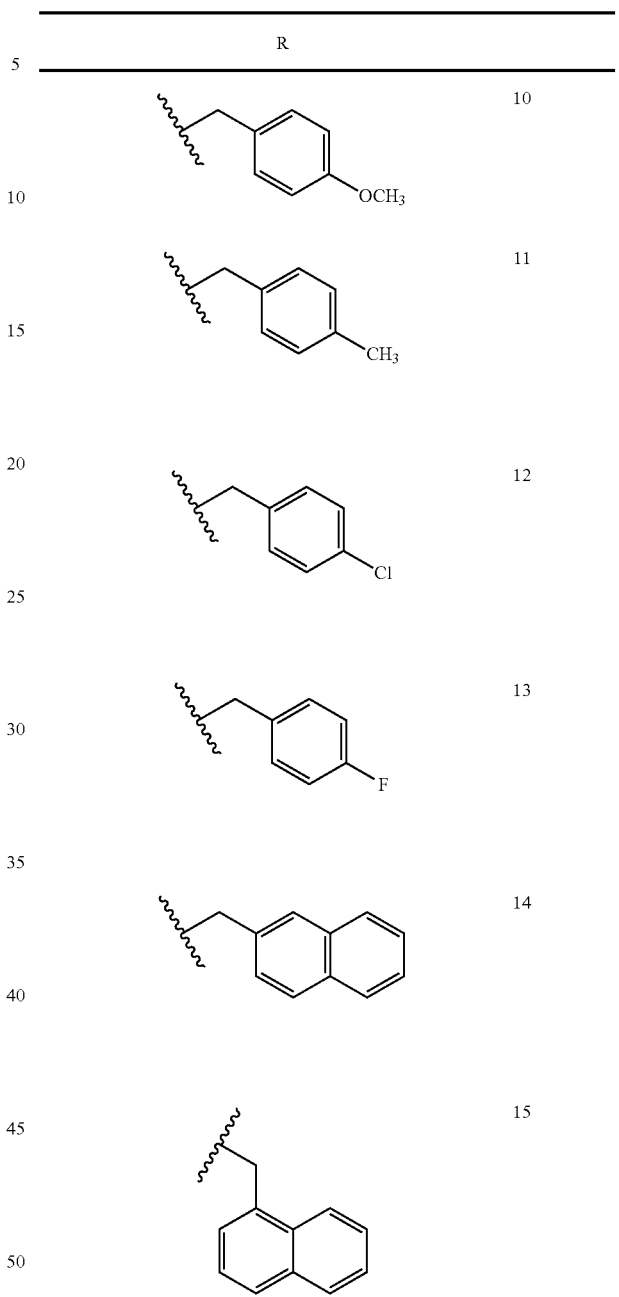
In another embodiment, the present invention includes a method of making an amphiphilic kanamycin molecule having substitutions at the O-4", O-6", or O-4" and O-6" positions having reduced antimicrobial activity comprising:

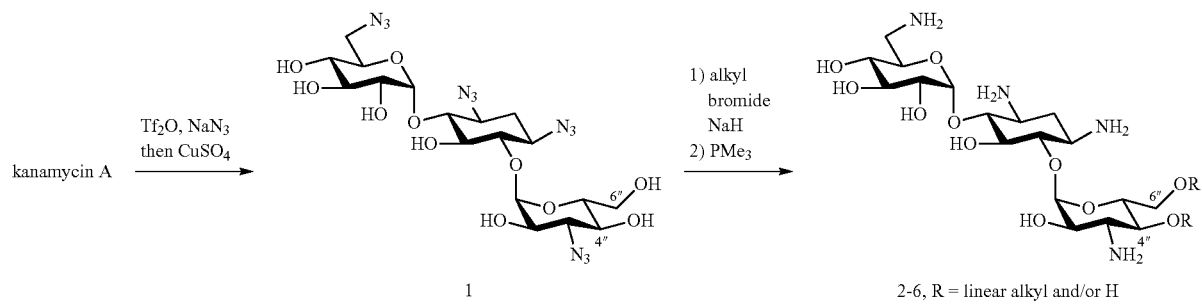
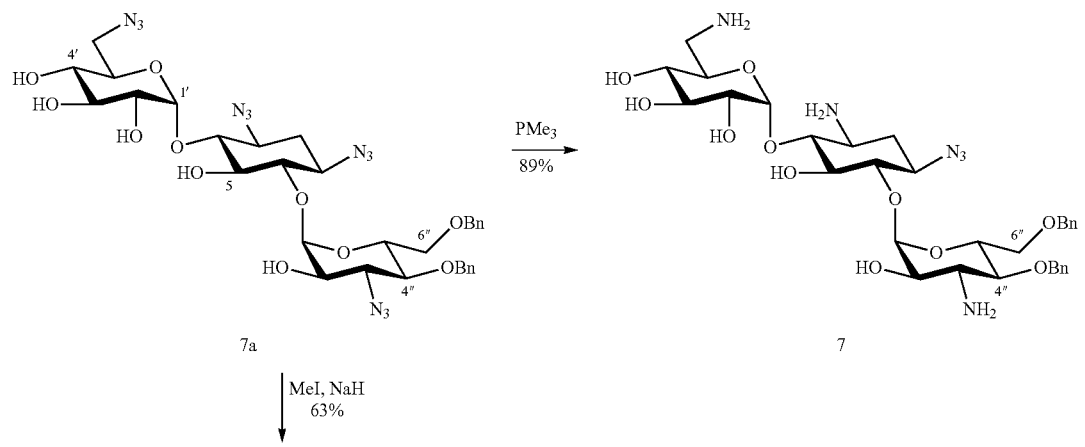
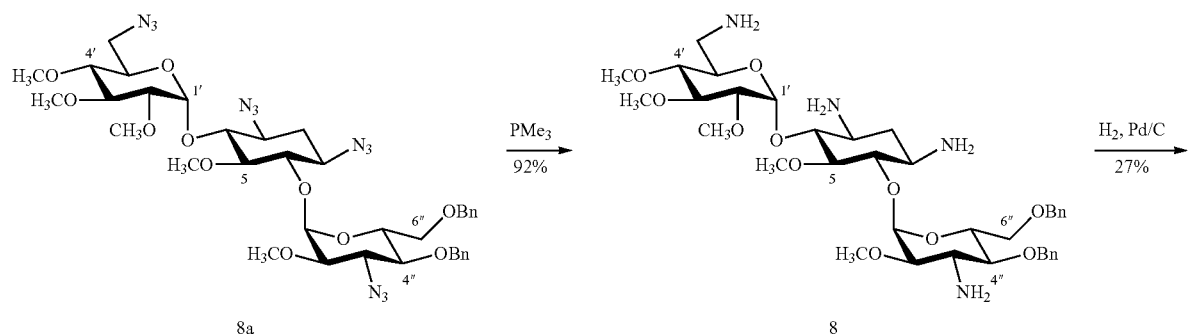
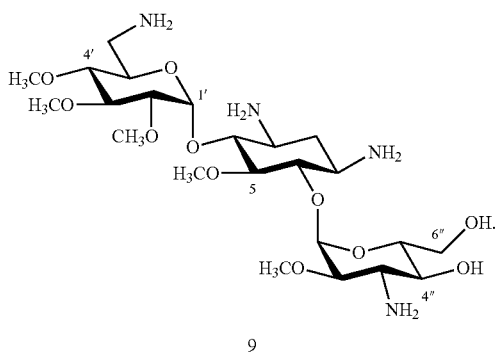

In one aspect, the method further comprises the steps of:

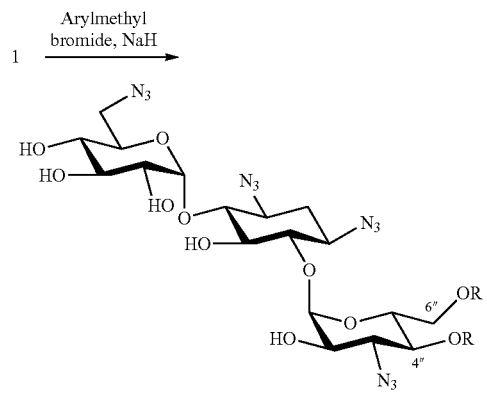

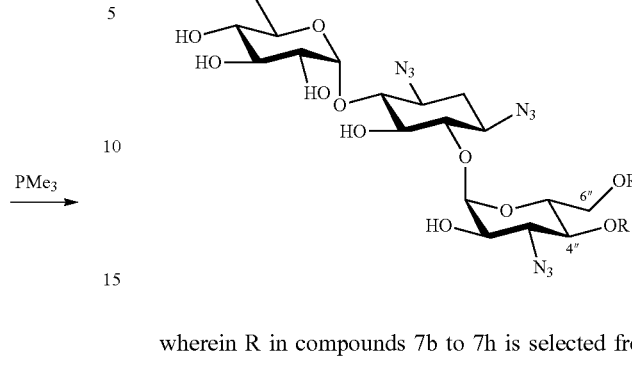

wherein R in compounds 7b to 7h is selected from:

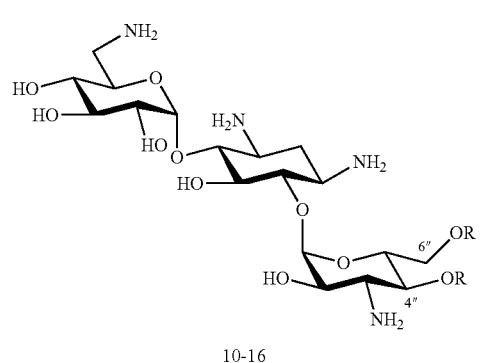

In another aspect, the substitutions comprise linear alkyl chains. In another aspect, the substitutions comprise a benzyl group. In another aspect, the molecule has the formula:

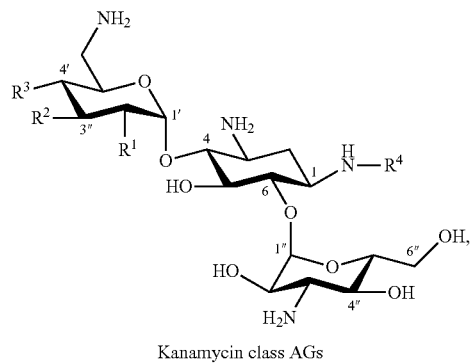

Kanamycin class AGs wherein $R^1$, $R^2$, $R^3$ and $R^4$ are methyl, ethyl, propyl, butyl, or linear alkyl chains or cyclic groups. In another aspect, the molecules have substantially no antimicrobial activity. In another aspect, the molecules have no antibacterial activity. In another aspect, the molecules have moderate antifungal activity. In another aspect, the molecule inhibits connexin hemichannels. In another aspect, the molecule has hydrophobic groups at positions O-4", O-6". In another aspect, the molecule has formula:

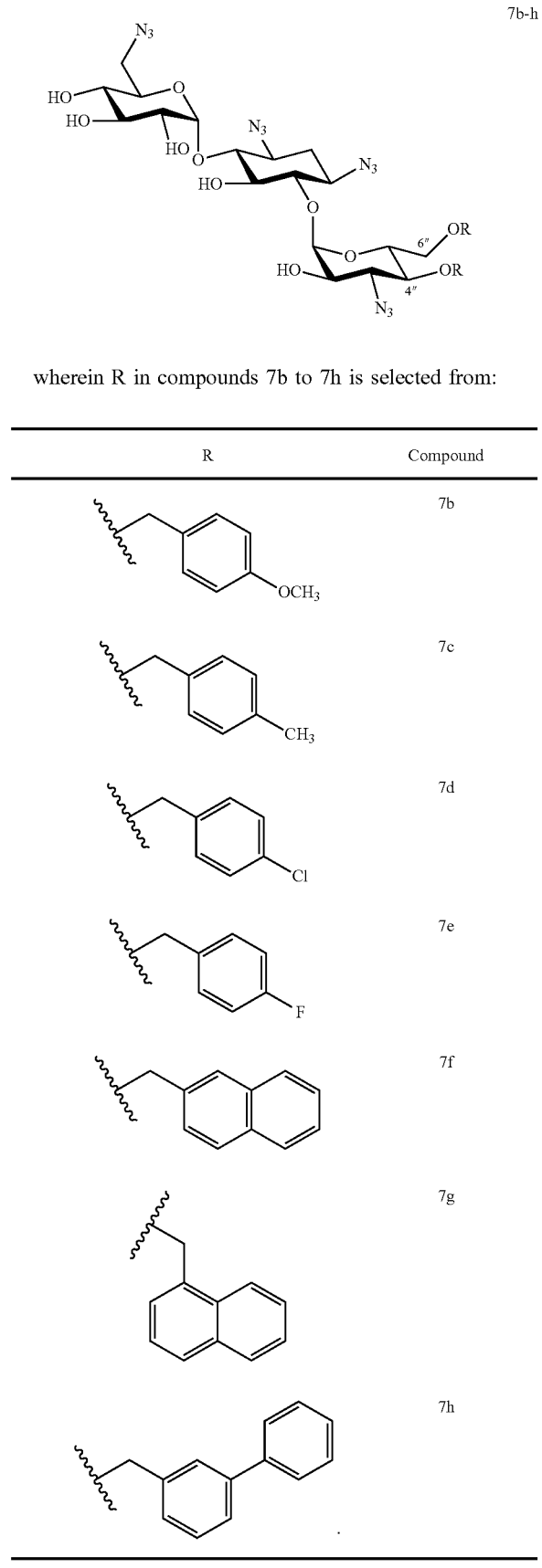

In another aspect, the molecule has formula:

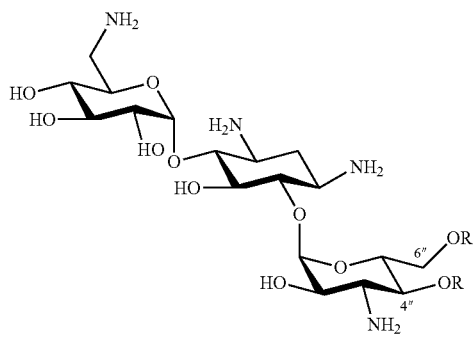

10-16 wherein R in compounds 10-16 comprises:

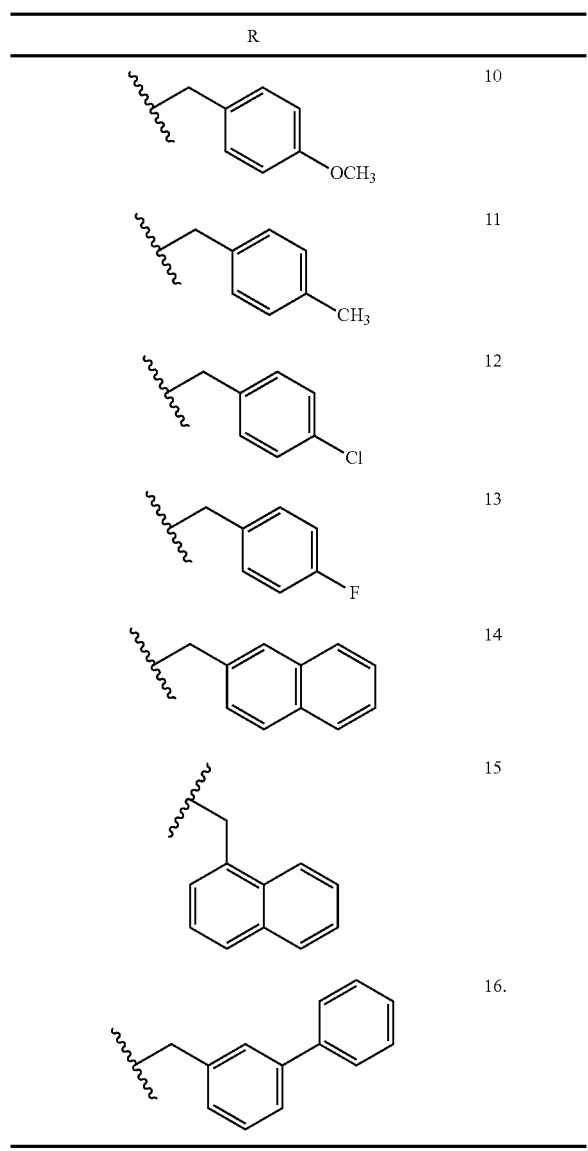

In another embodiment, the present invention includes a method of treating a subject with a disease or condition caused by, or exacerbated by, a connexin hemichannel deficiency comprising: identifying a subject in need of treatment for the disease or condition associated with the connexin hemichannel deficiency; and providing the subject with an effective amount of an amphiphilic kanamycin molecule having substitutions at the O-4", O-6", or O-4" and O-6" positions having reduced antimicrobial activity that inhibits connexin hemichannels. In one aspect, the disease or condition associated with the connexin hemichannel deficiency is selected from cardiac infarct, stroke, deafness, skin diseases, and cataracts. In another aspect, the substitutions comprise linear alkyl chains or benzyl groups. In another aspect, the molecule has the formula:

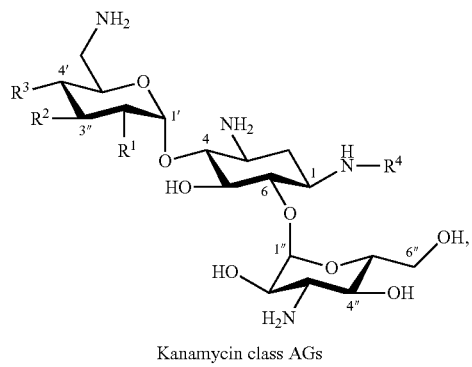

Kanamycin class AGs wherein $R^1$, $R^2$, $R^3$ and $R^4$ are methyl, ethyl, propyl, butyl, or linear alkyl chains or cyclic groups. In another aspect, the molecules have substantially no antimicrobial activity. In another aspect, the e molecules have no antibacterial activity. In another aspect, the molecules have moderate antifungal activity. In another aspect, the molecule has hydrophobic groups as positions O-4", O-6". In another aspect, the molecule has formula:

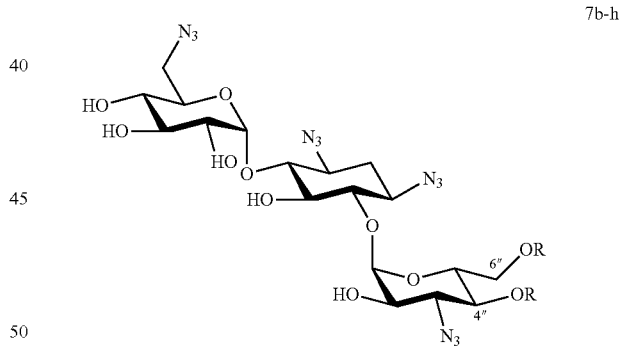

7b-h wherein R in compounds 7b to 7h is selected from:

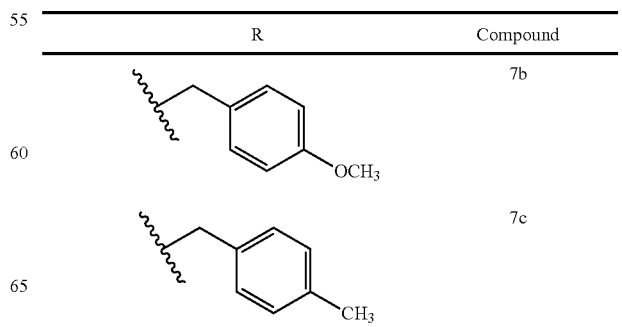

-continued

| R | Compound |
|---|---|
| (4-chlorobenzyl) | 7d |
| (4-fluorobenzyl) | 7e |
| (2-naphthylmethyl) | 7f |
| (1-naphthylmethyl) | 7g |
| (3-biphenylmethyl) | 7h |

In another aspect, the molecule has formula:

10-16 wherein R in compounds 10-16 comprises:

| R | |
|---|---|
| (4-methoxybenzyl) | 10 |

-continued

| R | |
|---|---|
| (4-methylbenzyl) | 11 |
| (4-chlorobenzyl) | 12 |
| (4-fluorobenzyl) | 13 |
| (2-naphthylmethyl) | 14 |
| (1-naphthylmethyl) | 15 |
| (3-biphenylmethyl) | 16 |

In another embodiment, the present invention includes a molecule comprising the formula:

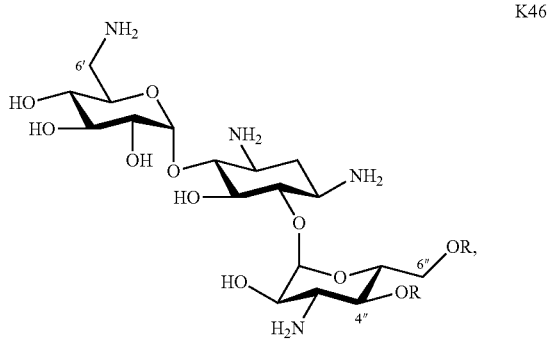

K46 wherein
| Code/compound # | R |
|---|---|
| K46B01/7 | Benzyl; |
| K46BM5/8 | Benzyl and all hydroxyl groups were methylated; |
| K46B09/10 | 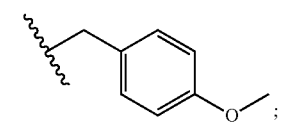 [SMILES: *Cc1ccc(OC)cc1] |
| K46B03/11 | 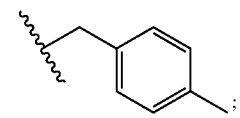 [SMILES: *Cc1ccc(C)cc1] |
| K46B10/12 | 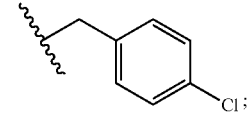 [SMILES: *Cc1ccc(Cl)cc1] |
| K46B04/13 | 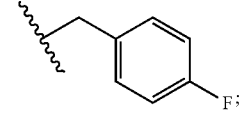 [SMILES: *Cc1ccc(F)cc1] |
| K46B05/14 | 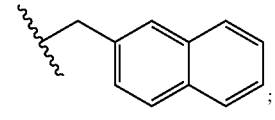 [SMILES: *Cc1ccc2ccccc2c1] |
| K46B11/15 | 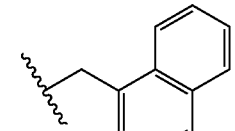 |
| K46B07/16 |  |
| K4604/2 | Butyl; |
| K4606/3 | Hexyl; |
| K4608/5 | Octyl; or |
| K4609/6 | Nonyl. |
In another embodiment, the present invention includes a method of making an amphiphilic kanamycin molecule comprising:
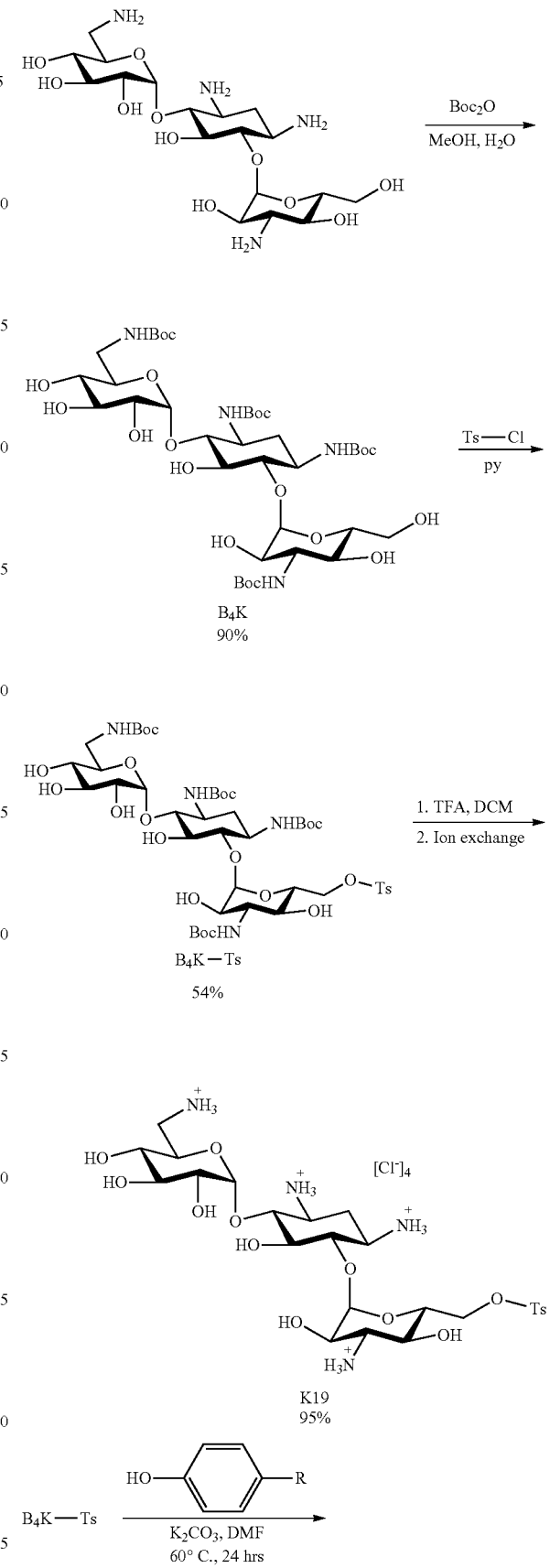

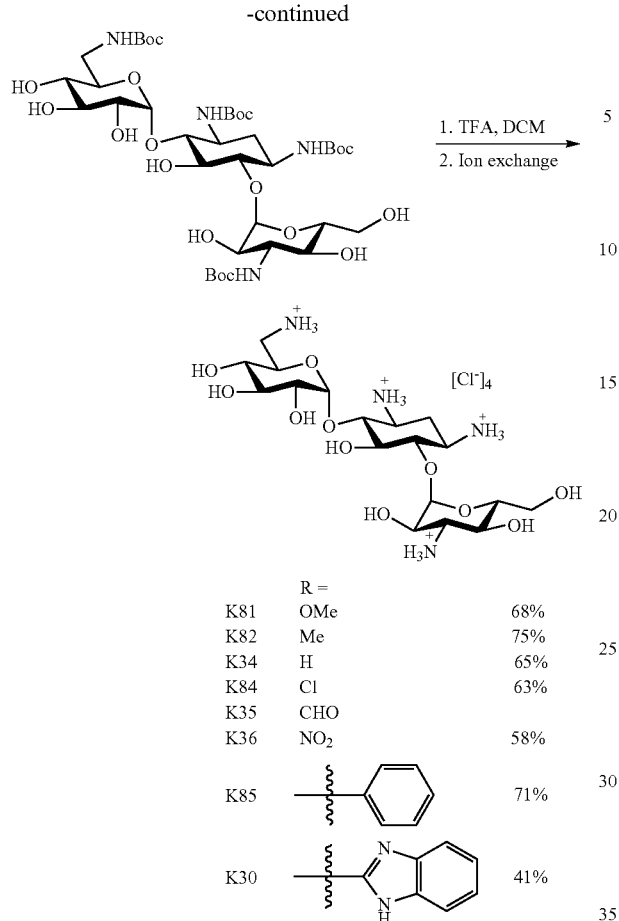
| | R = | |
|---|---|---|
| K81 | OMe | 68% |
| K82 | Me | 75% |
| K34 | H | 65% |
| K84 | Cl | 63% |
| K35 | CHO | |
| K36 | NO₂ | 58% |
| K85 | (phenyl) | 71% |
| K30 | (benzimidazole) | 41% |
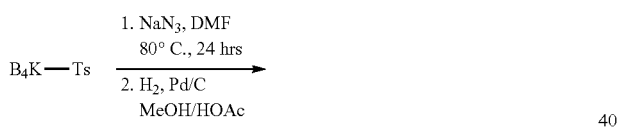
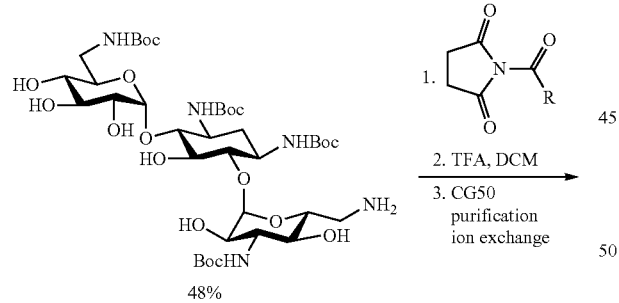
48%
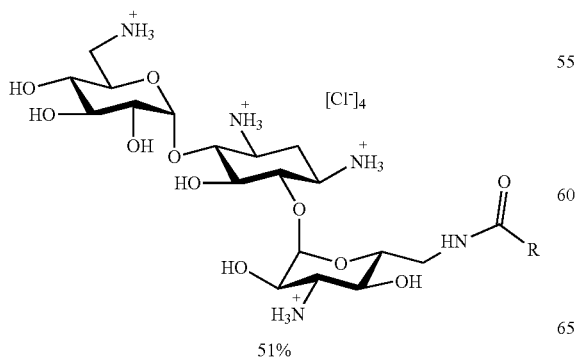
51%
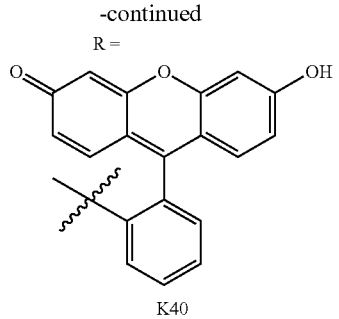
K40
In one aspect, the method further comprising the steps of:
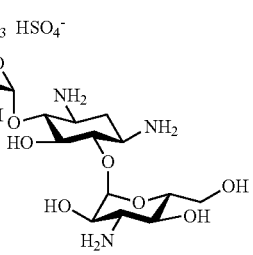
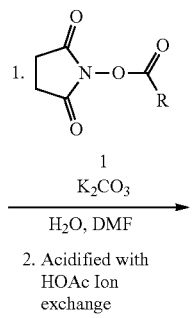
| | R' | |
|---|---|---|
| KI01 | $C_5H_{11}$ | 66% |
| KI02 | $C_7H_{15}$ | 84% |
| KI03 | $C_9H_{19}$ | 55% |
| KI04 | $C_{11}H_{23}$ | 57% |
| KI05 | $C_{13}H_{27}$ | 70% |
| KI06 | $C_{15}H_{31}$ | 64% |
| KI07 | $C_{17}H_{35}$ | 43% |

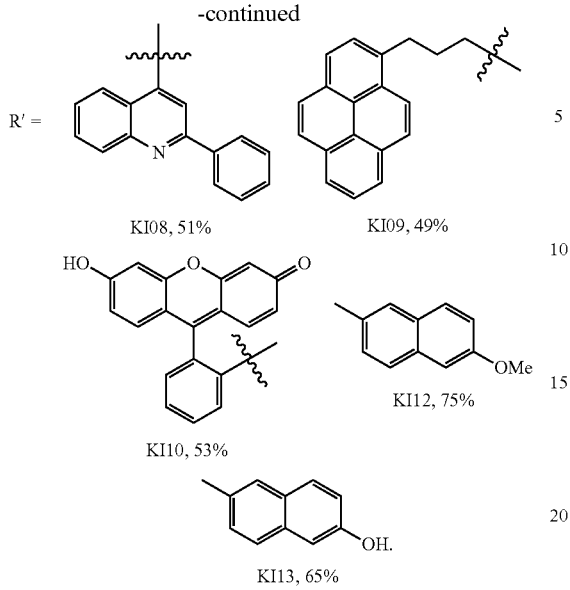
In another embodiment, the present invention includes a molecule having the formula:
| Code | Structures |
|------|------------|
| K19  | 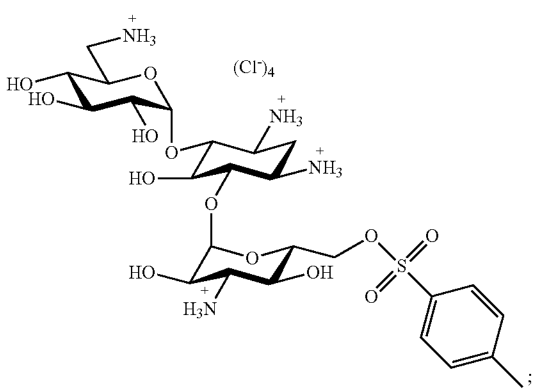           |
| K30  | 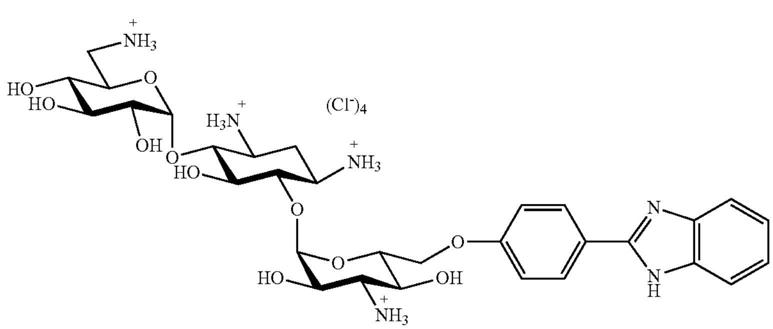           |

| Code | Structures |
|---|---|
| K34 | 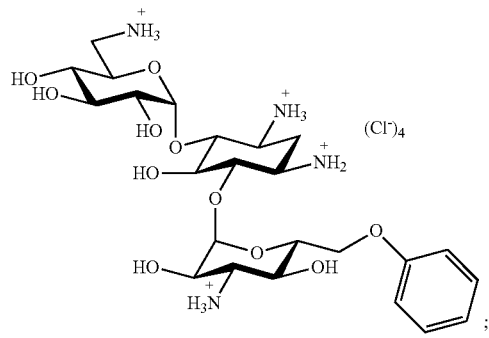 |
| K36 | 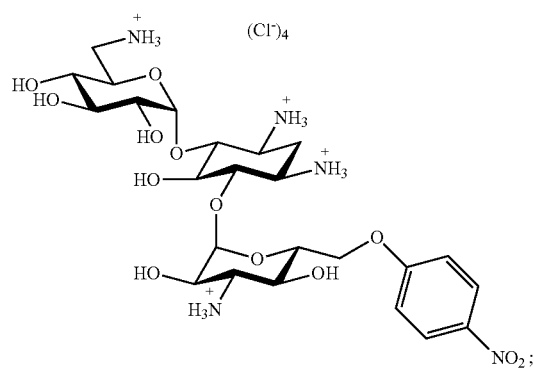 |
| K40* | 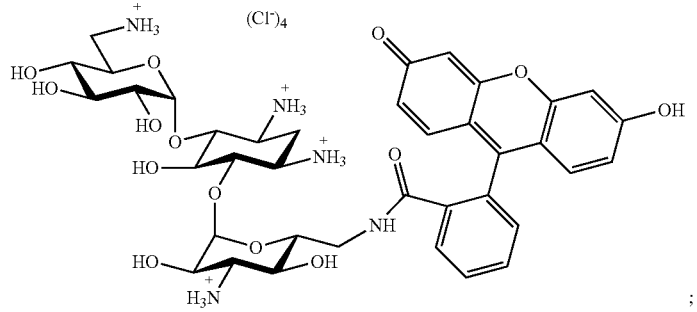 |
| K81 | 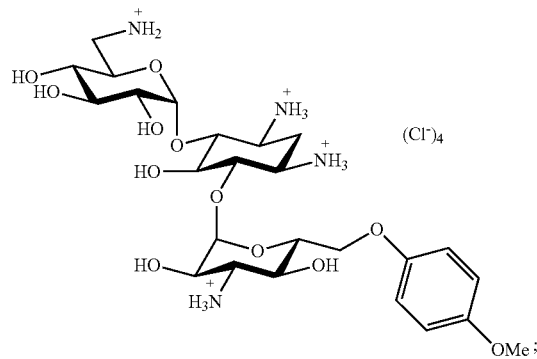 |

-continued
| Code | Structures |
|---|---|
| K82 | 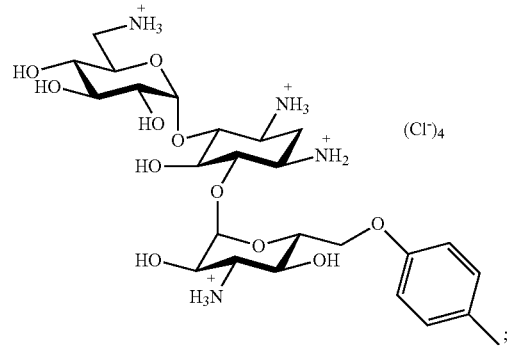 |
| K84 | 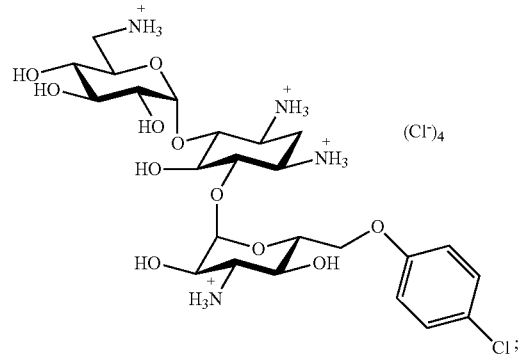 |
| K85 | 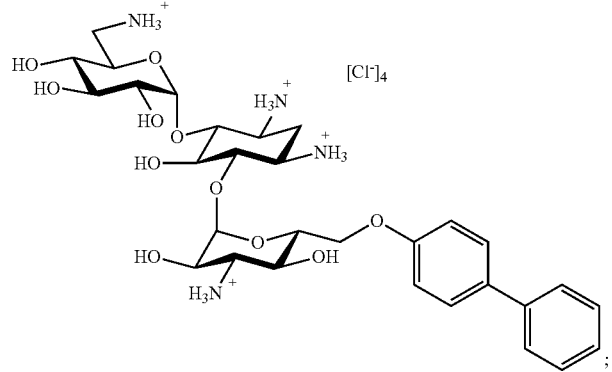 |
| KI01 | 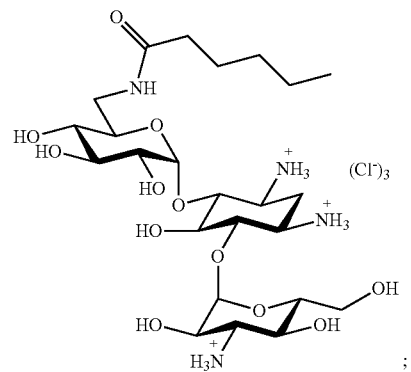 |

-continued
| Code | Structures |
|---|---|
| KI02 | 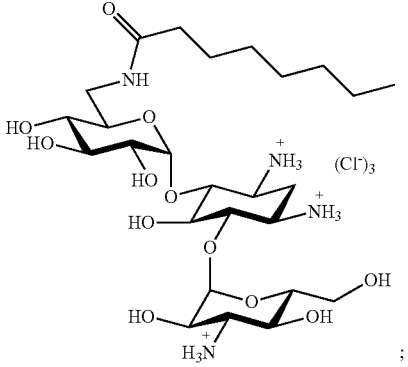 ; |
| KI03 | 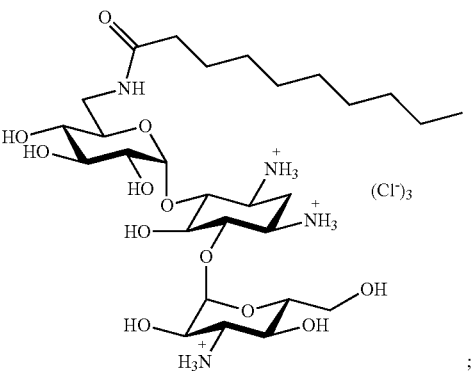 ; |
| KI04 | 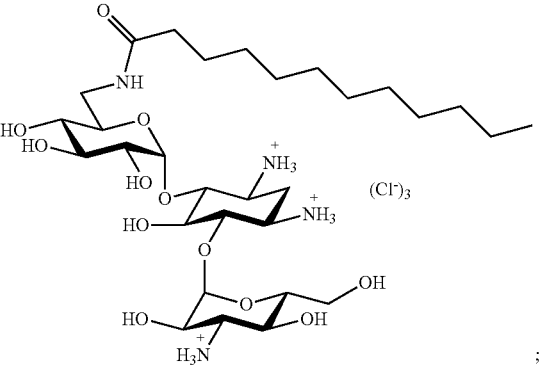 ; |
| KI05 | 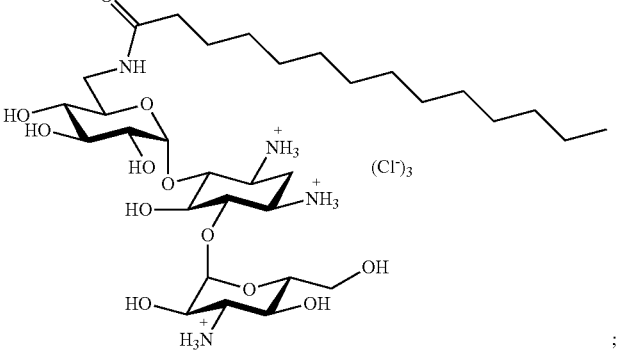 ; |

-continued
| Code | Structures |
|------|------------|
| KI06 | 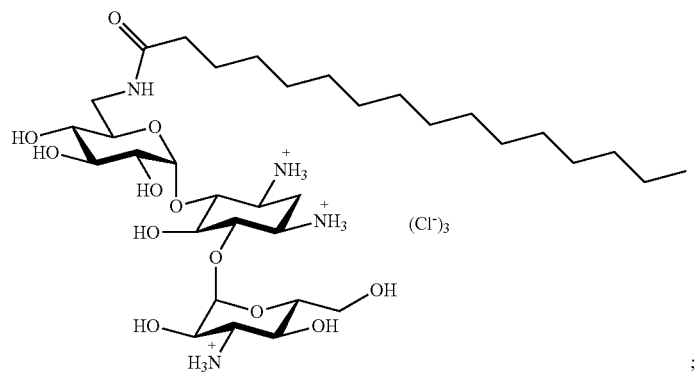 |
| KI07 | 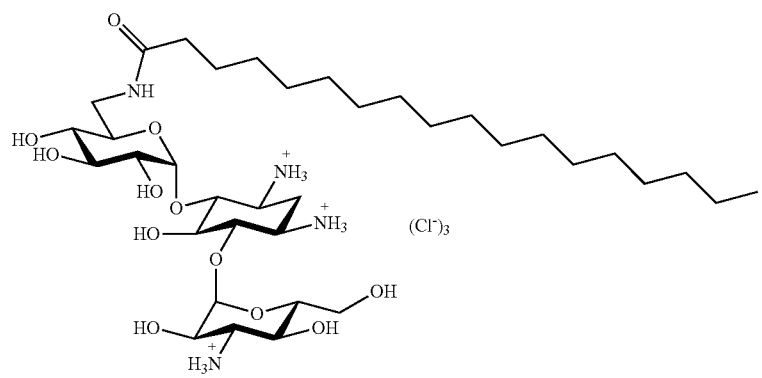 |
| KI08 | 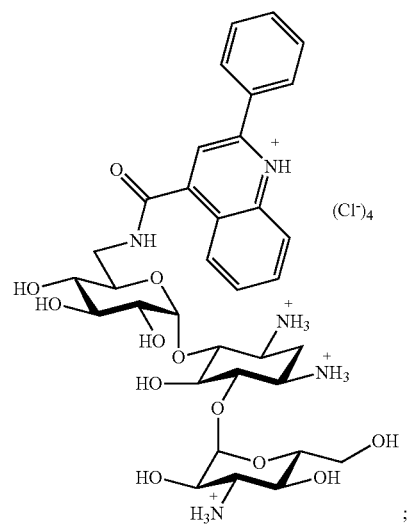 |

-continued
| Code | Structures |
|---|---|
| KI09 | 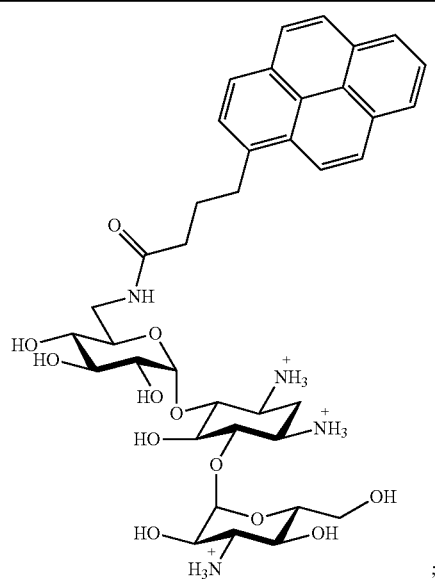 |
| KI10 | 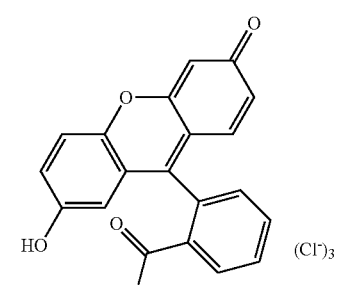 |
| KI12 | 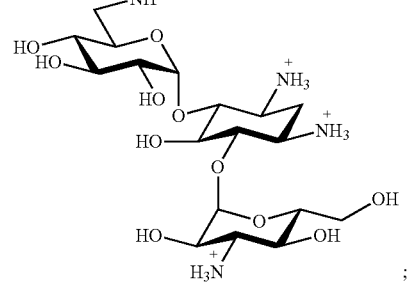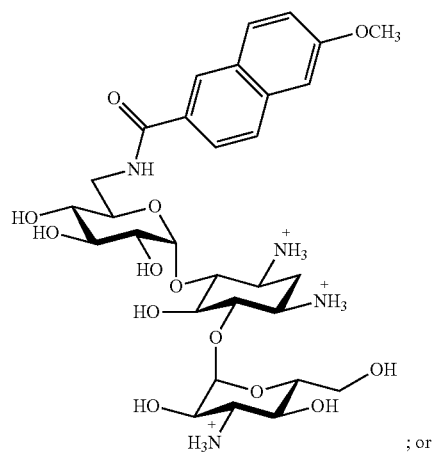 ; or |

-continued

| Code | Structures |
|---|---|
| KI13 | 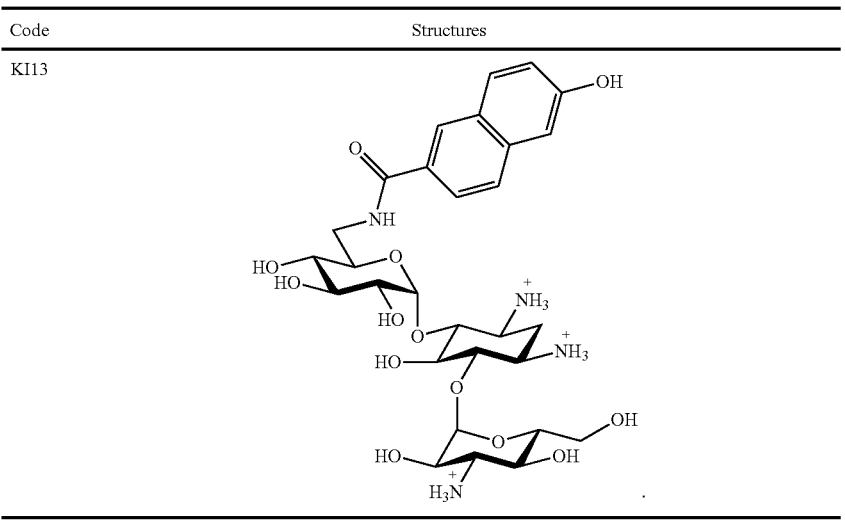 |

BRIEF DESCRIPTION OF THE DRAWINGS

For a more complete understanding of the features and advantages of the present invention, reference is now made to the detailed description of the invention along with the accompanying figures and in which:

FIG. 6A is a No-pREP that corresponds to the evaluation of the antibiotic effect of the compounds in kanamycin-sensitive LB2003 cells grown in high-K+ medium. + FIG. 6B shows pREP corresponds to the cytotoxic effect of the compounds in kanamycin-resistant LB2003 cells grown in high-K+ medium. The data were normalized to the growth in the absence of drugs, and # and * denote $P<0.05$ and $P<0.01$ vs. growth in the absence of drugs, respectively.

DETAILED DESCRIPTION OF THE INVENTION

Figure 1:
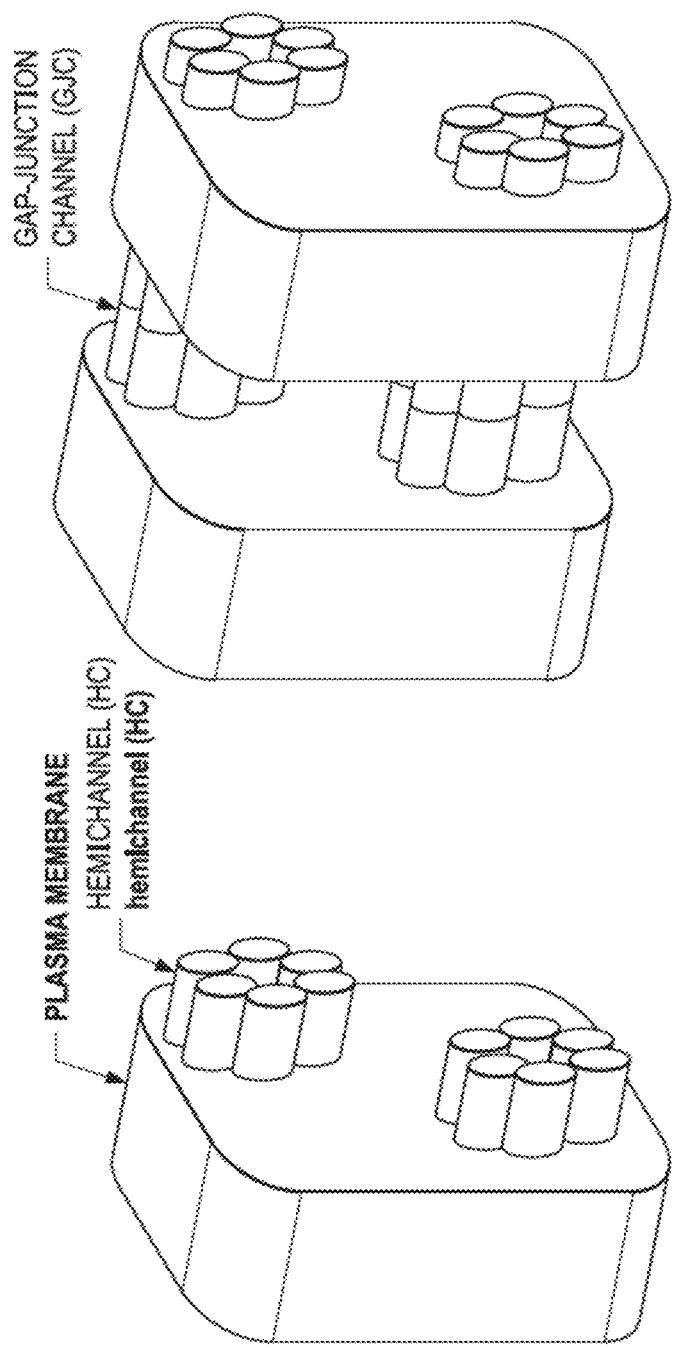
FIG. 1. Schematic representation of connexin hemichannels (HCs) and gap junction channels (GJCs). Each cylinder corresponds to a connexin monomer that has four transmembrane helices.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Abbreviations: AG, aminoglycoside; Bn, benzyl; GJC, gap junction channel; HC, hemichannel; IC50, concentration that produces 50% inhibition; Me, methyl; MIC, minimum inhibitory concentrations; SAR, structure-activity relationship.

Connexins hemichannels (HCs) from adjacent cells form GJCs that mediate cell-to-cell communication. Abnormal opening of "free" undocked HCs can produce cell damage and participate in the mechanism of disorders such as cardiac infarct, stroke, deafness, skin diseases, and cataracts. Therefore, inhibitors of connexin HCs have great pharmacological potential. Antibiotic aminoglycosides (AGs) have been recently identified as connexin HC inhibitors, but their antibiotic effect is an issue for the treatment of disorders where infections do not play a role (e.g., cardiac infarcts). The present inventors have synthesized and tested several amphiphilic AGs without antibiotic effect for their inhibition against connexin HCs, using a newly developed cell-based bacterial growth complementation assay. Several leads with superior potency than the parent compound, kanamycin A, were identified. Unlike traditional AGs, these amphiphilic AGs are not bactericidal and are not toxic to mammalian cells, making them better than traditional AGs as HC inhibitors for clinical use and other applications.

Accordingly, the present invention addresses the need for an AG composition for delivery to a mammal that, unlike conventional AG compositions, has reduced or no antimicrobial activity and is a therapeutically effective connexin HC inhibitor.

Cell-to-cell communication is essential for transporting metabolites, ions, and signal molecules between adjacent cells. This occurs predominantly through GJCs that are formed by head-to-head "docking" of two connexin HCs (connexin hexamers), one from each of the adjacent cells (FIG. 1)[1-6]. There are 21 human connexin isoforms that form a variety of GJCs and HCs that differ in permeability and regulation[1-4]. The role of GJCs in physiological processes and in disease has been known for many years, but the presence of undocked HCs in the plasma membrane, and understanding of their role in health and disease, is more recent[7-8]. Under normal conditions, HCs are mostly closed, but participate in autocrine and paracrine signaling through the efflux of molecules such as ATP, $NAD^+$, glutamate and prostaglandins[9]. HCs also seem to play a role in the pathophysiology of important and frequent disorders such as deafness, cataracts and ischemic damage of the heart, brain and kidneys[10-15]. HCs can cause or contribute to cell damage by causing depolarization, cell swelling, and alterations in cellular electrolytes, metabolites and second messengers, which results from abnormal opening of the non-selective "large" transport pathway of HCs. There is interest in the finding and development of connexin HC inhibitors since they could offer insights on the role of HCs in normal function and disease, as well as serve as therapeutics in connexin HC-associated disorders[8, 13-14, 16].

Figure 2:
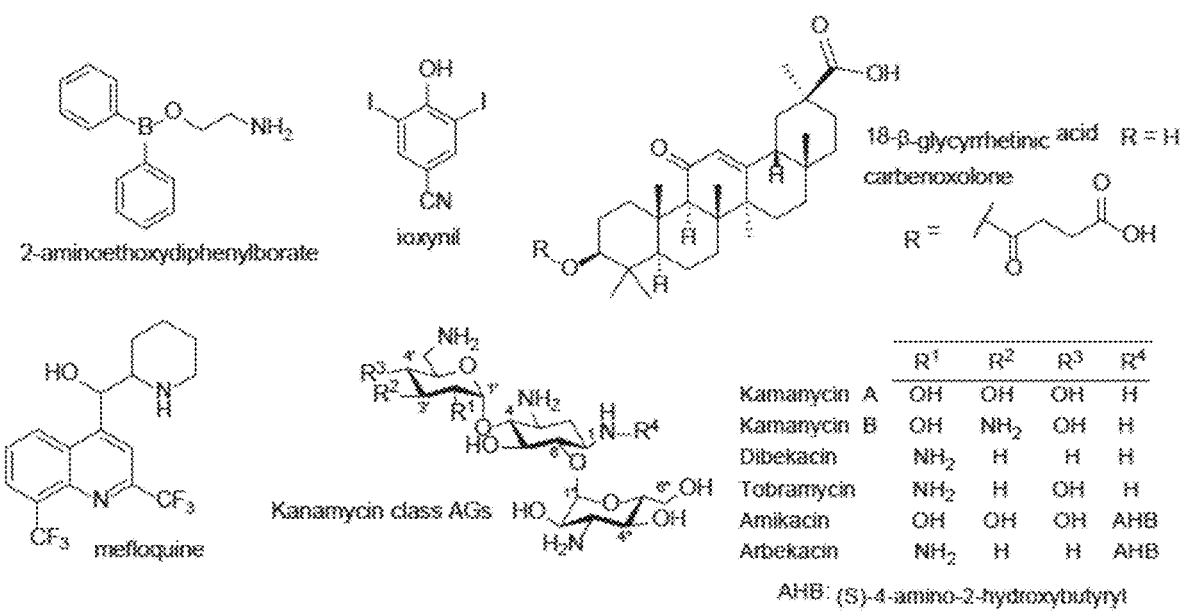
FIG. 2. Examples of inhibitors of connexin HCs of the prior art.

FIG. 1 shows a schematic representation of connexin hemichannels (HCs) and gap-junction channels (GJCs). Each cylinder corresponds to a connexin monomer that has four transmembrane helices. A variety of molecules have been investigated for their inhibitory effect toward connexin HCs, including 2-aminoethoxydiphenyl borate[17], ioxynil[18], carbenoxolone[19], 18-b-glycyrrhetinic acid[20], antimalarial drugs (mefloquine)[21] and n-alkanols[22] (FIG. 2). These cannot be used as starting points for the development of clinically useful HC inhibitors because they are not selective for connexin HCs and/or they are toxic. Connexin peptide inhibitors are synthetic peptides corresponding to sequences of connexins' extracellular or intracellular loops[23-24]. Some of the connexin peptide inhibitors have been used to treat arrhythmias and to accelerate wound healing[23-24]. Most of these peptides act on GJCs and HCs, but a few seem to selectively inhibit HCs[25]. However, the clinical potential of these peptides is still unclear, and nevertheless, other avenues to develop clinically useful HC inhibitors have been largely unexplored. In this context, AGs such as kanamycin and gentamicin have been recently identified as strong inhibitors of connexin HCs[26-29]. AGs have been used as antibacterial agents for over sixty years, and they are still among the most used antibiotics[30-31]. Although nephrotoxicity and ototoxicity are relatively common complications of AGs treatment, they can be managed[32].

The present inventors have developed chemically modified AGs, especially amphiphilic kanamycin derivatives that have biological activity, while showing significantly reduced cytotoxicity[33-38]. With this in mind, the inventors synthesized and explored amphiphilic kanamycin derivatives as connexin HC inhibitors, using connexin 26 (Cx26) HCs as test targets.

A three-step synthesis was used to make amphiphilic kanamycin derivatives bearing linear alkyl chains at the O-4", O-6", or O-4" and O-6" positions of kanamycin A (Scheme 1)[34]. These derivatives show moderate antifungal activity and no antibacterial activity, making them good candidates as HC inhibitors without antibiotic effect; they could be used without the risk of promoting the generation of AG-resistant bacterial strains. Five amphiphilic kanamycin A derivatives were selected randomly for testing. To provide more information in structure-activity relationship (SAR), the inventors also synthesized three additional derivatives: one with a benzyl (Bn) group attached at O-4" and O-6" positions (compound 7); and two with and without a Bn group attached at O-4" and O-6" positions, and a methyl (Me) group at other hydroxyl groups (5, 2', 3', 4' and 2") (compounds 8 and 9). These derivatives were prepared by sequential benzylation and methylation followed by reduction of azido groups or hydrogenolysis of the Bn. To elucidate the role of amino groups, compound 1 (Scheme 1) was also tested. Connexin HC inhibition was conducted using a bacteria-based assay of HC function[39]. In this assay, Cx26 HCs are expressed in E. coli LB2003 cells, which lack three major $K^+$ uptake systems (Kdp, Kup and Trk), and as a result they cannot grow in low-$[K^+]$ media[39-41]. However, growth of this E. coli strain in low-$[K^+]$ medium can be rescued by expression of $K^+$-permeable channels such as connexin HCs[39, 42-43]. Under the conditions of the assay (LB2003 cells expressing HCs and grown in low-$K^+$ medium), inhibition of the HCs reduces or abolishes growth[39, 42-43]. This is a simple assay where bacterial growth in multi-well plates can be followed by measuring the absorbance at 600 nm $(OD_{600})$[29]. Although not formally needed for most of the AGs tested here (they do not have antibiotic effect), the inventors routinely transform the E. coli LB2003 with plasmid that codes for the AG modifying enzyme aminoglycoside 3'-phosphotransferase, which makes the cells resistant to kanamycin A and its derivatives[39].

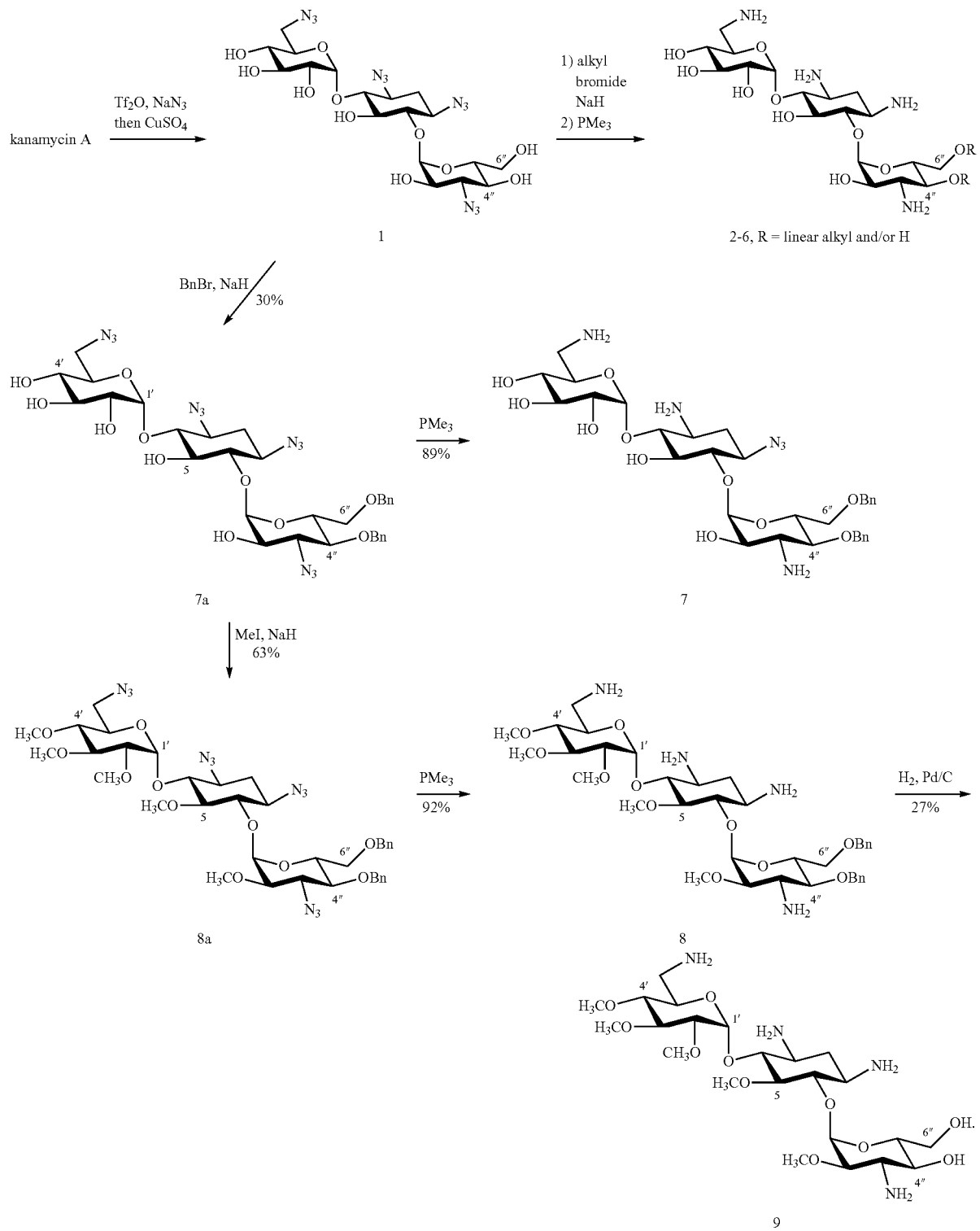

Scheme 1.

The kanamycin derivative without free amino group (compound 1) was inactive, suggesting an essential role of this group. One of the di-substituted derivatives (compound 3) displayed a lower $IC_{50}$ for inhibition of growth dependent on Cx26 than the mono-substituted compound 4 (Table 1). Compared to compound 3 (hexyl), the potency was reduced when the alkyl chain length was shortened to butyl in compound 2 or extended to octyl (compound 5) or nonyl (compound 6). The potency of compounds 7 and 8 was similar, implying that the presence of hydroxyl groups, or the associated hydrogen bond interactions, is not necessary for the AG effect on HCs. However, the lack of inhibitory activity of compound 9 demonstrates that having hydrophobic groups at O-4" and/or O-6" positions is essential in the absence of hydroxyl groups (compare compounds 8 and 9). The maximal inhibition of growth dependent on Cx26 was similar to that of kanamycin A, and was not statistically different among the new compounds with inhibitory effect (compounds 2-8), averaging 99±3%.

TABLE 1

Inhibition of Cx26 by kanamycin A and synthetic AGs

| Entry | Aminoglycoside | Type of Modification | $IC_{50}$ (µM) |
|---|---|---|---|
| 1 | Kanamycin A | — | 9.4 ± 1.1 |
| 2 | 2 | butyl at O-4" and O-6" | 19.0 ± 2.8 |
| 3 | 3 | hexyl at O-4" and O-6" | 6.2 ± 1.4 |
| 4 | 4 | hexyl at O-4" | 13.5 ± 1.8 |
| 5 | 5 | octyl at O-4" and O-6" | 13.6 ± 0.5 |
| 6 | 6 | nonyl at O-4" and O-6" | 18.8 ± 1.3 |
| 7 | 7 | Bn at O-4" and O-6" | 7.6 ± 1.2 |
| 8 | 8 | Me at 5, 2', 3', 4' and 2", Bn at O-4" and O-6" | 8.4 ± 1.4 |
| 9 | 9 | Me at 5, 2', 3', 4' and 2" | No inhibition at 100 µM |
| 10 | 1 | — | No inhibition at 100 µM |

A library of kanamycin derivatives bearing arylmethyl substituents was synthesized to investigate two factors related to SAR the electronic and steric (size) effects of the aryl group; see Scheme 2 and Table 2. The inventors selected four benzene derivatives with electron-donating and withdrawing substituents (methoxy, methyl, chloro and fluoro) at the para position to explore the first factor. Three arylmethyl groups, 1-naphthalenemethyl, 2-naphthalenemethyl, and biphenyl, were selected for studying the second factor. The synthesis was conducted as described previously[19], using commercially available arylmethyl bromides. When alkylating compound 1, the inventors observed a significant amount of mono-substituted adducts bearing arylmethyl groups at O-4" or O-6" positions. Attempts to improve the yields for di-substituted adducts by varying the equivalents of arylmethyl bromides or separating two mono-substituted adducts using flash chromatography were unsuccessful. Therefore, only the di-substituted adducts were isolated to proceed toward the completed synthesis. The $IC_{50}$ values for inhibition by these derivatives are summarized in Table 2. It appears that the relationship between the electronic effect and inhibitory potency is not strong, but rather subtle. Compounds with a moderate electron-donating group ($CH_3$—, compound 11) or moderate electron-withdrawing group (Cl—, compound 12) showed better activities than those with a strong electron-donating ($CH_3O$—) group (compound 10) or a strong electron-withdrawing (F) group (compound 13). Compounds 11 and 12 had superior inhibitory potency than kanamycin A and the parent compound 7, which has no substituent on the benzene ring. The inhibitory potency of the derivative with a bi-cyclic aromatic ring (compound 14) was slightly higher than that of compounds 15 and 16, but the differences were not major. Combining these results, it seems that compounds 11, 12 and 14 can all serve as leads for further development. The maximal inhibition of growth dependent on Cx26 was similar for compounds 10-16, and averaged 94±2%.

Combining these results, it seems that the structural (size) factor of the arylmethyl group has a greater impact on Cx26 HC inhibition. Nevertheless, it seems that compounds 11, 12 and 14 can all serve as leads for further modifications and analysis. Examples of growth inhibition by three of the new aminoglycosides, including compound 12, are shown in FIG. 3.

Figure 3A:
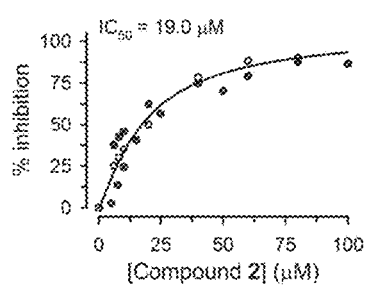
FIGS. 3A to 3C are graphs that show the inhibition of Cx26-dependent growth complementation by three of the new amphiphilic AGs. Each symbol corresponds to a triplicate average, and each color corresponds to an independent experiment. The lines are the fits of the Hill's equation to the data. Growth inhibition was significant ($P<0.01$ vs. growth in the absence of drug) for the three compounds.
Figure 3B:
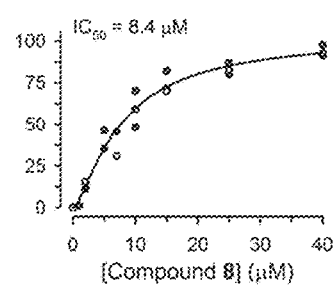
Figure 3C:
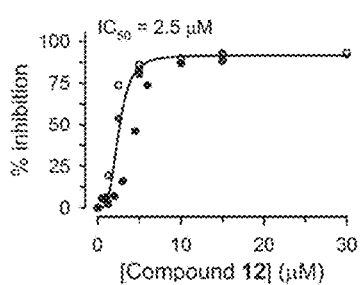

FIGS. 3A to 3C are graphs that show the inhibition of Cx26-dependent growth complementation by three of the new amphiphilic AGs. Each symbol corresponds to a triplicate average, and each color corresponds to an independent experiment. The lines are the fits of the Hill's equation to the data. Growth inhibition was significant (P<0.01 vs. growth in the absence of drug) for the three compounds.

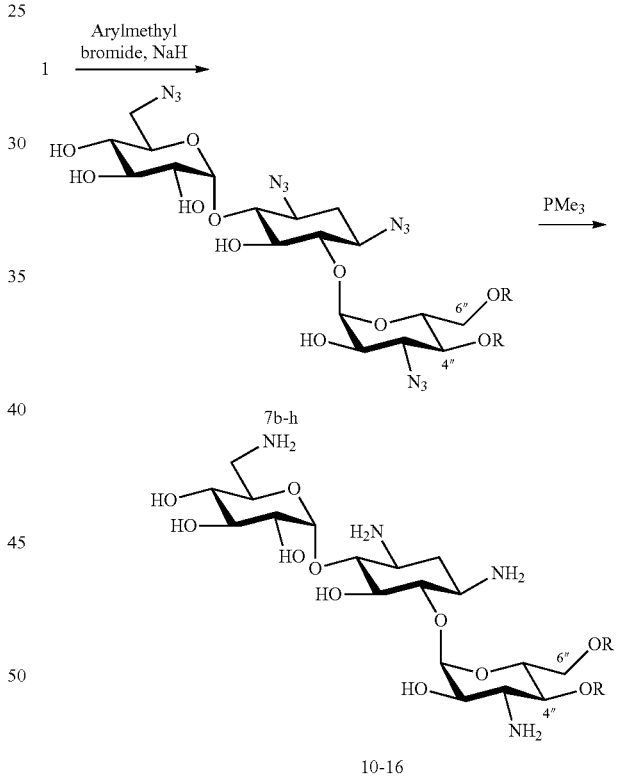

Scheme 2.

Applicable R groups are listed in the following table:

| R | Compound | Yield (%) | Compound | Yield (%) |
|---|---|---|---|---|
| (4-methoxybenzyl) | 7b | 32 | 10 | 54 |

-continued

| R | Compound | Yield (%) | Compound | Yield (%) |
|---|---|---|---|---|
| 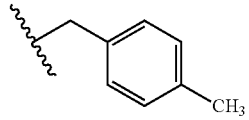 | 7c | 35 | 11 | 88 |
| 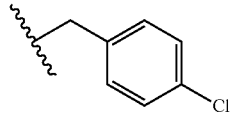 [SMILES: *Cc1ccc(Cl)cc1] | 7d | 41 | 12 | 58 |
| 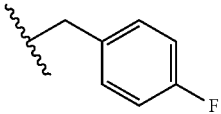 [SMILES: *Cc1ccc(F)cc1] | 7e | 37 | 13 | 71 |
| 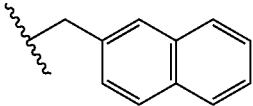 [SMILES: *Cc1ccc2ccccc2c1] | 7f | 41 | 14 | 72 |
| 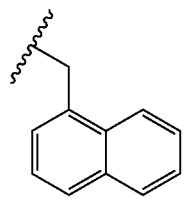 [SMILES: *Cc1cccc2ccccc12] | 7g | 43 | 15 | 42 |
| 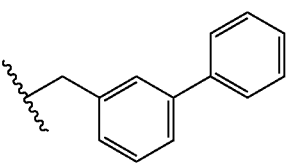 [SMILES: *Cc1cccc(-c2ccccc2)c1] | 7h | 26 | 16 | 74 |

TABLE 2

Inhibition of Cx26 by synthetic AGs

| Entry | Compound | IC$_{50}$ (μM) |
|---|---|---|
| 1 | 10 | 13.0 ± 0.7 |
| 2 | 11 | 4.3 ± 0.4 |
| 3 | 12 | 2.5 ± 0.6 |
| 4 | 13 | 8.1 ± 0.5 |
| 5 | 14 | 4.9 ± 0.2 |
| 6 | 15 | 6.6 ± 0.5 |
| 7 | 16 | 6.2 ± 0.7 |

Figure 4:
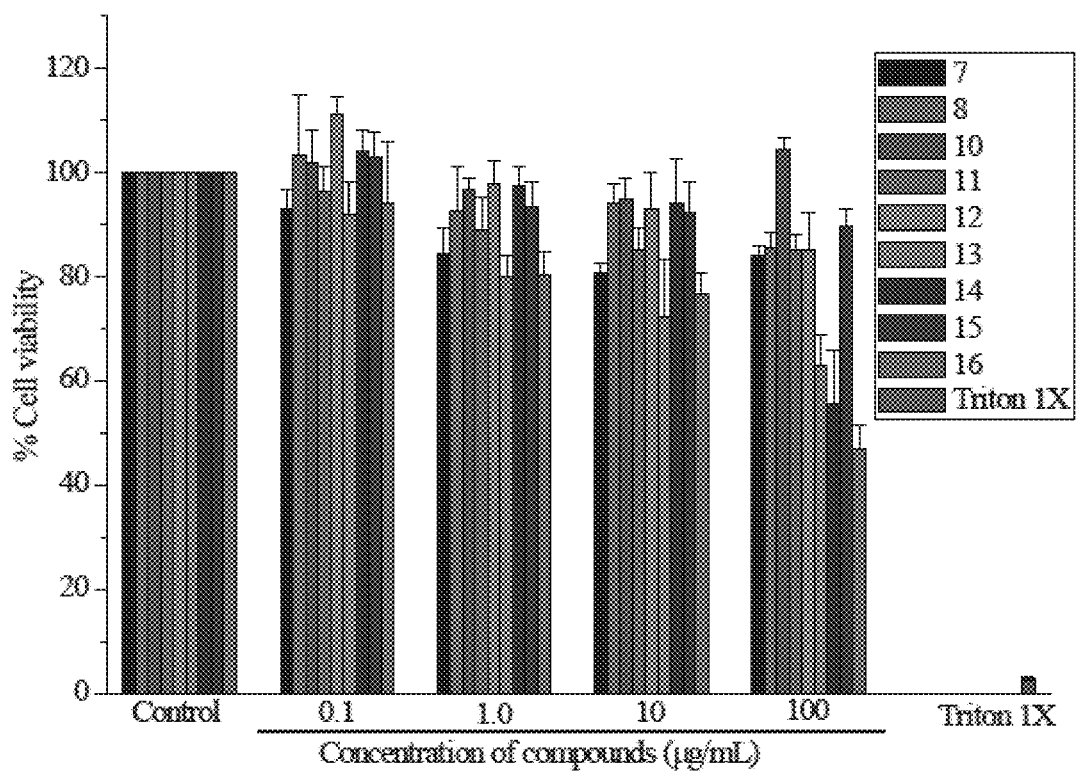
FIG. 4. Cytotoxicity of amphiphilic kanamycin derivatives assayed in mammalian HeLa cells.

All of the kanamycin derivatives were examined for their antibacterial activity against *E. coli* (ATCC 25922) and *Staphylococcus aureus* (ATCC25923), and their minimum inhibitory concentrations (MICs) were determined. Except for compounds 15 and 16, which have MICs of 64 and 16 mg/mL against *S. aureus*, respectively, the derivatives did not show significant antibacterial activity, with MICs ranging from 128 to >256 mg/mL against both bacteria. The cytotoxicity of the newly synthesized di-substituted kanamycin derivatives on HeLa cells was also examined (FIG. 4). Compounds 13, 14, and 16 showed moderate cytotoxicity (40-60% reduction of cell viability) at 100 mg/mL, which is at least 10-fold higher than the corresponding IC50 for Cx26 HC inhibition. No significant reduction of cell viability was observed for rest of the compounds at concentrations up to 100 mg/mL. The low cytotoxicity is advantageous for potential uses as therapeutics. FIG. 4 is a graph that shows the cytotoxicity of amphiphilic kanamycin derivatives.

The present inventors have discovered a new application for amphiphilic kanamycin derivatives as connexin HC inhibitors. These amphiphilic kanamycin derivatives represent a novel class of HC inhibitors that have the advantages of abolishing antibacterial activity and manifesting low cytotoxicity. We have identified the preferred structural motifs for improving HC inhibitory activity. Development of suitable connexin HC inhibitors may pave the way for better understanding the mechanism of HC inhibition and the role of connexin HCs in human disorders.

Effects on Cx43-dependent growth of the compounds.

TABLE 1

Inhibition of Cx43-dependent growth complementation by kanamycin derivatives. $IC_{50}$ and Imax (maximal inhibition) values were calculated from fittings of the Hill's equation to the data. Data are presented as means ± SEM, calculated from triplicate averages of the "n" number of independent experiments except for the cases where n = 1.

| | | Cx43 | | |
|---|---|---|---|---|
| | Compound | $IC_{50}$ (µM) | $I_{max}$ (%) | n |
| 10 | K46B09 | 4.1 ± 1.5 | 36.4 ± 13 | 2 |
| 12 | K46B10 | 20.3 | 133 | 1 |
| 13 | K46B04 | 26.6 ± 7.8 | 110 ± 33 | 3 |
| 15 | K46B11 | 15 | 122 | 1 |
| | K30 | 8.9 | 89.4 | 1 |

Compound 10 (K46B09) has a very low efficiency ($I_{max} \ll 80\%$) compared to all others tested so far, and it is therefore a parent compound to develop inhibitors selective for Cx26 hemichannels. The $IC_{50}$ for inhibition of Cx43-dependent growth by compounds 12, 13 and 15 is higher than that for Cx26 inhibition.

The compounds that have a similar $IC_{50}$ value for Cx43 and Cx26 are 5 (K4608), 11 (K46BPMe) and 16 (K46B07).

TABLE 2

Inhibition of Cx26- and Cx43-dependent growth.

| | | Cx26 | | | Cx43 | | |
|---|---|---|---|---|---|---|---|
| | Compound | $IC_{50}$ (µM) | $I_{max}$ (%) | n | $IC_{50}$ (µM) | $I_{max}$ (%) | n |
| 5 | K4608 | 13.5 ± 0.5 | 94 ± 2 | 3 | 11.4 ± 4.3 | 119 ± 8 | 3 |
| 11 | K46BPMe | 4.3 ± 0.4 | 102 ± 3 | 3 | 3.1 ± 0.9 | 80.4 ± 6 | 5 |
| 16 | K46B07 | 6.2 ± 0.7 | 102 ± 2 | 3 | 5.5 ± 2 | 121 ± 25 | 2 |

Figure 5A:
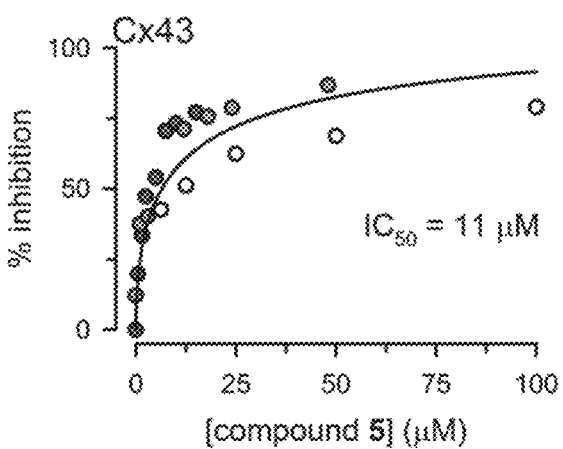
FIGS. 5A and 5B show the concentration dependence on the effect of compounds 5 and 11 on Cx43-dependent growth.
Figure 5B:
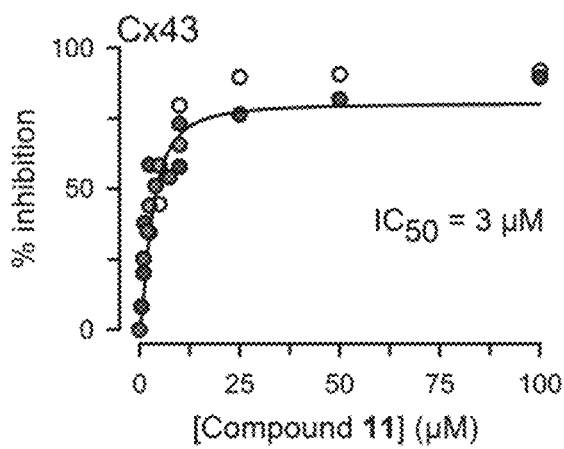

FIGS. 5A and 5B show the concentration dependence on the effect of compounds 5 and 11 on Cx43-dependent growth.

Figure 6A:
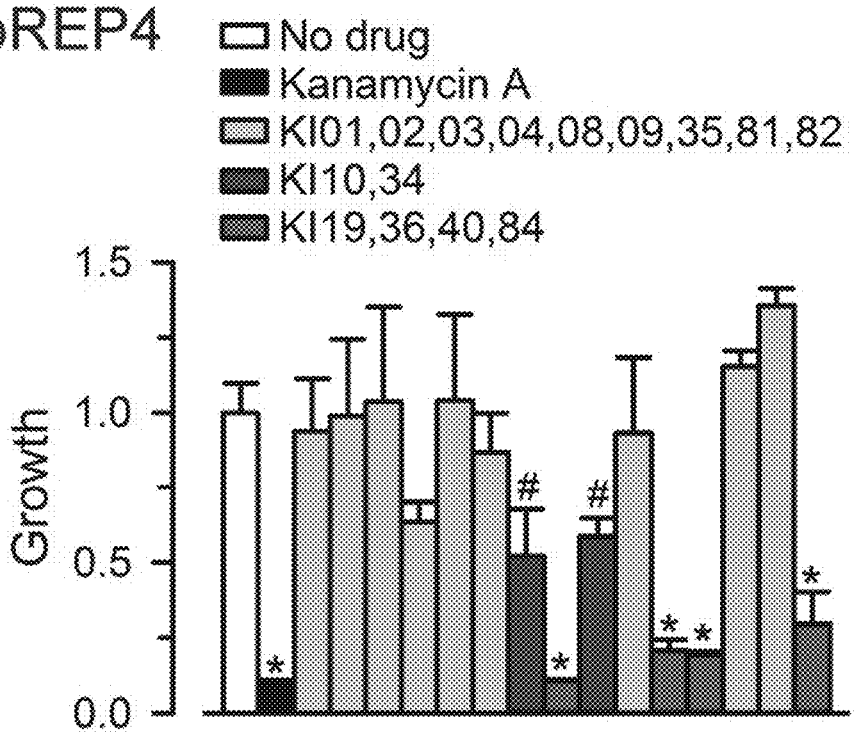
FIGS. 6A and 6B show.
Figure 6B:
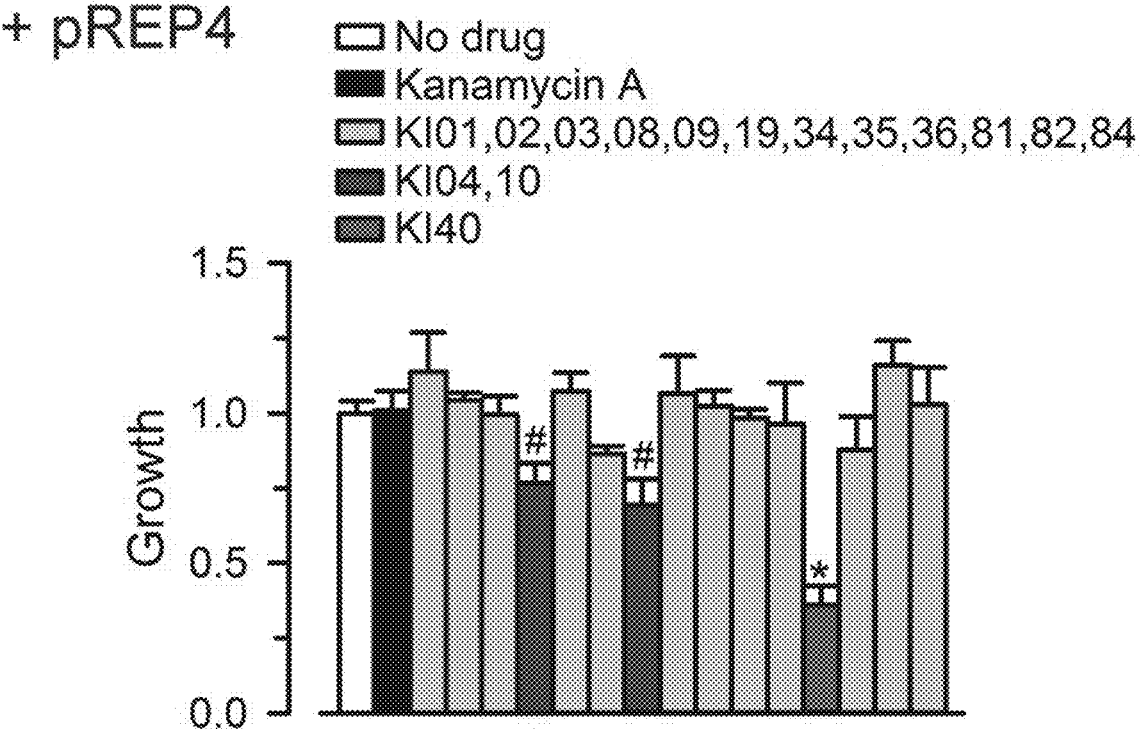

FIGS. 6A and 6B show: FIG. 6A is a No-pREP that corresponds to the evaluation of the antibiotic effect of the compounds in kanamycin-sensitive LB2003 cells grown in high-K+ medium. +FIG. 6B shows pREP corresponds to the cytotoxic effect of the compounds in kanamycin-resistant LB2003 cells grown in high-K+ medium. The data were normalized to the growth in the absence of drugs, and # and * denote P<0.05 and P<0.01 vs. growth in the absence of drugs, respectively.

To determine inhibition of connexin hemichannels by the new compounds the inventors evaluated the effects at 15 and 50 µM. These concentrations correspond to the $IC_{50}$s for inhibition of Cx26- and Cx43-dependent growth, respectively. The purpose was to select for compounds that are at least as good as previous ones, and then determine the values of $IC_{50}$ and $I_{max}$ of promising compounds, emphasizing those that show improvements for potency against Cx43.

TABLE 3

Percentage of inhibition of Cx26- and Cx43-dependent growth complementation. Data are means ± SEM calculated from triplicate averages of 3 independent experiments.

| | Cx26% inhibition | | Cx243% inhibition | |
|---|---|---|---|---|
| | 15 µM | 50 µM | 15 µM | 50 µM |
| Kanamycin A | 49.7 ± 1.6 | 77.4 ± 1.8 | 15.6 ± 1.4 | 40.4 ± 1.0 |
| KI-01 | 22.5 ± 1.9 | 34.3 ± 2.6 | 18.5 ± 0.7 | 36.0 ± 6.1 |
| KI-02 | 14.0 ± 2.1 | 25.2 ± 2.3 | 17.0 ± 5.2 | 37.2 ± 7.6 |
| KI-03 | 16.1 ± 3.2 | 33.6 ± 3.8 | 44.4 ± 5.3 | 53.5 ± 1.9 |
| KI-04 | 16.4 ± 2.3 | 56.2 ± 6.8 | | |
| KI-08 | 8.8 ± 2.0 | 22.8 ± 2.2 | 25.5 ± 7.1 | 51.0 ± 2.5 |
| KI-09 | 36.9 ± 3.9 | 79.2 ± 7.5 | | |
| KI-10 | 22.3 ± 6.9 | 79.6 ± 3.5 | 56.8 ± 8.8 | 83.4 ± 1.1 |
| K19 | 26.8 ± 1.7 | 49.2 ± 5.5 | 38.1 ± 2.8 | 51.0 ± 8.8 |
| K34 | 14.6 ± 4.3 | 69.4 ± 4.2 | 36.0 ± 3.9 | 46.7 ± 7.8 |
| K35 | 8.6 ± 2.4 | 22.6 ± 4.9 | 14.3 ± 4.3 | 30.4 ± 5.5 |
| K36 | 35.9 ± 2.9 | 62.6 ± 9.2 | 36.5 ± 0.6 | 49.3 ± 2.2 |
| K40 | 37.1 ± 13.5 | 81.0 ± 1.7 | 45.3 ± 2.7 | 55.1 ± 5.8 |
| K81 | 15.9 ± 4.2 | 36.5 ± 4.7 | 20.0 ± 7.4 | 34.8 ± 7.8 |
| K82 | 19.3 ± 2.2 | 28.2 ± 4.5 | | |
| K84 | 44.4 ± 7.0 | 69.5 ± 4.5 | | |

TABLE 4

IC$_{50}$s for inhibition of Cx26- and Cx43-dependent cell growth by promising compounds. IC$_{50}$ and Imax were calculated from fittings of the Hill's equation to the data. Data are presented as means ± SEM calculated from triplicate averages of 3 independent experiments.

| Compound | Cx26 | | Cx43 | |
|---|---|---|---|---|
| KI-04 | 66.7 ± 6.9 | 118.0 ± 7.6 | 9.7 ± 1.8 | 82.2 ± 5.9 |
| KI-09 | 18.6 ± 2.1 | 95.3 ± 3.5 | 8.6 ± 3.0 | 80.2 ± 7.0 |
| K82 | | | 7.1 ± 1.4 | 91.1 ± 11.5 |
| K84 | 17.2 ± 3.2 | 95.9 ± 10.9 | 8.9 ± 1.6 | 80.6 ± 6.0 |

Figure 7A:
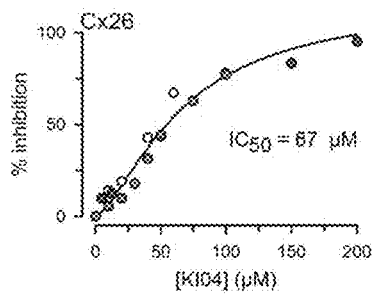
FIGS. 7A to 7C show the concentration dependence on the effect of compounds KI04, KI09 and KI84 on Cx26-dependent growth, respectively.
Figure 7B:
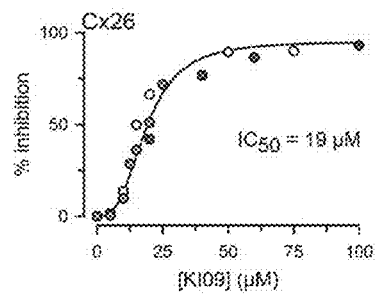
Figure 7C:
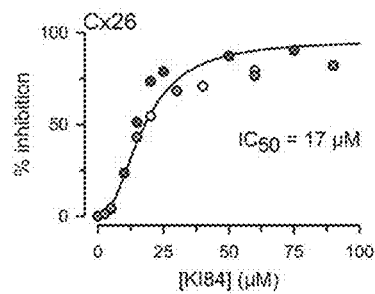
Figure 8A:
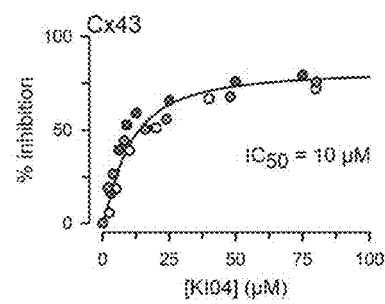
FIGS. 8A to 8E show the Concentration dependence on the effect of compounds KI04, KI09, KI10, KI82 and KI84 on Cx43-dependent growth, respectively.
Figure 8B:
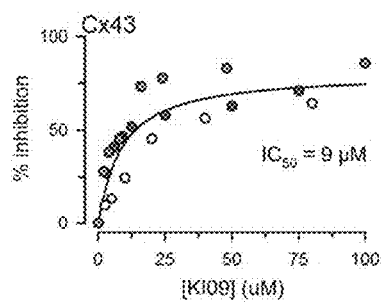
Figure 8C:
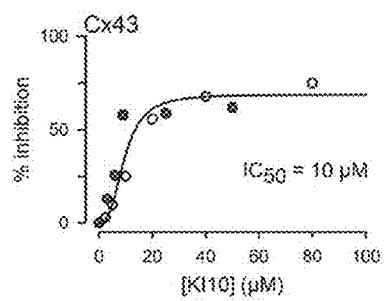
Figure 8D:
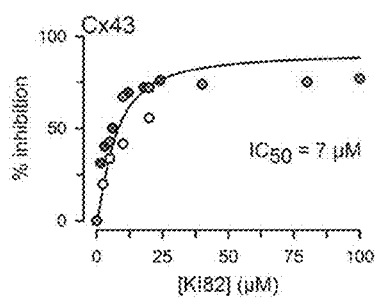
Figure 8E:
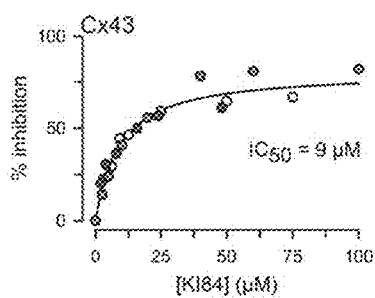
Figure 9:
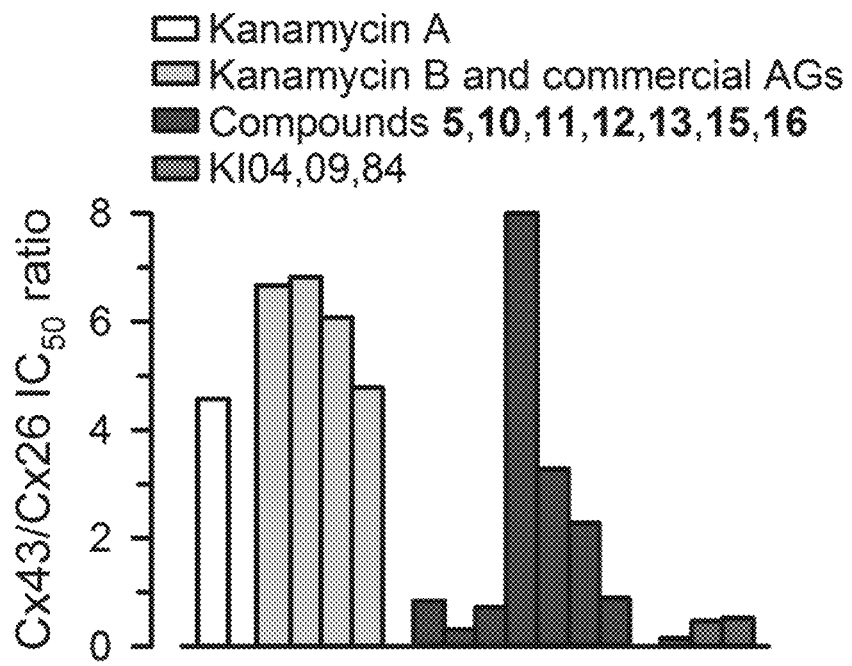
FIG. 9 shows the selectivity of Cx26 vs Cx43. Data are the ratios of IC50 values for inhibition of Cx26/Cx43 growth dependence.

FIGS. 7A to 7C show the concentration dependence on the effect of compounds KI04, KI09 and KI84 on Cx26-dependent growth, respectively. FIGS. 8A to 8E show the Concentration dependence on the effect of compounds KI04, KI09, KI10, KI82 and KI84 on Cx43-dependent growth, respectively. FIG. 9 shows the selectivity of Cx26 vs Cx43. Data are the ratios of IC50 values for inhibition of Cx26/Cx43 growth dependence.

Example 2

Some of the compounds displayed a reduced selectivity for inhibition of Cx26 compared to Cx43, mostly as a result of an improvement in potency for Cx43 inhibition, since potency for inhibition of Cx26 is about the same as the parent compound 7, and the same or lower than that of kanamycin A. It was found that the KI set compounds have higher potency for inhibition of Cx43 and show less potency for Cx26 inhibition than kanamycin A.

Chemicals were used directly from commercial sources without further purification. DMF was dried over molecular sieves (Fisher scientific, Grade 514). $^1$H NMR, $^{13}$C NMR, and $^1$H-$^1$H COSY spectra were acquired using JEOL300 (300 MHz) and Bruker Ascend (500 MHz) spectrometers at room temperature. A Shimadzu Prominence-i 2030C 3D LC system with an Agilent Zorbax RX-C18 5 μm 4.6×250 mm column was used for HPLC analysis of the compounds to confirm their purity.

Antibacterial assay: The minimum inhibitory concentration (MIC) of the newly synthesized compounds was tested against *E. coli* (ATCC 25922) and *Staphylococcus aureus* (ATCC25923). The concentration of bacteria grown in Lysogeny Broth (LB) was adjusted to an absorbance at 600 nm (OD600) of 0.08-0.1 using LB. A series of 2-fold dilutions was made for each compound in 96-well plates (USA Scientific CC7682-7596) starting from 256 μg/mL, and then, 50 μL of the diluted bacteria suspension was transferred to the wells. Bacteria were incubated for 18-24 h at 35° C. before measuring OD600 to assess growth. Experiments for each compound were done at least in duplicates.

Connexin inhibition assay: The inventors found that functional human Cx26 HCs can be expressed in *E. coli*, and have developed and optimized a growth-complementation assay to assess HC function using LB2003 as host[1,2]. LB2003 cells generously provided by Dr. E. P. Bakker (Osnabruk University, Osnabruk, Germany) were transformed with the plasmid pQE-Cx26 (human Cx26 into pQE60) and pREP4. The plasmid pQE60 confers resistance to ampicillin, and pREP4 confers resistance to kanamycin and its derivatives. LB2003 cells cannot grow in low-[K$^+$] media because of insufficient K$^+$ uptake for growth due to the knockout of three key K$^+$ transporters (Atrk, Akup, Akdp strain)[2-4]. Details and validation of the growth complementation assay have been published recently[2]. In brief, competent LB2003 containing the pREP4 plasmid were transformed with pQE-Cx26. These cells were grown overnight in Luria-Bertani medium (BD, Franklin Lakes, NJ, USA) supplemented with 100 mM KCl (to allow growth) and 0.4 mg/mL ampicillin, and then washed four times with NLM (see below), to remove residual K$^+$ from the Luria-Bertani medium. The washed cells were resuspended in complementation growth medium to an OD600 of 0.2. NLM contained 46 mM Na$_2$HPO$_4$, 23 mM NaH$_2$PO$_4$, 8 mM (NH$_4$)$_2$SO$_4$, 0.4 mM MgSO$_4$, 0.012 mM FeSO$_4$, 1 mM sodium citrate, 44 mM glucose and 0.006 mM thiamine hydrochloride, pH 7.0. KLM had the same composition that NLM except for the equimolar replacement of Na$^+$ with K$^+$. For growth complementation we used NLM+4 mM KCl, and Cx26 expression was induced with 0.5 mM IPTG at the time of dilution to OD$_{600}$=0.2. For the assay, the cells were seeded in 96-well plates and were incubated at 30° C., with shaking at 500 rpm. OD$_{600}$ was measured after 18-h incubation in a plate reader. The initial OD$_{600}$=0.2 was subtracted for growth calculations. Data are presented as means±SEM. Statistically significant differences were calculated by the Student t-test for unpaired data. Data were obtained from at least 3 independent experiments, with 3 repeats per experiment.

Cytotoxicity assay: Cytotoxicity assays in HeLa cells were performed as described (5).

General procedure for O-Alkylation of 1,3,6',3''-tetraazidokanamycin A. 0.5 g of tetraazidokanamycin A was dissolved in 20 mL of dry DMF and a catalytic amount of tetrabutylammonium iodide (TBAI) was added. Then, 10 equivalents of NaH were added and the mixture was stirred for 15 min. After that, 1.5 equivalents of arylmethyl bromide was added and the reaction mixture was stirred overnight at room temperature. TLC (100% ethyl acetate elution) was used to confirm the completion of the reaction. The reaction was quenched by adding 5 mL of methanol, and the reaction mixture was concentrated and subjected to column chromatography (30:70 ethyl acetate:hexanes to 0:100). Three yellowish sticky oil products were identified, but unfortunately two of them were in an inseparable mixture.

General procedure for acetylation. 8 equivalents of Ac$_2$O and 16 equivalents of Et$_3$N were added to 0.02 g of the 4'',6''-Di-O alkylated tetraazidokanamycin dissolved in 20 mL of anhydrous DCM, along with a catalytic amount of DMAP. The reaction mixture was stirred overnight at room temperature. After completion of the reaction, monitored by TLC, solvent was removed by compressed air. The residue obtained was purified by flash column using 100% DCM. This procedure is employed to allow $^1$H-$^1$H COSY experiments to confirm the sites of alkylation (6). The acylated adducts are not included in the manuscript, but can be found in this document.

General procedure for Staudinger reaction and preparation of final compounds. Azide groups in alkyl substituted tetraazidokanamycin were reduced to amine by Staudinger reaction (6).

Example 3

From the assay of commercially available AGs, Cx26 HC inhibition is favored, with Cx43/Cx26 selectivities ≤0.2 (Table 4). Kanamycin A can be produced by fermentation, but it is considered no longer useful in clinical settings due to the rampage of drug-resistant bacteria. Since there are stockpiles of kanamycin worldwide with little use that are accessible at low cost, and AKs display low cytotoxicity, the inventors used kanamycin as the starting material to explore AKs as connexin HC inhibitors. The immediate objectives were to demonstrate: 1) effective and isoform selective inhibition of connexin HCs (e.g., Cx43 vs. Cx26); 2) easily accessible structural variation; and 3) low cytotoxicity toward mammalian cells.

TABLE 4

IC50 values of aminoglycosides for the inhibition of Cx26 and Cx43 HCs.

| Aminoglycoside | Cx26 IC$_{50}$ (µM) | Cx43 IC$_{50}$ (µM) | Cx43/Cx26 Selectivity[a] |
|---|---|---|---|
| G418 | 0.44 ± 0.06 | 3.0 ± 0.8 | 0.20 |
| Kanamycin A | 11.5 ± 1.8 | 48.0 ± 2 | 0.24 |
| Kanamycin B | 3.6 ± 0.9 | 24 ± 2 | 0.15 |
| Neomycin | 7.4 ± 1.3 | 45 ± 9 | 0.16 |
| Paromomycin | 42 ± 9 | 201 ± 17 | 0.21 |
| Ribostamycin | >100 | >200 | ND |

[a]The Cx43/Cx26 slectivity was calculated as IC$_{50}$ Cx26/IC$_{50}$ Cx43. Adapted from ref. 1.

Tuning the Connexin Inhibitory Selectivity of Amphiphilic Kanamycins.

Figure 10:
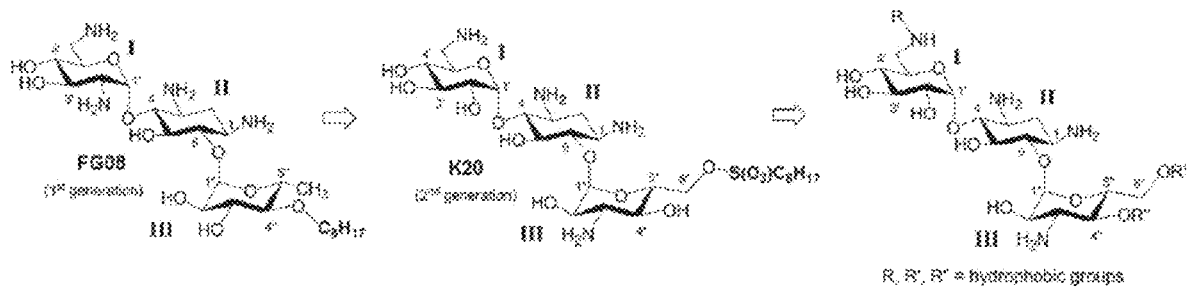
FIG. 10 shows a synthetic scheme for the development of amphiphilic kanamycins.
Figure 11:
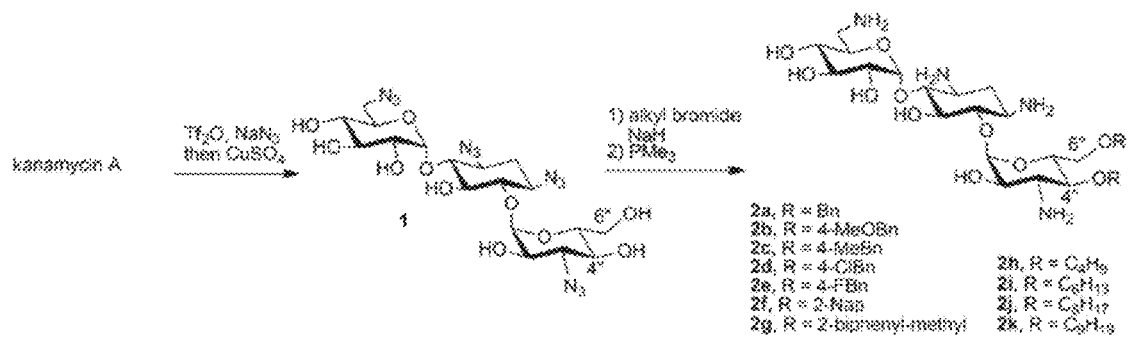
FIG. 11 shows a synthesis scheme of 4",6"-disubstituted AKs.

As described hereinabove, selective inhibition of connexin HCs of interest is desired. To demonstate the use of AKs as HC inhibitors, the inventors tested kanamycin derivatives bearing 4",6" diarylmethyl or dialkyl substitutions (FIG. 11) from a library synthesized in our laboratory to develop antifungal agents following the FG08 and K20 leads (FIG. 10). The synthesis of these AKs was based on a direct modification strategy. Using the reported regioselective protocol and kanamycin A as the starting material (FIG. 2) [2-3] the AG was first converted into tetraazidomycin (FIG. 11, compound 1), followed with a regioselective alkylation and azide reduction to yield the desired AKs (FIG. 11, compounds 2a-k).

These AKs were assayed against HCs using the E. coli-based method mentioned previously. The results identified compound 2b as the most selective toward Cx43, with a Cx43/Cx26 selectivity of 3.2, whereas compound 2d was the most selective toward Cx26, with a selectivity of 0.15 (Table 5). Compound 2d was more potent on Cx26 HCs than the parent compound kanamycin A. From these results, it appears that electron-rich or non-polar aromatic moieties such as those in compounds 2b, 2c, 2f, and 2g favor selectivity toward Cx43, while electron-deficient or halogenated aromatic moieties favor selectivity toward Cx26.

Since none of these AKs manifest significant cytotoxicity [3], this proves the use of AKs as connexin HC inhibitors.

Figure 12:
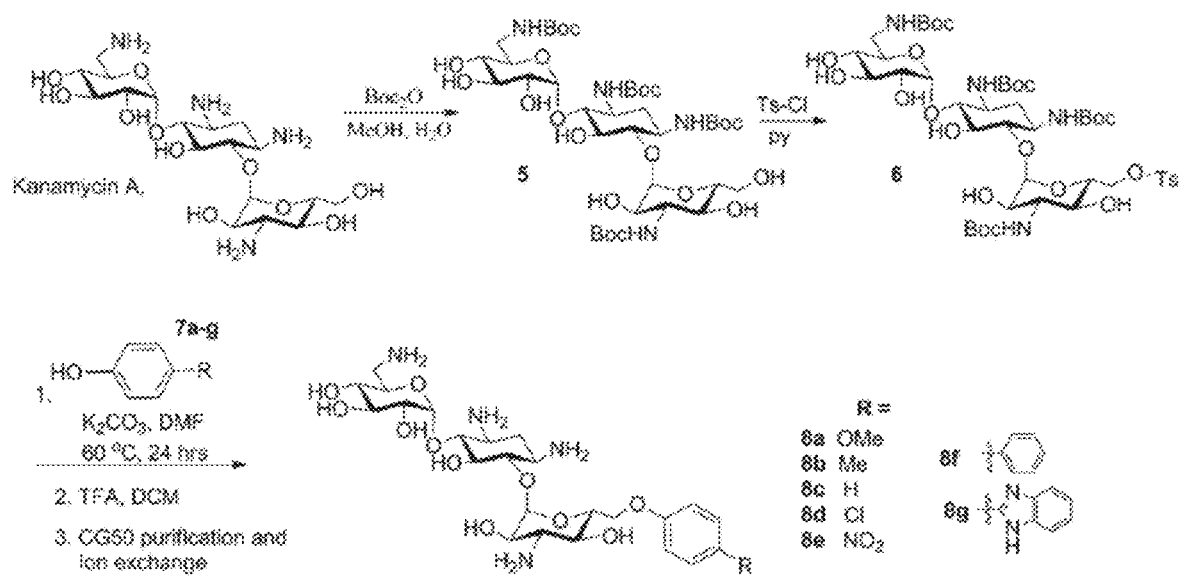
FIG. 12 shows the synthesis of 6"-modified kanamycin derivatives.
Figure 13:
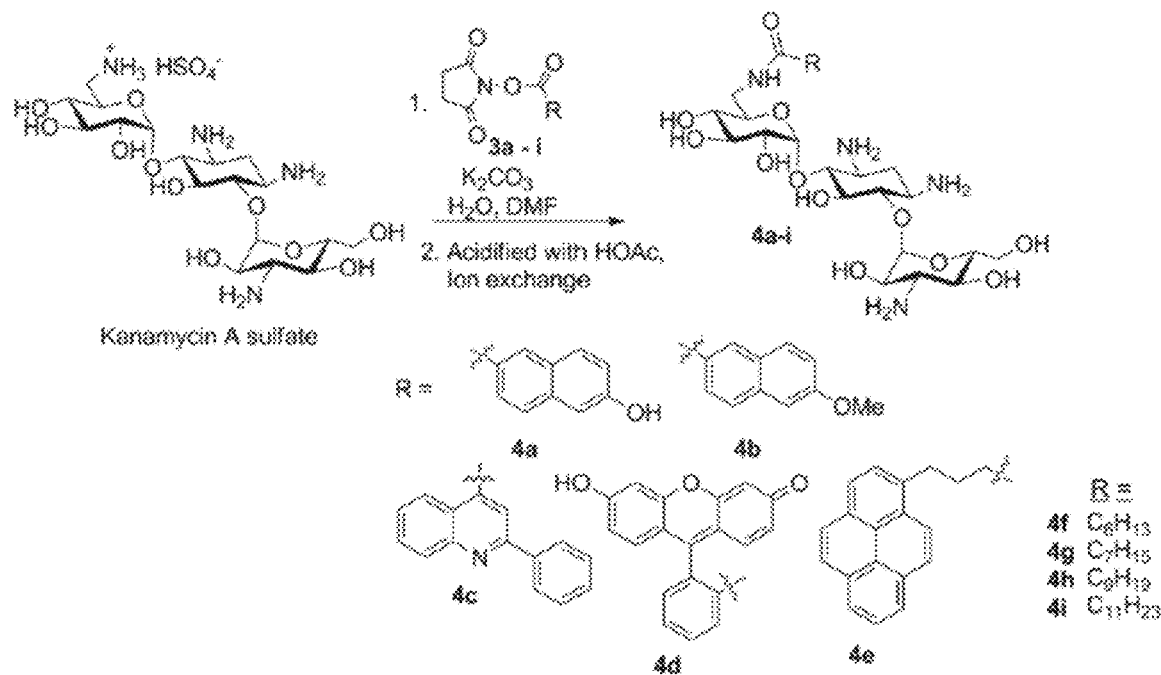
FIG. 13 shows the synthesis of 6'-modified kanamycin derivatives.

A simple and inexpensive method for the synthesis of 6"- and 6'-modified AKs with diverse structural variations developed by the present inventors was used[4-6]. These AKs also have a kanamycin core, but unlike 4",6" disubstituted kanamycins, they have a hydrophobic group attached to either 6" or 6' positions. The synthesis of these derivatives can be accomplished using kanamycin A directly or Boc-protected kanamycin, which can be prepared from kanamycin A in a hundred grams scale. The synthesis of 6"-modified AKs began with the Boc-protection of kanamycin A (FIG. 12). Following the tosylation, nucleophilic substitution of compound 6 using aryl alcohols (8a-g) allowed the introduction of the hydrophobic group at the 6" position. The synthesis of 6'-modified AKs can be accomplished in a one-step process (FIG. 13).

TABLE 5

IC$_{50}$ values of 4",6"-disubstituted AKs for the inhibition of Cx26 and Cx43 HCs.

| Compound | Cx26 IC$_{50}$ (µM) | Cx43 IC$_{50}$ (µM) | Cx43/Cx26 Selectivity[a] |
|---|---|---|---|
| 1 | >100 | >100 | ND |
| 2a | 7.6 ± 1.2 | ND[b] | ND |
| 2b | 13.0 ± 0.7 | 4.1 ± 1.5 | 3.17 |
| 2c | 4.3 ± 0.4 | 3.1 ± 0.9 | 1.39 |
| 2d | 2.5 ± 0.6 | 17.1 ± 1.7 | 0.15 |
| 2e | 8.1 ± 0.5 | 26.6 ± 7.8 | 0.30 |
| 2f | 4.9 ± 0.2 | 6.2 ± 4.4 | 1.07 |
| 2g | 6.6 ± 0.7 | 5.5 ± 2.0 | 1.23 |
| 2h | 19.0 ± 2.0 | ND | ND |
| 2i | 6.2 ± 1.4 | ND | ND |
| 2j | 13.6 ± 0.5 | 11.4 ± 4.3 | 1.19 |
| 2k | 18.8 ± 1.3 | ND | ND |

[a]The Cx43/Cx26 selectivity was calculated as IC$_{50}$ Cx26/IC$_{50}$ Cx43;
[b]Not determined. Adapted from refs. 5 and 7.

Since commercially available AGs manifest higher inhibitory potency toward Cx26, the focus of these 6'- and 6"-modified AKs was to reverse the isoform selectivity of the parent kanamycin A to produce compounds that display better Cx43/Cx26 selectivity. To expedite the initial screening, the new AKs were tested at two concentrations, 15 and 50 µM, as these approximate the IC$_{50}$ values for inhibition by kanamycin A of HCs formed by Cx26 (~10 µM) and Cx43 HCs (~50 µM) (Table 6)[1]. Then, IC$_{50}$ values were determined (Table 7) for the compounds that exerted >50% inhibition of Cx43 HCs at 15 µM (Table 6; shaded=8b, 8d, 8g, 4d, 4e, 4i).

TABLE 6

Inhibition of Cx26 and Cx43 HCs by 6"-and 6'-modified AKs (%).

| Type of modification | Compound | Cx26 (% inhibition) | | Cx34 (% inhibition) | | cLogD |
|---|---|---|---|---|---|---|
| | | 15 µM | 50 µM | 15 µM | 50 µM | (pH = 7) |
| 6"-modified | 8a | 15.9 ± 4.2 | 36.5 ± 4.7 | 20.0 ± 7.4 | 34.8 ± 7.8 | −12.52 |
| | 8b | 19.3 ± 2.2 | 28.2 ± 4.5 | 63.8 ± 6.8 | 76.8 ± 5.8 | −11.80 |
| | 8c | 14.6 ± 4.3 | 69.4 ± 4.2 | 36.0 ± 3.9 | 46.7 ± 7.8 | −12.27 |
| | 8d | 44.4 ± 7.0 | 69.5 ± 4.5 | 50.3 ± 1.0 | 68.3 ± 4.6 | −11.75 |
| | 8e | 35.9 ± 2.9 | 62.6 ± 9.2 | 36.5 ± 0.6 | 49.3 ± 2.2 | −12.31 |
| | 8f | 46.3 ± 8.6 | 67.8 ± 6.0 | 27.3 ± 4.1 | 54.3 ± 8.9 | −10.58 |
| | 8g | 83.1 ± 2.1 | 85.5 ± 1.7 | 43.2 ± 7.3 | 71.7 ± 3.5 | −10.88 |
| 6'-modified | 4a | 4.7 ± 1.6 | 32.8 ± 11.1 | 34.1 ± 6.0 | 37.1 ± 7.4 | −10.27 |
| | 4b | 15.1 ± 4.9 | 27.9 ± 2.6 | 42.1 ± 1.5 | 45.1 ± 1.5 | −10.24 |
| | 4c | 8.0 ± 2.0 | 22.8 ± 2.2 | 25.5 ± 7.1 | 51.0 ± 2.5 | −8.81 |
| | 4d | 22.3 ± 6.9 | 79.6 ± 3.5 | 56.8 ± 8.8 | 83.4 ± 1.1 | −8.97 |

TABLE 6-continued

Inhibition of Cx26 and Cx43 HCs by 6"-and 6'-modified AKs (%).

| Type of modification | Compound | Cx26 (% inhibition) 15 µM | 50 µM | Cx34 (% inhibition) 15 µM | 50 µM | cLogD (pH = 7) |
|---|---|---|---|---|---|---|
| | 4e | 36.9 ± 3.9 | 79.2 ± 7.5 | 52.2 ± 8.8 | 69.6 ± 7.5 | −7.75 |
| | 4f | 22.5 ± 1.9 | 34.3 ± 2.6 | 18.5 ± 0.7 | 36.0 ± 6.1 | −10.90 |
| | 4g | 14.0 ± 2.1 | 25.2 ± 2.3 | 17.0 ± 5.2 | 37.2 ± 7.6 | −10.11 |
| | 4h | 16.1 ± 3.2 | 33.6 ± 3.8 | 44.4 ± 5.3 | 53.5 ± 1.9 | −9.31 |
| | 4i | 16.4 ± 2.3 | 56.2 ± 6.8 | 53.6 ± 4.6 | 70.9 ± 2.3 | −8.52 |

[a] The Cx43/Cx26 selectivity was calculated as $IC_{50}$ Cx26/$IC_{50}$ Cx43. 8b, 8d, 8g, 4d, 4e and 4i: compounds selected for further analysis (Table 4). Modified from ref. 7.

TABLE 7

$IC_{50}$ of selected 6"- and 6'-modified AKs toward Cx26 and Cx43 HCs.

| AK class | Compound | Cx26 $IC_{50}$ (µM) | Cx43 $IC_{50}$ (µM) | Cx43/Cx26 Selectivity[a] |
|---|---|---|---|---|
| 6"-modified | 8b | 49.4 ± 9.3 | 6.2 ± 1.4 | 7.97 |
| | 8d | 17.2 ± 3.2 | 8.9 ± 1.6 | 1.93 |
| | 8g | 6.0 ± 1.2 | 17.7 ± 5.6 | 0.34 |
| 6"-modified | 4d | 12.7 ± 2.2 | 8.9 ± 3.7 | 1.42 |
| | 4e | 18.6 ± 2.1 | 8.6 ± 1.0 | 2,16 |
| | 4i | 66.7 ± 6.9 | 9.7 ± 1.8 | 6.88 |
| Kanamycin: A | | 11.5 ± 1.8 | 48.0 ± 2.0 | 0.24 |

[a] The Cx43/Cx26 selectivity was calculated as $IC_{50}$ Cx26/$IC_{50}$ Cx43. Modified from ref 7.

The results revealed that 4i and 8b were most selective toward Cx43, with calculated selectivities (Cx26 $IC_{50}$/Cx43 $IC_{50}$) of ~7 and ~8, respectively. These selectivities are ~30-fold higher than that of kanamycin A (0.24) and >2-fold higher than the lead from the 4",6" disubstituted kanamycin 2b (~3). None of the selected 6"- or 6'-modified AKs selected were cytotoxic to HeLa cells at 100 µM. These results demonstrate how to tune the selectivity of AKs from Cx26 to Cx43 HCs.

The results revealed that 4i and 8b were most selective toward Cx43, with calculated selectivities (Cx26 $IC_{50}$/Cx43 $IC_{50}$) of ~7 and ~8, respectively. These selectivities are ~30-fold higher than that of kanamycin A (0.24) and >2-fold higher than the lead from the 4",6" disubstituted kanamycin 2b (~3). None of the selected 6"- or 6'-modified AKs selected were cytotoxic to HeLa cells at 100 µM. These results prove the feasibility of tuning the selectivity of AKs from Cx26 to Cx43 HCs.

Structure Activity Relationship of the Connexin HC Inhibitory Activity of Amphiphilic Kanamycins.

Figures 14A, 14B:
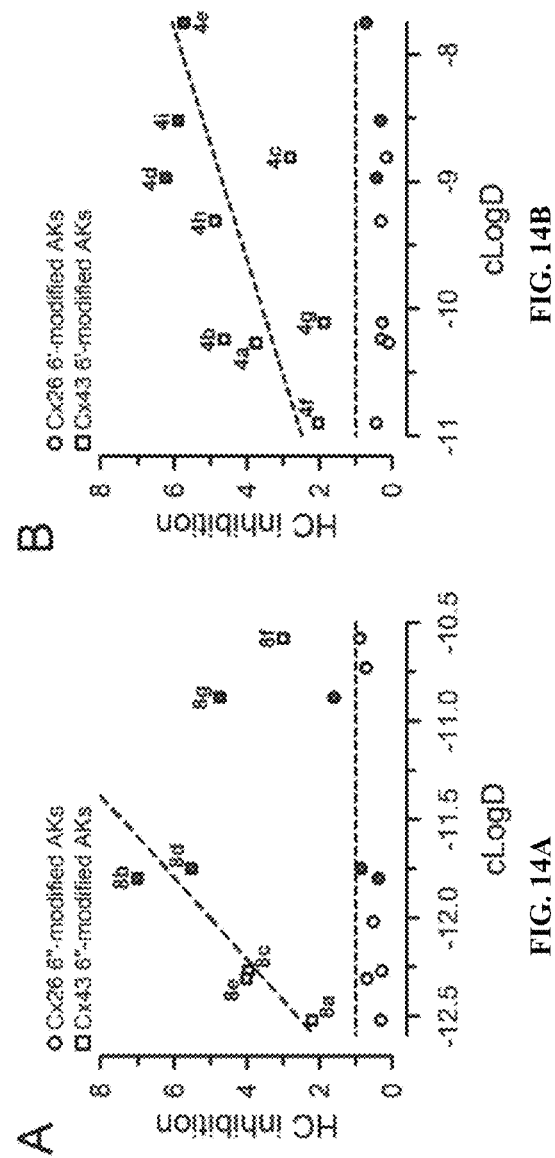
FIGS. 14A and 14B show the correlation between the inhibition of HC-dependent growth complementation by AKs and their cLogD. The values corresponding to the compounds in Table 4 are shown in filled circles.

Since the site of modifications and the type of hydrophobic groups attached to AKs vary drastically, a clear structure activity relationship (SAR) is difficult to delineate at this point. However, a feature of the AKs is the presence of hydrophobic groups that attenuate the overall solubility of the amphiphilic compounds in aqueous media. Therefore, a rather straightforward approach is to compare the commonly employed pharmacokinetic parameter cLogD with the biological activity; cLogD is the calculated log of the 1-octanol/water partition coefficient, with higher numbers corresponding to more hydrophobic compounds (less hydrophilic AKs; less negative cLogD values). The cLogD of the 6"- and 6'-modified AKs were calculated and correlated with the percentage of inhibition normalized to the effects of the parent compound kanamycin A (FIGS. 14A and 14B). An exciting and distinct observation was the increase in potency of Cx43 HC inhibition (squares) as the AKs cLogD increased, except for the 6"-modified compounds 8g and 8h, whereas the Cx26 HC inhibitory potency (circles) did not show correlation with cLogD. These observations demonstrate a strategy for increasing the Cx43/Cx26 selectivity by attaching hydrophobic groups to increase cLogD. Detailed analysis revealed that the 6"-modified AKs (FIG. 14A) showed increased Cx43 HC inhibitory potency of compounds with p-substituted phenyl groups (8a-e), but not for the more hydrophobic (higher cLogD) and larger compounds 8g and 8h. In the case of 6'-modified AKs the correlation between the potency for Cx43 HC inhibition and cLogD was weaker (FIG. 14B). However, different from the 6"-modified AKs, 6'-modified AKs maintained this correlation regardless of whether the hydrophobic groups attached were linear acyl groups (compounds 4f-i) or aryl moieties (compounds 4a-e). Since the synthesis of 6'-modified AKs is easier than that of the 6"-modified AKs, these AKs, especially compound 4i, may represent another option for the development of new Cx43 HC-selective inhibitors.

4",6"-Di-O-benzyl-1,3,6',3"-tetraazidokanamycin (7a). $^1$H NMR (300 MHz, Methanol-D3) δ 7.2-7.4 (m, 10H), 5.21 (d, J=3.9 Hz, 1H), 5.20 (d, J=4.2 Hz, 1H), 4.73 (d, J=10.8 Hz, 1H), 4.56 (d, J=12.0 Hz, 1H), 4.49 (d, J=10.8 Hz, 1H), 4.44 (d, J=12.0 Hz, 1H), 4.2-4.3 (m, 1H), 4.0-4.1 (m, 1H), 3.3-3.7 (m, 15H), 2.3-2.4 (m, 1H), 1.52 (ddd, J=12.3 Hz 1H). $^{13}$C NMR (75. MHz, Methanol-D3) δ 138.18 (2 Carbons), 128.24 (2 Carbons), 128.11 (2 Carbons), 128.03 (2 Carbons), 127.97 (2 Carbons), 127.60 (2 Carbons), 101.20, 98.43, 83.89, 80.05, 76.50 (2 Carbons), 74.39, 73.54, 73.18, 72.63, 72.23, 71.22, 70.81, 70.26, 68.35, 66.92, 61.09, 59.61, 51.49, 32.18. ESI/APCI calcd for $C_{32}H_{40}N_{12}O_{11}Na$ [M+Na]$^+$ m/z 791.2832; measured m/z 791.2858. Yield: 196 mg (255 mmol, 30%).

4",6"-Di-O-(4-methoxybenzyl)-1,3,6',3"-tetraazidokanamycin (7b). $^1$H NMR (500 MHz, Methanol-D3) δ 7.28 (d, J=7.7 Hz, 2H), 7.11 (d, J=7.7 Hz, 2H), 6.89 (d, J=7.4 Hz, 2H), 6.85 (d, J=7.4 Hz, 2H), 5.24 (d, J=3.8 Hz, 1H), 5.23 (d, J=3.5 Hz, 1H), 4.65 (d, J=10.4 Hz, 1H), 4.55 (d, J=11.6 Hz, 1H), 4.3-4.4 (m, 3H), 4.0-4.1 (m, 1H), 3.3-3.7 (m, 21H), 2.3-2.4 (m, 1H), 1.55 (ddd, J=12.5 Hz 1H). $^{13}$C NMR (125 MHz, Methanol-D3) δ 159.56, 159.49, 129.97, 129.81, 129.66 (2 Carbons), 129.52 (2 Carbons), 113.46 (2 Carbons), 113.25 (2 Carbons), 101.00, 98.23, 83.67, 79.95, 75.94, 74.19, 73.88, 73.37, 72.59, 72.45, 72.04, 70.96, 70.64, 70.05, 67.58, 66.72, 60.86, 59.44, 54.29, 54.27, 51.32, 31.99. ESI/APCI calcd for $C_{34}H_{44}N_{12}O_{13}Na$ [M+Na]$^+$: 851.3048 m/z; measured 851.3096 m/z. Yield: 225 mg (272 mmol, 32%).

4",6"-Di-O-(4-methylbenzyl)-1,3,6',3"-tetraazidokanamycin (7c). $^1$H NMR (300 MHz, Methanol-D3) δ 7.0-7.2 (m, 8H), 5.20 (d, J=2.7 Hz, 1H), 5.19 (d, J=3.6 Hz, 1H), 4.65 (d, J=10.8 Hz, 1H), 4.53 (d, J=12.0 Hz, 1H), 4.2-4.4 (m, 3H), 4.0-4.1 (m, 1H), 3.3-3.7 (m, 15H), 2.3-2.4 (m, 7H), 1.52

(ddd, J=12.3 Hz 1H). $^{13}$C NMR (75 MHz, Methanol-D3) δ 137.42, 137.30, 134.96, 134.85 128.75 (2 Carbons), 128.56 (2 Carbons), 128.17 (2 Carbons), 128.03 (2 Carbons), 101.07, 98.43, 83.76, 79.92, 76.15, 74.24, 74.16, 73.41, 72.87, 72.50, 72.11, 71.05, 70.67, 70.08, 66.79, 60.96, 59.49, 51.37, 32.08, 29.43, 19.92 (2 Carbons). ESI/APCI calcd for $C_{34}H_{44}N_{12}O_{11}Na$ [M+Na]$^+$: m/z 819.3145; measured m/z 819.3158. Yield: 237 mg (298 mmol, 35%).

4",6"-Di-O-(4-chlorobenzyl)-1,3,6',3"-tetraazidokanamycin (7d). $^1$H NMR (500 MHz, Methanol-D3) δ 7.3-7.4 (m, 6H), 7.2 (d, J=7.8 Hz 2H), 5.24 (d, J=3.4 Hz, 2H), 4.76 (d, J=11.3 Hz, 1H), 4.58 (d, J=12.1 Hz, 1H), 4.51 (d, J=11.1 Hz, 1H), 4.46 (d, J=12.2 Hz, 1H), 4.3-4.4 (m, 1H), 4.0-4.1 (m, 1H), 3.3-3.7 (m, 15H), 2.3-2.4 (m, 1H), 1.56 (ddd, J=12.2 Hz 1H). $^{13}$C NMR (125 MHz, Methanol-D3) δ 138.87, 138.855, 133.16, 133.11, 129.30 (2 Carbons), 129.09 (2 Carbons), 128.14 (2 Carbons), 128.01 (2 Carbons), 100.98, 98.24, 83.68, 79.90, 76.36, 74.21, 73.35, 73.19, 72.45, 72.05, 72.02, 71.08, 70.64, 69.99, 69.18, 66.64, 60.91, 59.43, 51.31, 32.01. ESI/APCI calcd for $C_{32}H_{38}Cl_2N_{12}O_{11}Na$ [M+Na]$^+$: 859.2058 m/z; measured 859.2072 m/z. Yield: 292 mg (349 mmol, 41%).

4",6"-Di-O-(4-flurobenzyl)-1,3,6',3"-tetraazidokanamycin (7e). $^1$H NMR (300 MHz, Methanol-D3) δ 7.2-7.4 (m, 4H), 6.9-7.1 (m, 4H), 5.25 (d, J=3.6 Hz, 2H), 4.71 (d, J=11.1 Hz, 1H), 4.53 (d, J=11.4 Hz, 1H), 4.4-4.5 (m, 2H), 4.3-4.4 (m, 1H), 4.0-4.1 (m, 1H), 3.3-3.7 (m, 15H), 2.3-2.4 (m, 1H), 1.52 (ddd, J=12.3 Hz 1H). $^{13}$C NMR (75 MHz, Methanol-D3) δ 162.50 (d, $J_{CF}$=243.1 Hz), 162.46 (d, $J_{CF}$=244.2 Hz), 134.12 (d, $J_{CF}$=3.0 Hz), 134.07 (d, $J_{CF}$=3.0 Hz), 129.77 (d, $J_{CF}$=8.1 Hz, 2 Carbons), 129.65 (d, $J_{CF}$=8.2 Hz, 2 Carbons), 114.72 (d, $J_{CF}$=17.6 Hz, 2 Carbons), 114.55 (d, $J_{CF}$=17.6 Hz, 2 S 5 Carbons), 101.06, 98.31, 83.74, 79.96, 76, 29, 74.27, 73.41 (2 Carbons), 72.51, 72.21, 72.12, 71.10, 70.69, 70.09, 68.14, 66.72, 60.99, 59.50, 51.37, 32.09. ESI/APCI calcd for $C_{32}H_{38}N_{12}O_{11}F_2Na$ [M+Na]$^+$: m/z 827.2643; measured m/z 827.2652. Yield: 253 mg (315 mmol, 37%).

4",6"-Di-O-(2-aphthalenemethyl)-1,3,6',3"-tetraazidokanamycin (7f). $^1$H NMR (500 MHz, Metha-nol-D3) δ 7.7-7.8 (m, 5H), 7.63 (d, J=8.4 Hz, 1H), 7.57 (d, J=7.9 Hz, 1H), 7.3-7.5 (m, 6H), 7.57 (dd, J=8.4 Hz, J=1.5 Hz, 1H), 5.26 (d, J=3.7 Hz, 1H), 5.22 (d, J=3.8 Hz, 1H), 4.8-4.9 (m, 1H), 4.75 (d, J=12.8 Hz, 1H), 4.5-4.6 (m, 2H), 4.3-4.4 (m, 1H), 4.0-4.1 (m, 1H), 3.3-3.7 (m, 15H), 2.3-2.4 (m, 1H), 1.51 (ddd, J=12.5 Hz 1H). $^{13}$C NMR (125 MHz, Methanol-D3) δ 135.35, 135.33, 133.31, 133.19, 133.17, 133.01, 127.90, 127.60, 127.56, 127.53, 127.38, 127.22, 126.76, 126.35, 125.95, 125.85, 125.72, 125.67, 125.63, 125.55, 101.00, 98.28, 83.72, 79.97, 76.19, 74.18 (2 Carbons), 73.35, 73.04, 72.43, 72.04, 71.06, 70.62, 70.08, 68.02, 66.79, 60.85, 59.40, 51.32, 31.96. ESI/APCI calcd for $C_{40}H_{44}N_{12}O_{11}Na$ [M+Na]$^+$: 891.3150 m/z; measured 891.3111 m/z. Yield: 302 mg (349 mmol, 41%).

4",6"-Di-O-(1-aphthalenemethyl)-1,3,6',3"-tetraazidokanamycin (7g). $^1$H NMR (500 MHz, Metha-nol-D3) δ 8.13 (d, J=8.3 Hz, 1H), 7.9 (d, J=7.7 Hz, 1H), 7.7-7.8 (m, 4H), 7.4-7.5 (m, 6H), 7.29 (t, J=7.5 Hz, 1H), 7.07 (d, J=6.6 Hz, 1H), 5.25 (d, J=3.3 Hz, 1H), 5.1-5.2 (m, 2H), 5.01 (d, J=12.2 Hz, 1H), 4.6-4.7 (m, 2H), 4.3-4.4 (m, 1H), 4.0-4.1 (m, 1H), 3.3-3.7 (m, 14H), 2.9 (dd, J=13.2 Hz, J=8.1 Hz, 1H), 2.3-2.4 (m, 1H), 1.52 (ddd, J=12.5 Hz 1H). $^{13}$C NMR (125 MHz, Methanol-D3) δ 133.93, 133.76, 133.45, 133.40, 131.74, 131.65, 128.43, 128.28, 128.23, 128.07, 126.53 (2 Carbons), 125.86, 125.80, 125.48, 125.32, 124.82, 124.80, 123.87, 123.71, 100.95, 98.23, 83.66, 79.83, 75.51, 74.14, 73.33, 72.40, 72.02, 71.86, 71.36, 71.23, 70.60, 70.07, 68.11, 66.95, 60.86, 59.38, 51.30, 31.95. ESI/APCI calcd for $C_{40}H_{44}N_{12}O_{11}Na$ [M+Na]$^+$: 891.3145 m/z; measured 891.3164 m/z. Yield: 318 mg (366 mmol, 43%).

4",6"-Di-O-(3-phenylbenzyl)-1,3,6',3"-tetraazidokanamycin (7h). $^1$H NMR (500 MHz, Methanol-D3) δ 7.3-7.6 (m, 17H), 7.21 (d, J=7.6 Hz, 1H), 5.26 (d, J=3.7 Hz, 1H), 5.17 (d, J=3.8 Hz, 1H), 4.83 (d, J=11.0 Hz, 1H), 4.68 (d, J=12.0 Hz, 1H), 4.61 (d, J=11.0 Hz, 1H), 4.53 (d, J=12.1 Hz, 1H), 4.3-4.4 (m, 1H), 4.0-4.1 (m, 1H), 3.3-3.7 (m, 15H), 2.3-2.4 (m, 1H), 1.51 (ddd, J=12.2 Hz 1H). $^{13}$C NMR (125 MHz, Methanol-D3) δ 141.25, 141.18, 140.85, 140.79, 138.56 (2 Carbons), 128.55, 128.46 (2 Car-bons), 128.43 (3 Carbons), 127.00, 126.96, 126.73, 126.67, 126.64 (4 Car-bons), 126.42, 126.34, 126.10, 126.06, 100.99, 98.25, 83.70, 79.87, 76.39, 74.20, 74.16, 73.34, 72.83, 72.41, 72.02, 71.04, 70.61, 70.01, 68.10, 66.77, 60.90, 59.40, 51.30, 31.98. ESI/APCI calcd for $C_{44}H_{48}N_{12}O_{11}Na$ [M+Na]$^+$ 943.3463: m/z; measured 943.3355 m/z. Yield: 204 mg (221 mmol, 26%).

5, 2', 3', 4', 2"-Penta-O-methyl-4",6"-di-O-benzyl-1,3,6',3"-tetraazidokanamycin (8a). $^1$H NMR (300 MHz, Chloroform-D) δ 7.2-7.4 (m, 10H), 5.59 (d, J=3.3 Hz, 1H), 5.43 (d, J=3.9 Hz, 1H), 4.78 (d, J=10.8 Hz, 1H), 4.64 (d, J=12.0 Hz, 1H), 4.4-4.5 (m, 2H), 4.0-4.2 (m, 2H), 3.4-3.8 (m, 28H), 3.1-3.3 (m, 2H), 2.3-2.4 (m, 1H), 1.5-1.6 (m, 1H). $^{13}$C NMR (75 MHz, Chloroform-D) δ 138.06, 137.89, 128.51 (2 Carbons), 128.39 (2 Carbons), 128.16 (2 Carbons), 128.01 (2 Carbons), 127.91, 127.83, 97.03, 95.53, 84.58, 83.51, 81.81, 80.53, 80.41, 77.83, 77.31, 76.15, 74.79, 73.63, 70.66, 70.24, 68.10, 65.19, 61.27, 61.02, 60.88, 60.71, 60.66, 59.29, 59.15, 51.33, 32.63. ESI/APCI calcd for $C_{37}H_{50}N_{12}O_{11}Na$ [M+Na]$^+$: m/z 861.3614; measured m/z 861.3640. Yield: 344 mg (410 mmol, 63%).

4",6"-Di-O-benzylkanamycin (7). $^1$H NMR (300 MHz, D$_2$O) δ 7.2-7.4 (m, 8H), 7.1-7.2 (m, 2H), 5.44 (d, J=3.9 Hz, 1H), 5.01 (d, J=3.6 Hz, 1H), 4.5-4.6 (m, 2H), 4.3-4.4 (m, 2H), 4.0-4.1 (m, 1H), 3.4 S 6-3.9 (m, 12H), 3.2-3.3 (m, 2H), 3.0-3.1 (m, 2H), 2.4-2.5 (m, 1H), 1.84 (ddd, J=12.9 Hz 1H). $^{13}$C NMR (75 MHz, D$_2$O) δ 136.68, 136.23, 128.98 (2 Carbons), 128.95 (3 Carbons), 128.89 (2 Carbons), 128.73 (2 Carbons), 128.66, 100.53, 96.31, 83.90, 78.10, 74.45, 73.33, 73.23, 72.76, 72.09, 71.01, 70.80, 68.69, 68.08, 67.49, 54.23, 49.89, 47.84, 44.75, 40.36, 27.61. ESI/APCI calcd for $C_{32}H_{49}N_4O_{11}$ m/z 665.3392; measured m/z 665.3407. Yield: 99 mg (122 mmol, 89%).

5, 2', 3', 4', 2"-Penta-O-methyl-4",6"-di-O-benzylkanamycin (8). $^1$H NMR (300 MHz, D$_2$O) δ 7.1-7.4 (m, 10H), 5.43 (d, J=3.3 Hz, 1H), 5.23 (d, J=3.0 Hz, 1H), 4.4-4.6 (m, 4H), 3.1-3.9 (m, 32H), 2.3-2.4 (m, 1H), 1.74 (ddd, J=12.3 Hz 1H). $^{13}$C NMR (75 MHz, D$_2$O) δ 136.64, 136.26, 129.05 (2 Carbons), 128.96 (2 Carbons), 128.90, 128.82 (2 Carbons), 128.69 (2 Carbons), 128.63, 97.99, 95.10, 82.61, 81.44, 81.31, 79.85, 79.68, 78.56, 75.78, 74.50, 73.38, 73.16, 71.38, 68.29, 67.10, 60.19, 59.98, 59.86, 59.63, 58.36, 53.04, 49.68, 48.15, 40.09, 28.18. ESI/APCI calcd for $C_{37}H_{59}N_4O_{11}$ m/z 735.4175; measured m/z 735.4196. Yield: 130 mg (148 mmol, 92%).

5, 2', 3', 4', 2"-Penta-O-methyl-kanamycin (9). $^1$H NMR (300 MHz, D$_2$O) 5.46 (d, J=3.3 Hz, 1H), 5.35 (d, J=3.3 Hz, 1H), 4.00 (t, J=9.9 Hz, 1H), 3.1-3.9 (m, 31H), 2.3-2.4 (m, 1H), 1.83 (ddd, J=12.3 Hz 1H). $^{13}$C NMR (75 MHz, D$_2$O) δ 98.30, 94.44, 81.57, 81.41, 80.60, 79.81, 79.67, 78.70, 74.80, 73.02, 68.45, 65.26, 60.19, 59.97 (2 Carbons), 59.59, 59.52, 57.11, 53.82, 49.73, 47.85, 40.10, 27.44. ESI/APCI calcd for C23H47N4O11 [MH]$^+$: m/z 555.3236; measured m/z 555.3234. Yield: 14 mg (20 mmol, 27%).

4",6"-Di-O-(4-methoxybenzyl) kanamycin (10). $^1$H NMR (500 MHz, D$_2$O) δ 6.94 (d, J=8.6 Hz, 2H), 6.63 (d, J=8.6 Hz, 2H), 6.4-6.5 (m, 4H), 5.18 (d, J=3.6 Hz, 1H), 4.68 (m, 1H, overlapped with H2O), 4.24 (d, J=11.8 Hz, 1H), 4.03 (d, J=10.4 Hz, 1H), 3.97 (d, J=11.5 Hz, 1H), 3.75 (d, J=10.4 Hz, 1H), 2.7-3.7 (m, 23H), 2.1-2.2 (m, 1H), 1.51 (ddd, J=12.4 Hz 1H). $^{13}$C NMR (125 MHz, D$_2$O) δ 158.61, 158.48, 130.71 (2 Carbons), 130.01 (2 Carbons), 128.28, 128.13, 113.59 (2 Carbons), 113.54 (2 Carbons), 100.34, 96.00, 83.63, 77.57, 73.65, 72.41 (2 Carbons), 72.09, 71.53, 70.42 (2 Carbons), 70.36, 69.25, 67.70, 65.80, 54.79, 54.63, 53.75, 49.47, 47.36, 39.91. ESI/APCI calcd for C$_{34}$H$_{52}$N$_4$O$_{13}$Na [M+Na]$^+$: 747.3423 m/z; measured 747.3436 m/z. Yield: 173 mg (199 mmol, 54%).

4",6"-Di-O-(4-methylbenzyl) kanamycin (11). $^1$H NMR (500 MHz, D$_2$O) δ 7.23 (d, J=7.9 Hz, 2H), 7.13 (d, J=7.4 Hz, 4H), 7.13 (d, J=7.9 Hz, 2H), 5.49 (d, J=4.0 Hz, 1H), 5.05 (d, J=3.7 Hz, 1H), 4.54 (d, J=11.6 Hz, 1H), 4.47 (d, J=10.8 Hz, 1H), 4.36 (d, J=11.6 Hz, 1H), 4.25 (d, J=10.8 Hz, 1H), 4.0-4.1 (m, 1H), 3.8-4.0 (m, 4H), 3.6-3.7 (m, 4H), 3.4-3.5 (m, 5H), 3.2-3.3 (m, 2H), 3.1-3.2 (m, 1H), 2.4-2.5 (m, 1H), 2.25 (s, 3H), 2.18 (s, 3H), 1.88 (ddd, J=12.5 Hz 1H). $^{13}$C NMR (125 MHz, D$_2$O) δ 139.12, 138.86, 133.37, 133.08, 129.38 (4 Carbons), 129.19 (2 Carbons), 128.75 (2 Carbons), 100.44, 96.28, 83.83, 78.03, 74.21, 73.13, 72.88, 72.74, 72.02, 70.94, 70.79, 70.76, 68.63, 68.02, 66.93, 54.20, 49.83, 47.81, 40.33, 27.56, 20.30, 20.28. ESI/APCI calcd for C$_{34}$H$_{53}$N$_4$O$_{11}$ [MH]$^+$: 693.3705 m/z; measured 693.3731 m/z. Yield: 198 mg (236 mmol, 88%).

4",6"-Di-O-(4-chlorobenzyl) kanamycin (12). $^1$H NMR (500 MHz, D$_2$O) δ 7.2-7.3 (m, 6H), 7.07 (d, J=8.4 Hz 2H), 5.44 (d, J=3.9 Hz, 1H), 5.44 (d, J=3.6 Hz, 1H), 4.5-4.6 (m, 2H), 4.36 (d, J=11.9 Hz, 1H), 4.27 (d, J=11.3 Hz, 1H), 4.0-4.1 (m, 1H), 4.0-4.1 (m, 1H), 3.1-3.9 (m, 15H), 2.4-2.5 (m, 1H), 1.81 (ddd, J=12.5 Hz 1H). $^{13}$C NMR (125 MHz, D$_2$O) δ 135.06, 134.82, 133.73, 133.66, 130.50 (2 Carbons), 129.64 (2 Carbons), 128.72 (2 Carbons), 128.69 (2 Carbons), 100.40, 96.56, 84.09, 78.39, 73.58, 73.51, 73.02, 72.24, 71.99, 70.77 (4 Carbons), 68.61, 68.12, 67.09, 54.20, 49.87, 47.96, 40.32, 28.05. ESI/APCI calcd for C$_{32}$H$_{47}$Cl$_2$N$_4$O$_{11}$ [MH]$^+$: 733.2613 m/z; measured 733.2621 m/z. Yield: 53 mg (60 mmol, 58%).

4",6"-Di-O-(4-flurobenzyl) kanamycin (13). $^1$H NMR (500 MHz, D$_2$O) 7.3-7.4 (m, 2H), 7.1-7.2 (m, 2H), 7.0-7.1 (m, 4H), 5.47 (d, J=3.9 Hz, 1H), 5.03 (d, J=3.6 Hz, 1H), 4.5-4.6 (m, 2H), 4.41 (d, J=11.6 Hz, 1H), 4.34 (d, J=11.0 Hz, 1H), 4.0-4.1 (m, 1H), 3.3-3.9 (m, 16H), 2.3-2.4 (m, 1H), 1.82 (ddd, J=12.5 Hz 1H). $^{13}$C NMR (125 MHz, D$_2$O) δ 162.57 (d, J$_{CF}$=244.3 Hz), 162.49 (d, J$_{CF}$=244.3 Hz), 132.46 (d, J$_{CF}$=2.8 Hz), 132.12 (d, J$_{CF}$=2.8 Hz), 130.94 (d, J$_{CF}$=8.4 Hz, 2 Carbons), 130.43 (d, J$_{CF}$=8.4 Hz, 2 Carbons), 115.49 (d, J$_{CF}$=21.6 Hz, 2 Carbons), 115.43 (d, J$_{CF}$=21.6 Hz, 2 Carbons), 100.44, 98.51, 83.98, 78.40, 73.60, 73.31, 72.87, 72.34, 72.01, 70.83, 70.75, 70.70, 68.62, 68.07, 67.11, 54.17, 49.58, 47.87, 40.26, 27.88. ESI/APCI calcd for C$_{32}$H$_{47}$F$_2$N$_4$O$_{11}$ [MH]$^+$: 701.3204 m/z; measured 701.3200 m/z. Yield: 66 mg (78 mmol, 71%).

4",6"-Di-O-(2-naphthalenmethyl) kanamycin (14). $^1$H NMR (500 MHz, D$_2$O) δ 7.2-7.7 (m, 13H), 7.00 (dd, J=8.4 Hz, J=1.6 Hz, 1H), 5.39 (d, J=3.9 Hz, 1H), 5.06 (d, J=3.6 Hz, 1H), 4.6-4.7 (m, 2H), 4.37 (d, J=11.9 Hz, 1H), 4.28 (d, J=11.4 Hz, 1H), 4.0-4.1 (m, 1H), 3.0-3.9 (m, 16H), 2.3-2.4 (m, 1H), 1.86 (ddd, J=12.5 Hz 1H). $^{13}$C NMR (125 MHz, D$_2$O) δ 133.79, 133.50, 132.84, 132.77, 132.69, 132.53, 128.47, 128.31, 127.99, 127.81 (2 Carbons), 127.61, 127.60, 127.01, 126.62, 126.55, 126.52 (2 Carbons), 126.47, 125.62, 100.43, 96.46, 83.87, 77.83, 73.24, 73.04, 72.98, 71.90, 70.90, 70.68, 70.65, 68.59, 68.03, 66.99, 54.24, 49.76, 47.92, 40.29, 27.54. ESI/APCI calcd for C$_{40}$H$_{53}$N$_4$O$_{11}$ [MH]$^+$: 765.3705 m/z; measured 765.3755 m/z. Yield: 85 mg (94 mmol, 72%).

4",6"-Di-O-(1-naphthalenmethyl) kanamycin (15). $^1$H NMR (500 MHz, D$_2$O) δ 7.87 (d, J=8.3 Hz, 1H), 7.7-7.8 (m, 4H), 7.5-7.6 (m, 2H), 7.2-7.5 (m, 6H), 7.06 (d, J=6.8 Hz, 1H), 5.17 (d, J=3.9 Hz, 1H), 5.05 (d, J=3.6 Hz, 1H), 4.7-4.8 (m, 2H), 4.3-4.4 (m, 2H), 3.9-4.0 (m, 1H), 3.3-3.7 (m, 15H), 2.9-3.0 (m, 1H), 2.4-2.5 (m, 1H), 1.84 (ddd, J=12.5 Hz 1H). $^{13}$C NMR (125 MHz, D$_2$O) δ 133.49, 133.38, 131.85, 131.80, 131.35, 130.65, 129.34, 129.29, 128.75, 128.68, 127.94, 127.28, 126.92, 126.68, 126.29, 126.11, 125.46, 125.34, 123.65, 123.14, 100.07, 96.06, 83.59, 77.81, 73.81, 72.77, 72.11, 71.97, 71.09, 71.06, 70.71, 70.61, 68.46, 67.89, 67.70, 54.33, 49.68, 47.70, 40.21, 27.51. ESI/APCI calcd for C$_{40}$H$_{53}$N$_4$O$_{11}$ [MH]$^+$: 765.3705 m/z; measured 765.3704 m/z. Yield: 209 mg (229 mmol, 42%).

4",6"-Di-O-(3-phenylbenzyl)-kanamycin (16). $^1$H NMR (500 MHz, D$_2$O) δ 7.42 (s, 1H), 7.1-7.4 (m, 16H), 7.03 (d, J=7.6 Hz, 1H), 5.49 (d, J=3.9 Hz, 1H), 5.05 (d, J=3.4 Hz, 1H), 4.59 (d, J=12.0 Hz, 1H), 4.51 (d, J=11.1 Hz, 1H), 4.2-4.3 (m, 2H), 4.0-4.1 (m, 1H), 3.0-3.9 (m, 16H), 2.4-2.5 (m, 1H), 1.86 (dd, J=12.5 Hz, 1H). 13C NMR (125 MHz, D$_2$O) δ 140.75, 140.68, 139.89, 139.78, 136.80, 136.78, 129.35, 129.25, 129.03 (2 Carbons), 128.92 (2 Carbons), 128.12, 127.76, 127.65, 127.23, 127.21, 126.98, 126.94, 126.84 (2 Carbons), 126.72 (2 Carbons), 126.50, 100.52, 96.86, 83.73, 78.25, 74.21, 73.28, 73.00 (2 Carbons), 71.96, 70.91, 70.76, 70.68, 68.66, 68.05, 66.91, 54.23, 49.81, 47.92, 40.26, 27.58. ESI/APCI calcd for C$_{44}$H$_{57}$N$_4$O$_{11}$ [MH]$^+$: 817.4024 m/z; measured 817.4005 m/z. Yield: 215 mg (223 mmol, 74%).

Example 3

K46: modification at O-4" and O-6" positions except for compounds 8 and d9 in the examples above.
K: modification at O-6" position.
KI: modification at N-6' position.

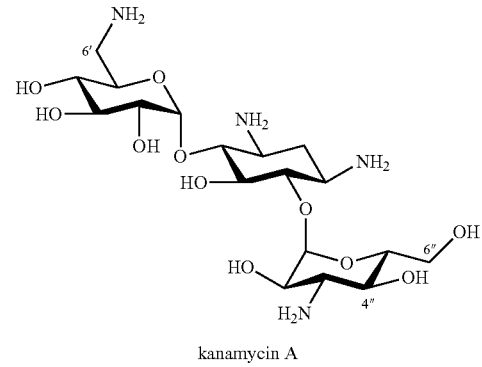

kanamycin A

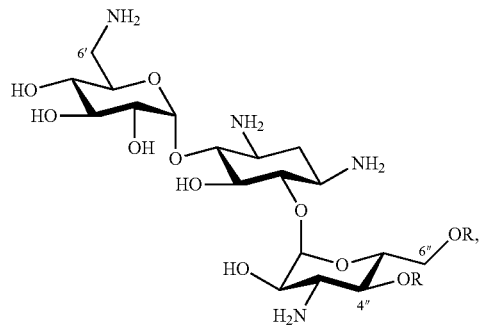

K46

51
-continued
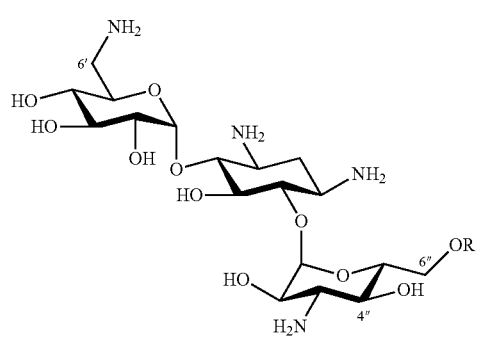
K
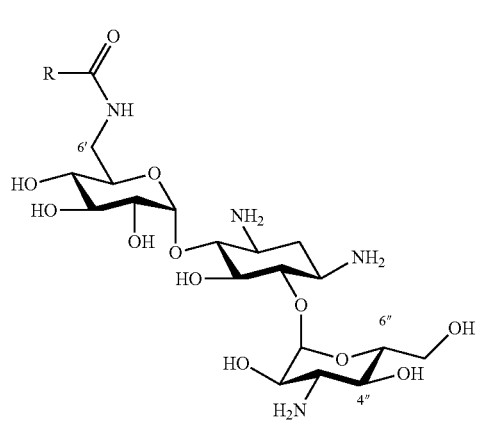
KI
Synthesis of K and KI compounds
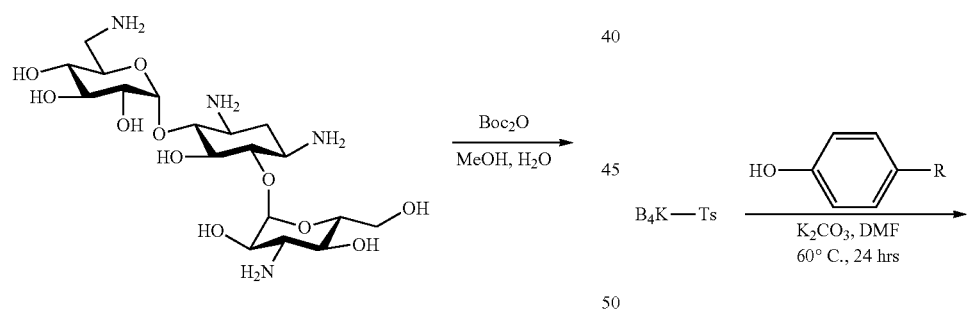
B₄K
90%
52
-continued
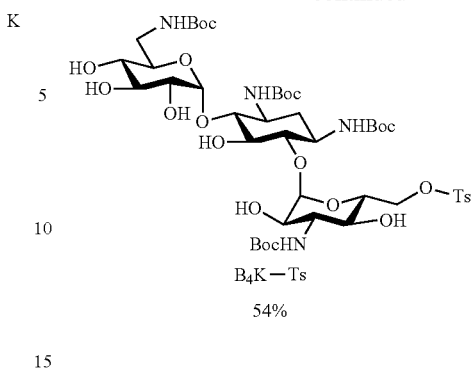
B₄K—Ts
54%
1. TFA, DCM
2. Ion exchange →
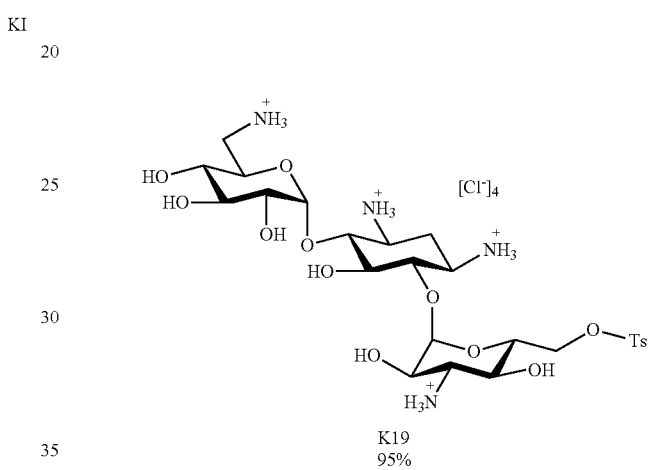
K19
95%
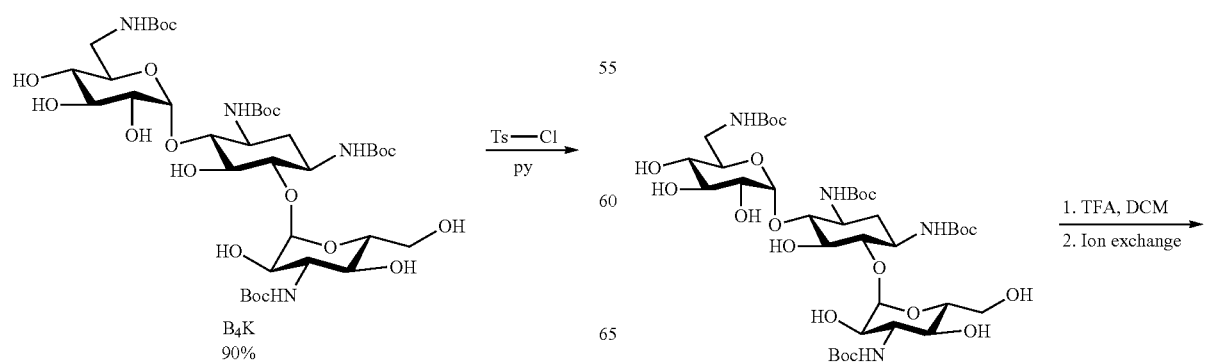
1. TFA, DCM
2. Ion exchange →

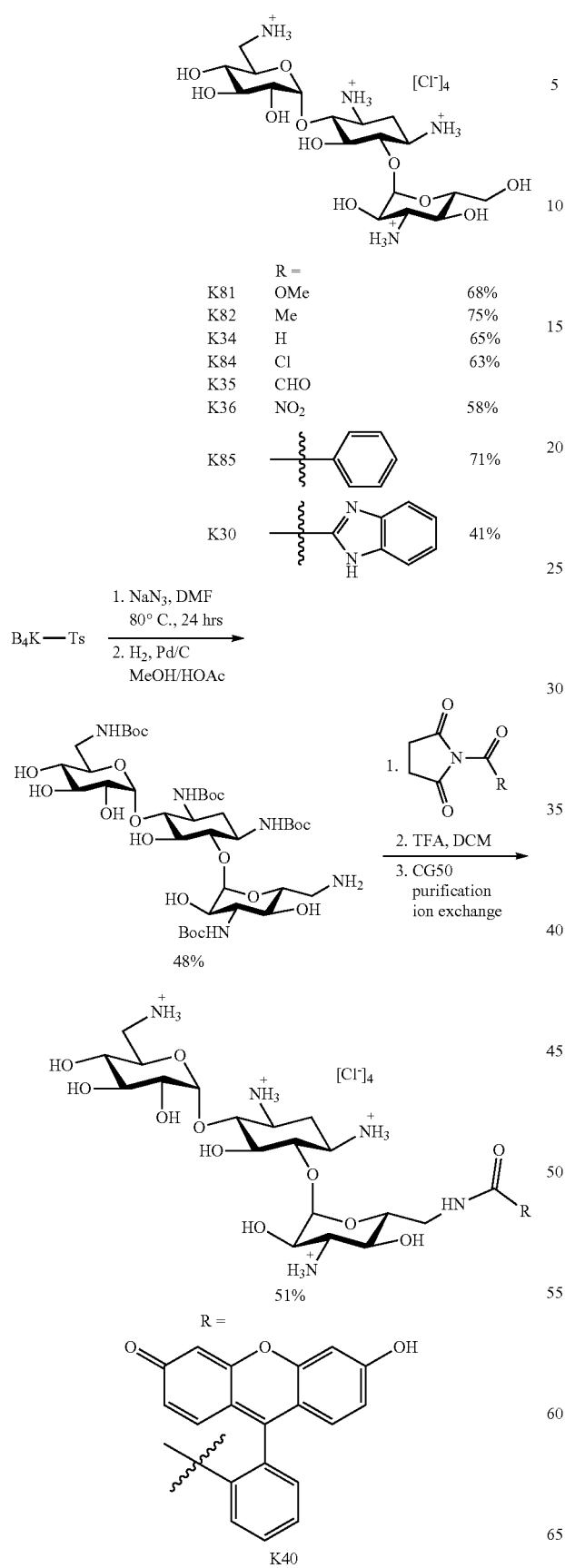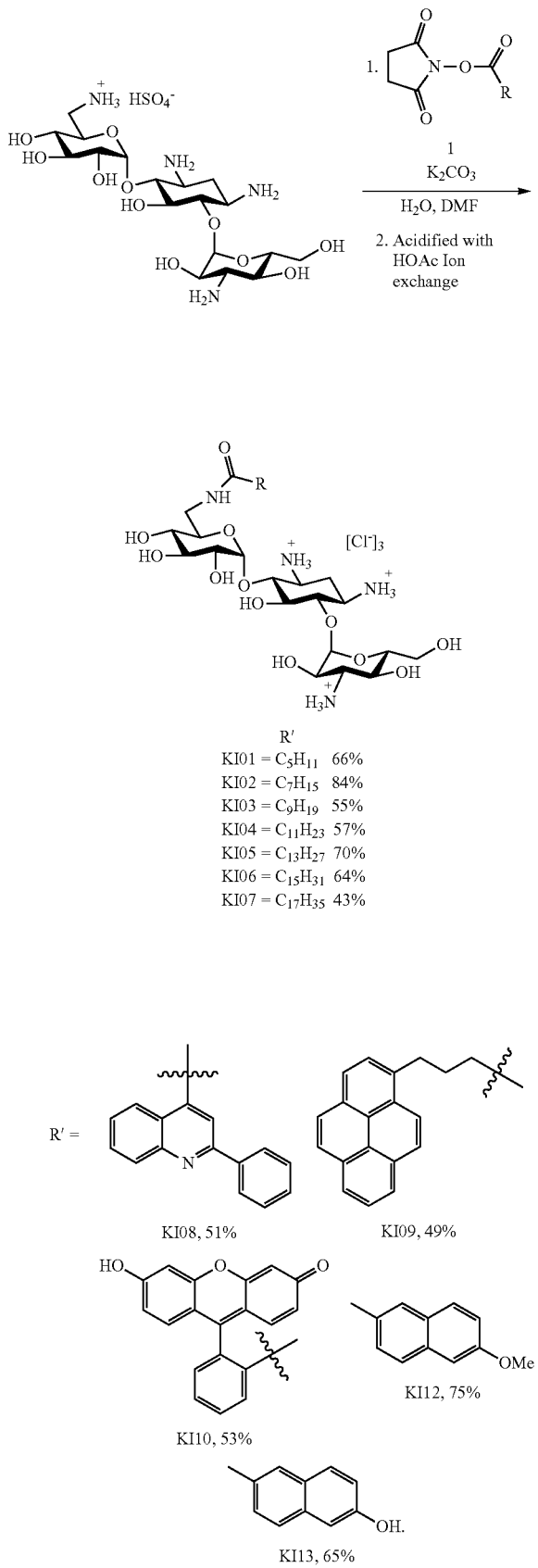

Activity of K46 members
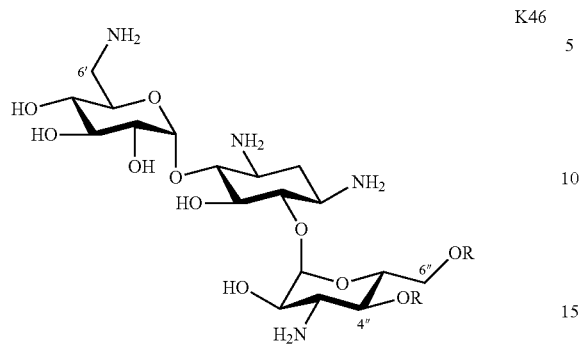
K46
| Code/compound # | R | IC$_{50}$ (μM) against Cx26 | IC$_{50}$ (μM) against Cx43 |
|---|---|---|---|
| K46B01/7 | Benzyl | 7.6 ± 1.2 μM | |
| K46BM5/8 | Benzyl and all hydroxyl groups were methylated | 8.4 ± 1.4 μM | |
| K46B09/10 |  | 13.0 ± 0.7 | 4.1 ± 1.5 |
| K46B03/11 |  | 4.3 ± 0.4 | 3.1 ± 0.9 |
| K46B10/12 |  | 2.5 ± 0.6 | 20.3 |
| K46B04/13 |  | 8.1 ± 0.5 | 26.6 ± 7.8 |
| K46B05/14 |  | 4.9 ± 0.2 | |
| K46B11/15 |  | 6.6 ± 0.5 | 15 |

-continued
| Code/ compound # | R | IC$_{50}$ (μM) against Cx26 | IC$_{50}$ (μM) against Cx43 |
|---|---|---|---|
| K46B07/16 | 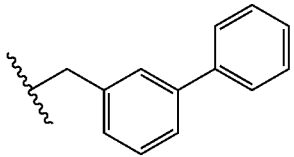 [SMILES: *Cc1cccc(-c2ccccc2)c1] | 6.2 ± 0.7 | 5.5 ± 2 |
| K4604/2 | Butyl | 19.0 ± 2.8 | |
| K4606/3 | Hexyl | 6.2 ± 1.4 | |
| K4608/5 | Octyl | 13.6 ± 0.5 | 26.6 ± 7.8 |
| K4609/6 | Nonyl | 18.8 ± 1.3 | |
Activity of K members
| | | Cx26 % inhibition | | Cx43 % inhibition | |
|---|---|---|---|---|---|
| Code | Structures | 15 μM | 50 μM | 15 μM | 50 μM |
| K19 | 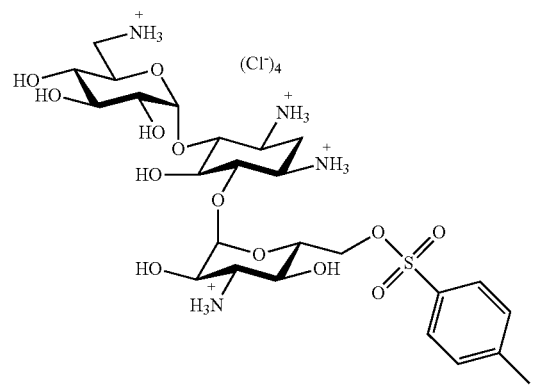 | 26.8 ± 1.7 | 49.2 ± 5.5 | 38.1 ± 2.8 | 51.0 ± 8.8 |
| K30 | 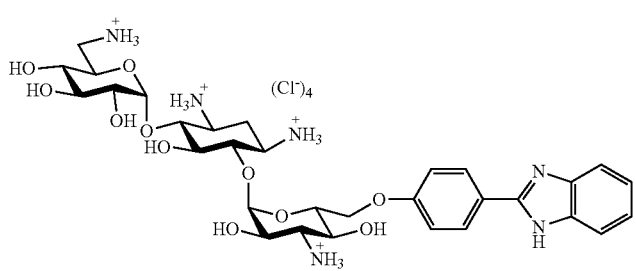 | | | 8.9 | 89.4 |
| K34 | 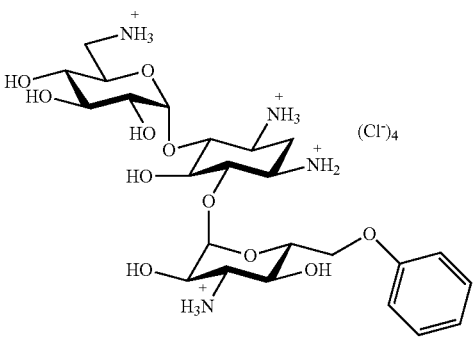 | 14.6 ± 4.3 | 69.4 ± 4.2 | 36.0 ± 3.9 | 46.7 ± 7.8 |

-continued
| Code | Structures | Cx26 % inhibition | | Cx43 % inhibition | |
|---|---|---|---|---|---|
| | | 15 μM | 50 μM | 15 μM | 50 μM |
| K36 | 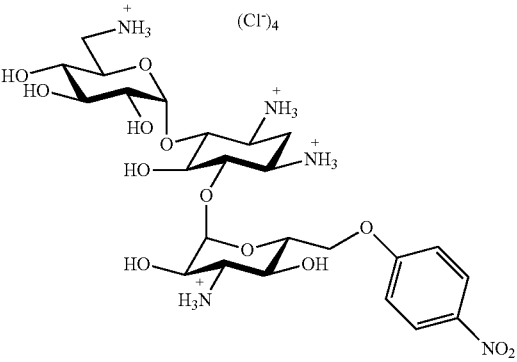 | 35.9 ± 2.9 | 62.6 ± 9.2 | 36.5 ± 0.6 | 49.3 ± 2.2 |
| K40* | 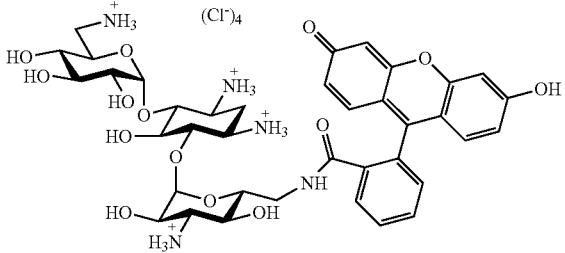 | 37.1 ± 13.5 | 81.0 ± 1.7 | 45.3 ± 2.7 | 55.1 ± 5.8 |
| K81 | 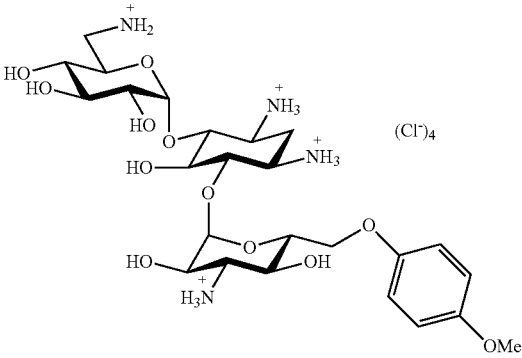 | 15.9 ± 4.2 | 36.5 ± 4.7 | 20.0 ± 7.4 | 34.8 ± 7.8 |
| K82 | 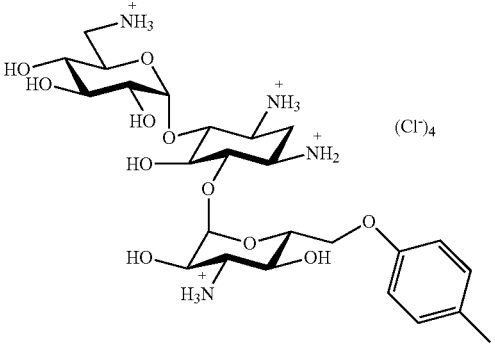 | 19.3 ± 2.2 | 28.2 ± 4.5 | 58.4 ± 10.6* | 71.0 ± 14.1* |

| Code | Structures | Cx26 % inhibition | | Cx43 % inhibition | |
| --- | --- | --- | --- | --- | --- |
| | | 15 μM | 50 μM | 15 μM | 50 μM |
| K84 | 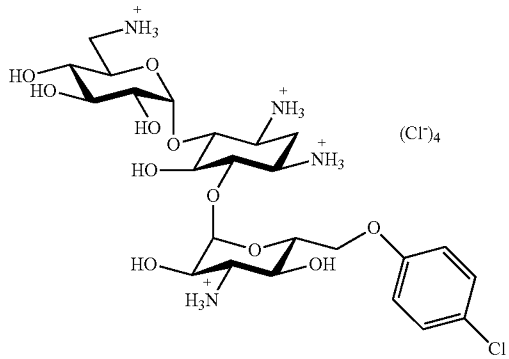 | 44.4 ± 7.0 | 69.5 ± 4.5 | 45.8 ± 6.4* | 76.7 ± 7.7* |
| K85 | 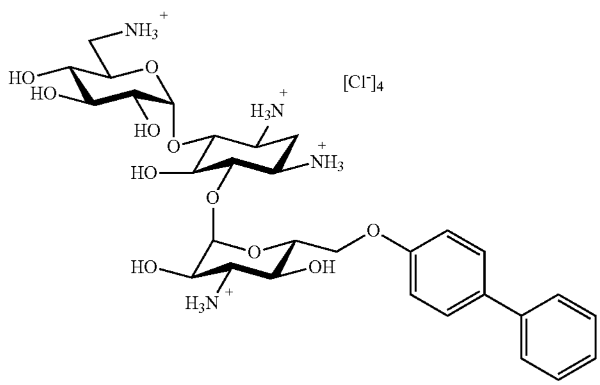 | ND | | ND | |

*the linker is N atom instead of O atom.

| | Cx26 | | Cx43 | |
| --- | --- | --- | --- | --- |
| Compound | IC$_{50}$ (μM) | I$_{max}$ (%) | IC$_{50}$ (μM) | I$_{max}$ (%) |
| K82 | | | 7.1 ± 1.4 | 91.1 ± 11.5 |
| K84 | 17.2 ± 3.2 | 95.9 ± 10.9 | 8.9 ± 1.6 | 80.6 ± 6.0 |

V. Activity of KI members

| Code | Structures | Cx26 % inhibition | | Cx43 % inhibition | |
| --- | --- | --- | --- | --- | --- |
| | | 15 μM | 50 μM | 15 μM | 50 μM |
| KI01 | 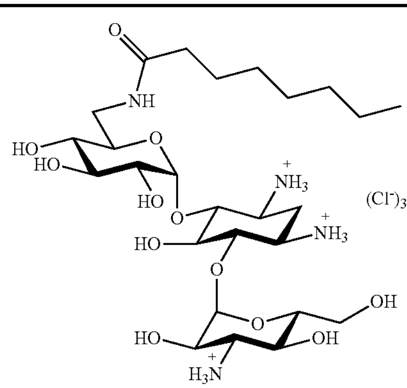 | 22.5 ± 1.9 | 34.3 ± 2.6 | 18.5 ± 0.7 | 36.0 ± 6.1 |

-continued
| Code | Structures | Cx26 % inhibition | | Cx43 % inhibition | |
| --- | --- | --- | --- | --- | --- |
| | | 15 μM | 50 μM | 15 μM | 50 μM |
| KI02 | 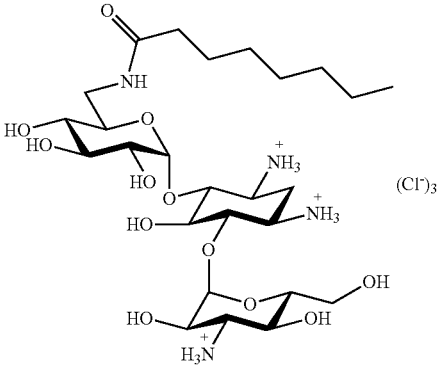 | 14.0 ± 2.1 | 25.2 ± 2.3 | 17.0 ± 5.2 | 37.2 ± 7.6 |
| KI03 | 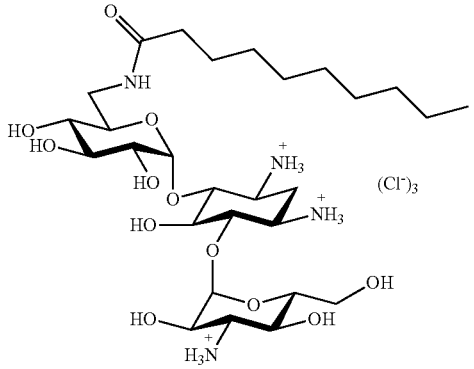 | 16.1 ± 3.2 | 33.6 ± 3.8 | 44.4 ± 5.3 | 53.5 ± 1.9 |
| KI04 | 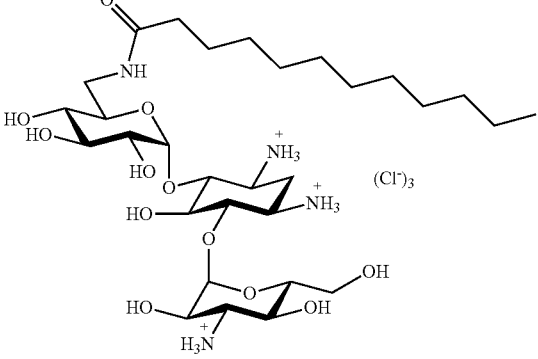 | 16.4 ± 2.3 | 56.2 ± 6.8 | 43.9 ± 4.3* | 58.2 ± 3.9* |
| KI05 | 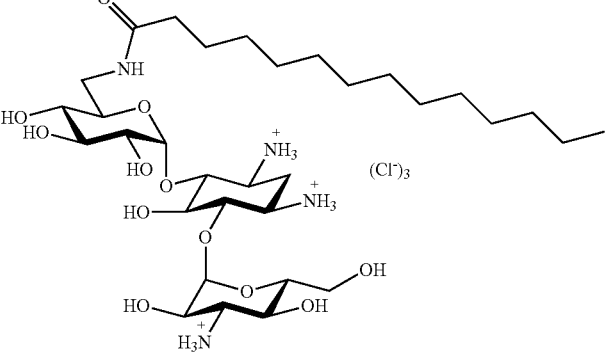 | ND | | ND | |

| Code | Structures | Cx26 % inhibition | | Cx43 % inhibition | |
|---|---|---|---|---|---|
| | | 15 μM | 50 μM | 15 μM | 50 μM |
| KI06 | (structure) | ND | | ND | |
| KI07 | (structure) | ND | | ND | |
| KI08 | (structure) | 8.8 ± 2.0 | 22.8 ± 2.2 | 25.5 ± 7.1 | 51.0 ± 2.5 |

-continued
| Code | Structures | Cx26 % inhibition | | Cx43 % inhibition | |
|---|---|---|---|---|---|
| | | 15 μM | 50 μM | 15 μM | 50 μM |
| KI09 | 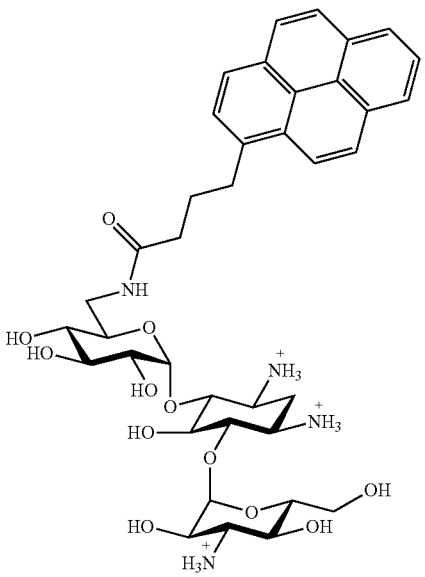 | 36.9 ± 3.9 | 79.2 ± 7.5 | 43.0 ± 10.7* | 56.8 ± 11.0* |
| KI10 | 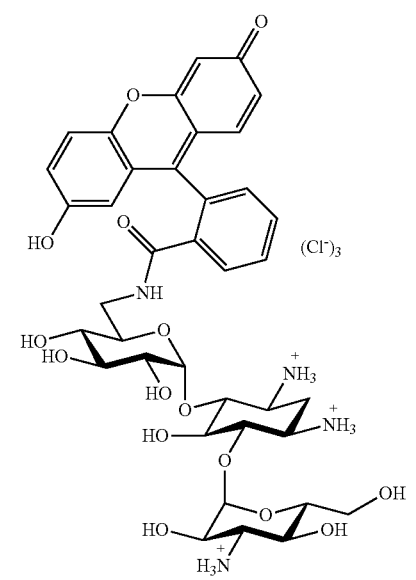 | 22.3 ± 6.9 | 79.6 ± 3.5 | 56.8 ± 8.8 | 83.4 ± 1.1 |

-continued

| Code | Structures | Cx26 % inhibition | | Cx43 % inhibition | |
|---|---|---|---|---|---|
| | | 15 μM | 50 μM | 15 μM | 50 μM |
| KI12 | 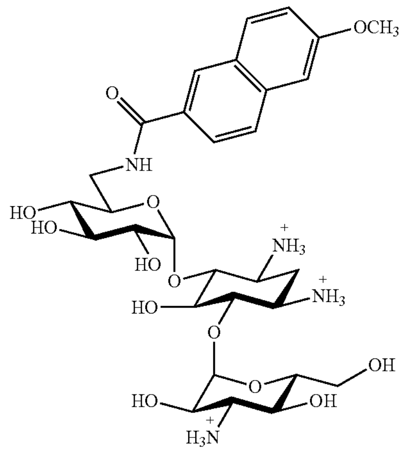 | ND | | ND | |
| KI13 | 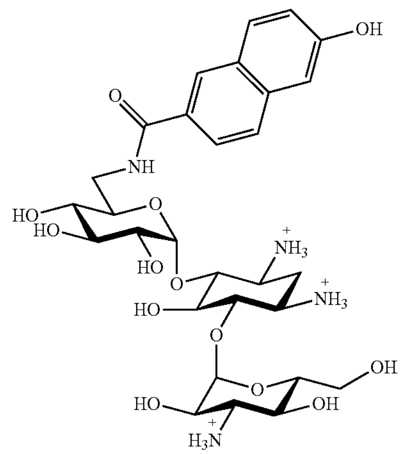 | ND | | ND | |

| | Cx26 | | Cx43 | |
|---|---|---|---|---|
| Compound | $IC_{50}$ (μM) | $I_{max}$ (%) | $IC_{50}$ (μM) | $I_{max}$ (%) |
| K82 | | | 7.1 ± 1.4 | 91.1 ± 11.5 |
| K84 | 17.2 ± 3.2 | 95.9 ± 10.9 | 8.9 ± 1.6 | 80.6 ± 6.0 |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES—EXAMPLE 1

1. Abascal, F.; Zardoya, R., Evolutionary analyses of gap junction protein families. Biochem. Biophys. Acta 2013, 1828 (1), 4-14.
2. Harris, A.; Locke, D., Connexins: A Guide. Humana Press: 2009; Vol. Ch. 7, pp 165-207.
3. Mese, G.; Richard, G.; White, T. W., Gap junctions: basic structure and function. J. Invest. Dermatol. 2007, 127 (11), 2516-2524.
4. Nielsen, M. S.; Nygaard Axelsen, L.; Sorgen, P. L.; Verma, V.; Delmar, M.; Holstein-Rathlou, N. H., Gap junctions. Comprehensive Physiology 2012, 2 (3), 1981-2035.
5. Bennett, B. C.; Purdy, M. D.; Baker, K. A.; Acharya, C.; McIntire, W. E.; Stevens, R. C.; Zhang, Q.; Harris, A. L.; Abagyan, R.; Yeager, M., An electrostatic mechanism for Ca(2+)-mediated regulation of gap junction channels. Nat Commun 2016, 7, 8770.
6. Maeda, S.; Nakagawa, S.; Suga, M.; Yamashita, E.; Oshima, A.; Fujiyoshi, Y.; Tsukihara, T., Structure of the connexin 26 gap junction channel at 3.5 A resolution. Nature 2009, 458 (7238), 597-602.
7. Paulis, L. E.; Klein, A. M.; Ghanem, A.; Geelen, T.; Coolen, B. F.; Breitbach, M.; Zimmermann, K.; Nicolay, K.; Fleischmann, B. K.; Roell, W.; Strijkers, G. J., Embryonic cardiomyocyte, but not autologous stem cell transplantation, restricts infarct expansion, enhances ventricular function, and improves long-term survival. PloS one 2013, 8 (4), e61510.
8. Fiori, M. C.; Reuss, L.; Cuello, L. G.; Altenberg, G. A., Functional analysis and regulation of purified connexin hemichannels. Front Physiol 2014, 5, 71.
9. Wang, N.; De Bock, M.; Decrock, E.; Bol, M.; Gadicherla, A.; Vinken, M.; Rogiers, V.; Bukauskas, F. F.; Bultynck, G.; Leybaert, L., Paracrine signaling through plasma membrane hemichannels. Biochimica et biophysica acta 2013, 1828 (1), 35-50.
10. Shintani-Ishida, K.; Uemura, K.; Yoshida, K., Hemichannels in cardiomyocytes open transiently during ischemia and contribute to reperfusion injury following brief ischemia. American journal of physiology. Heart and circulatory physiology 2007, 293 (3), H1714-20.
11. Lee, J. R.; White, T. W., Connexin-26 mutations in deafness and skin disease. Expert reviews in molecular medicine 2009, 11, e35.
12. Beyer, E. C.; Berthoud, V. M., Connexin hemichannels in the lens. Front Physiol 2014, 5, 20.
13. Schulz, R.; Gorge, P. M.; Gorbe, A.; Ferdinandy, P.; Lampe, P. D.; Leybaert, L., Connexin 43 is an emerging therapeutic target in ischemia/reperfusion injury, cardioprotection and neuroprotection. Pharmacol Ther 2015, 153, 90-106.
14. Orellana, J. A.; Avendano, B. C.; Montero, T. D., Role of connexins and pannexins in ischemic stroke. Curr Med Chem 2014, 21 (19), 2165-82.
15. Vergara, L.; Bao, X.; Bello-Reuss, E.; Reuss, L., Do connexin 43 gap junctional hemichannels activate and cause cell damage during ATP depletion of renal-tubule cells? Acta physiologica Scandinavica 2003, 179 (1), 33-8.
16. Stong, B. C.; Chang, Q.; Ahmad, S.; Lin, X., A novel mechanism for connexin 26 mutation linked deafness: cell death caused by leaky gap junction hemichannels. The Laryngoscope 2006, 116 (12), 2205-10.

17. Tao, L.; Harris, A. L., 2-aminoethoxydiphenyl borate directly inhibits channels composed of connexin26 and/or connexin32. Mol. Pharmacol. 2007, 71 (2), 570-579.
18. Leithe, E.; Kjenseth, A.; Bruun, J.; Sirnes, S.; Rivedal, E., Inhibition of connexin43 gap junction channels by the endocrine disruptor ioxynil. Toxicol. Appl. Pharm. 2010, 247 (1), 10-17.
19. Sagar, G.; Larson, D., Carbenoxolone inhibits junctional transfer and upregulates connexin43 expression by a protein kinase A-dependent pathway. J. Cel. Biochem. 2006, 98 (6), 1543-1551.
20. Contreras, J. E.; Sánchez, H. A.; Eugenín, E. A.; Speidel, D.; Theis, M.; Willecke, K.; Bukauskas, F. F.; Bennett, M. V.; Sáez, J. C., Metabolic inhibition induces opening of unapposed connexin 43 gap junction hemichannels and reduces gap junctional communication in cortical astrocytes in culture. PNAS 2002, 99 (1), 495-500.
21. Seemann, N.; Welling, A.; Rustenbeck, I., The inhibitor of connexin Cx36 channels, mefloquine, inhibits voltage-dependent Ca 2+ channels and insulin secretion. Mol. Cell. Endocrinol. 2017.
22. Zhao, K.; Wang, W.; Guan, C.; Cai, J.; Wang, P., Inhibition of gap junction channel attenuates the migration of breast cancer cells. Mol. Biol. Rep. 2012, 39 (3), 2607-2613.
23. De Vuyst, E.; Boengler, K.; Antoons, G.; Sipido, K. R.; Schulz, R.; Leybaert, L., Pharmacological modulation of connexin-formed channels in cardiac pathophysiology. British journal of pharmacology 2011, 163 (3), 469-83.
24. Herve, J. C.; Dhein, S., Peptides targeting gap junctional structures. Current pharmaceutical design 2010, 16 (28), 3056-70.
25. Willebrords, J.; Maes, M.; Crespo Yanguas, S.; Vinken, M., Inhibitors of connexin and pannexin channels as potential therapeutics. Pharmacol Ther 2017, 180, 144-160.
26. Dalamon, V.; Fiori, M. C.; Figueroa, V. A.; Oliva, C. A.; Del Rio, R.; Gonzalez, W.; Canan, J.; Elgoyhen, A. B.; Altenberg, G. A.; Retamal, M. A., Gap junctional channel and hemichannel activity of two recently identified connexin 26 mutants associated with deafness. Pflugers Archiv: European journal of physiology 2016.
27. Figueroa, V. A.; Retamal, M. A.; Cea, L. A.; Salas, J. D.; Vargas, A. A.; Verdugo, C. A.; Jara, O.; Martinez, A. D.; Saez, J. C., Extracellular gentamicin reduces the activity of connexin hemichannels and interferes with purinergic Ca(2+) signaling in HeLa cells. Frontiers in cellular neuroscience 2014, 8, 265.
28. Fiori, M. C.; Krishnan, S.; Cortes, D. M.; Retamal, M. A.; Reuss, L.; Altenberg, G. A.; Cuello, L. G., Functional hemichannels formed by human connexin 26 expressed in bacteria. Bioscience reports 2015, 35 (2).
29. Krishnan, S.; Fiori, M. C.; Whisenant, T. E.; Cortes, D. M.; Altenberg, G. A.; Cuello, L. G., An *Escherichia coli*-Based Assay to Assess the Function of Recombinant Human Hemichannels. SLAS Discov 2017, 22 (2), 135-143.
30. Kotra, L. P.; Haddad, J.; Mobashery, S., Aminoglycosides: perspectives on mechanisms of action and resistance and strategies to counter resistance. Antimicrob. Agents Chemother. 2000, 44 (12), 3249-3256.
31. Vakulenko, S. B.; Mobashery, S., Versatility of aminoglycosides and prospects for their future. Clin. Microbiol. Rev. 2003, 16 (3), 430-450.
32. Mingeot-Leclercq, M.-P.; Tulkens, P. M., Aminoglycosides: nephrotoxicity. Antimicrob. Agents Chemother. 1999, 43 (5), 1003-1012.
33. Fosso, M.; AlFindee, M. N.; Zhang, Q.; Nziko, V. d. P. N.; Kawasaki, Y.; Shrestha, S. K.; Bearss, J.; Gregory, R.; Takemoto, J. Y.; Chang, C.-W. T., Structure—Activity Relationships for Antibacterial to Antifungal Conversion of Kanamycin to Amphiphilic Analogues. J. Org. Chem. 2015, 80 (9), 4398-4411.
34. Zhang, Q.; Alfindee, M. N.; Shrestha, J. P.; Nziko, V. d. P. N.; Kawasaki, Y.; Peng, X.; Takemoto, J. Y.; Chang, C.-W. T., Divergent Synthesis of Three Classes of Antifungal Amphiphilic Kanamycin Derivatives. J. Org. Chem. 2016, 81 (22), 10651-10663.
35. Chang, C.-W. T.; Fosso, M.; Kawasaki, Y.; Shrestha, S.; Bensaci, M. F.; Wang, J.; Evans, C. K.; Takemoto, J. Y., Antibacterial to antifungal conversion of neamine aminoglycosides through alkyl modification. Strategy for reviving old drugs into agrofungicides. J. Antibiot. 2010, 63 (11), 667-672.
36. Shrestha, S.; Grilley, M.; Fosso, M. Y.; Chang, C.-W. T.; Takemoto, J. Y., Membrane lipid-modulated mechanism of action and non-cytotoxicity of novel fungicide aminoglycoside FG08. PloS one 2013, 8 (9), e73843.
37. Shrestha, S. K.; Chang, C.-W. T.; Meissner, N.; Oblad, J.; Shrestha, J. P.; Sorensen, K. N.; Grilley, M. M.; Takemoto, J. Y., Antifungal amphiphilic aminoglycoside K20: bioactivities and mechanism of action. Front. Microbiol. 2014, 5 (671).
38. Shrestha, S. K.; Grilley, M.; Anderson, T.; Dhiman, C.; Oblad, J.; Chang, C.-W. T.; Sorensen, K. N.; Takemoto, J. Y., In vitro antifungal synergy between amphiphilic aminoglycoside K20 and azoles against *Candida* species and *Cryptococcus neoformans*. Med. Mycol. 2015, 53 (8), 837-844.
39. Krishnan, S.; Fiori, M. C.; Whisenant, T. E.; Cortes, D. M.; Altenberg, G. A.; Cuello, L. G., An *Escherichia coli*-based assay to assess the function of recombinant human hemichannels. SLAS Discov. 2017, 22 (2), 135-143.
40. Stumpe, S.; Bakker, E. P., Requirement of a large K+-uptake capacity and of extracytoplasmic protease activity for protamine resistance of *Escherichia coli*. Arch. Microbiol. 1997, 167 (2-3), 126-136.
41. Buurman, E. T.; McLaggan, D.; Naprstek, J.; Epstein, W., Multiple paths for nonphysiological transport of K+ in *Escherichia coli*. J. Bacteriol. 2004, 186 (13), 4238-4245.
42. Fiori, M. C.; Krishnan, S.; Cortes, D. M.; Retamal, M. A.; Reuss, L.; Altenberg, G. A.; Cuello, L. G., Functional hemichannels formed by human connexin 26 expressed in bacteria. Bioscience Rep. 2015, 35 (2), e00177.
43. Fiori, M. C.; Krishnan, S.; Kjellgren, A.; Cuello, L. G.; Altenberg, G. A., Inhibition by Commercial Aminoglycosides of Human Connexin Hemichannels Expressed in Bacteria. Molecules 2017, 22 (12), 2063.

REFERENCES—EXAMPLE 2

1. Fiori, M. C.; Krishnan, S.; Cortes, D. M.; Retamal, M. A.; Reuss, L.; Altenberg, G. A.; Cuello, L. G., Biosci. Rep. 2015, 35 (2), e00177.
2. Krishnan, S.; Fiori, M. C.; Whisenant, T. E.; Cortes, D. M.; Altenberg, G. A.; Cuello, L. G., SLAS Discov. 2017, 22 (2), 135-143.
3. Stumpe, S.; Bakker, E. P., Arch. Microbiol. 1997, 167 (2-3), 126-136.
4. Buurman, E. T.; McLaggan, D.; Naprstek, J.; Epstein, W., J. Bacteriol. 2004, 186 (13), 4238-4245.

5. Shrestha, J. P.; Baker, C.; Kawasaki, Y.; Subedi, Y. P.; de Paul, N. N. V.; Takemoto, J. Y.; Chang, C.-W. T., Eur. J. Med. Chem. 2017, 126, 696-704.
6. Zhang, Q.; Alfindee, M. N.; Shrestha, J. P.; Nziko, V. d. P. N.; Kawasaki, Y.; Peng, X.; Takemoto, J. Y.; Chang, C.-W. T. J. Org. Chem. 2016, 81, 10651-10663.

REFERENCES EXAMPLE 3

1. Fiori M C, Krishnan S, Kjellgren A, Cuello L G, Altenberg G A. Inhibition by commercial aminoglycosides of human connexin hemichannels expressed in bacteria. Molecules 22(12), 2063 (2017).
2. Zhang Q, Alfindee M N, Shrestha J P, et al. Divergent synthesis of three classes of antifungal amphiphilic kanamycin derivatives. J. Org. Chem. 81(22), 10651-10663 (2016).
3. AlFindee M N, Subedi Y P, Fiori M C, et al. Inhibition of connexin hemichannels by new amphiphilic aminoglycosides without antibiotic activity. ACS Med. Chem. Lett. 9(7), 697-701 (2018).
4. Subedi Y P, Pandey U, Alfindee M N, et al. Scalable and cost-effective tosylation-mediated synthesis of antifungal and fungal diagnostic 6"-Modified amphiphilic kanamycins. Eur. J. Med. Chem. 182, 111639 (2019).
5. Subedi Y P, Roberts P, Grilley M, Takemoto J Y, Chang C-WT. Development of fungal selective amphiphilic kanamycin: Cost-effective synthesis and use of fluorescent analogs for mode of action investigation. ACS Infect. Dis. 5(3), 473-483 (2019).
6. Subedi Y P, Kjellgren A, Roberts P, et al. Amphiphilic aminoglycosides with increased selectivity for inhibition of connexin 43 (Cx43) hemichannels. Eur. J. Med. Chem., 112602 (2020).
7. Huth M, Ricci A, Cheng A. Mechanisms of aminoglycoside ototoxicity and targets of hair cell protection. Int. J. Otolaryngol. 2011, (2011).

What is claimed is:
1. An amphiphilic molecule with a structure

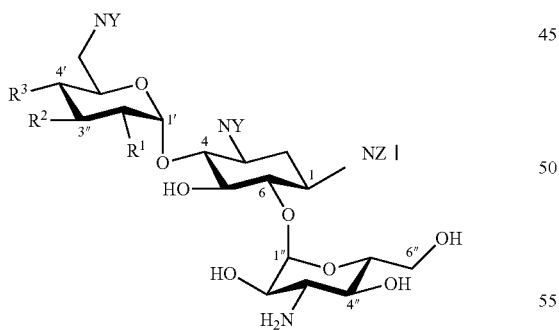

having reduced antimicrobial activity when compared to unmodified kanamycin; wherein
Y is $H_2$,
Z is $HR^4$,
$R^1$, $R^2$, $R^3$, $R^4$ are, methyl, ethyl, propyl, butyl, linear alkyl, alkylcarbonyl chains, or cyclic groups.

2. The molecule of claim 1, wherein the molecule has at least one of: substantially no antimicrobial activity, no antibacterial activity, or inhibits connexin hemichannels.

3. A molecule of formula:

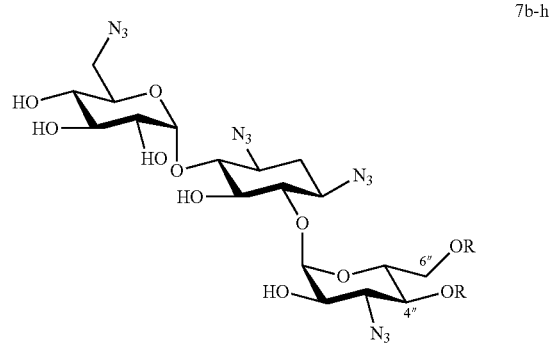

wherein R in compounds 7b to 7h is selected from at least one of:

| R | Compound |
|---|---|
| ~~CH₂-C₆H₄-OCH₃ | 7b |
| ~~CH₂-C₆H₄-CH₃ | 7c |
| ~~CH₂-C₆H₄-Cl | 7d |
| ~~CH₂-C₆H₄-F | 7e |
| ~~CH₂-(2-naphthyl) | 7f |
| ~~CH₂-(1-naphthyl) | 7g |
| ~~CH₂-(3-biphenyl) | 7h |

4. A molecule comprising the formula:
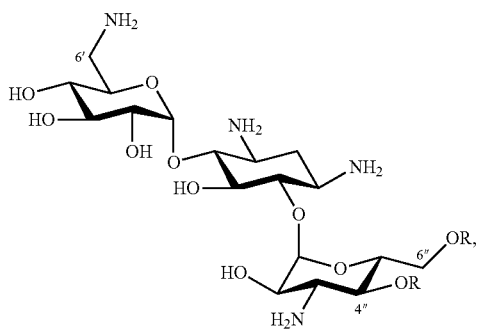
K46
wherein
| Code/compound # | R |
|---|---|
| K46B01/7 | Benzyl; |
| K46BM5/8 | Benzyl and all hydroxyl groups were methylated; |
| K46B09/10 | 4-methoxybenzyl; |
| K46B03/11 | 4-methylbenzyl; |
| K46B10/12 | 4-chlorobenzyl; |
| K46B04/13 | 4-fluorobenzyl; |
| K46B05/14 | 2-naphthylmethyl; |
| K46B11/15 | 1-naphthylmethyl; or |
| K46B07/16 | 3-biphenylmethyl. |
5. A molecule having the formula:
K30, K34, K36

-continued
K40*
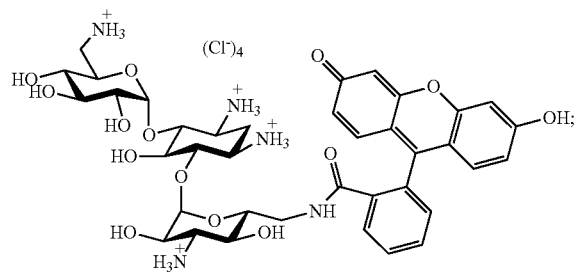
K81
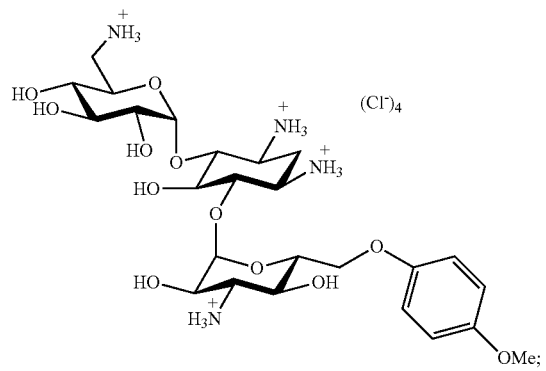
K82
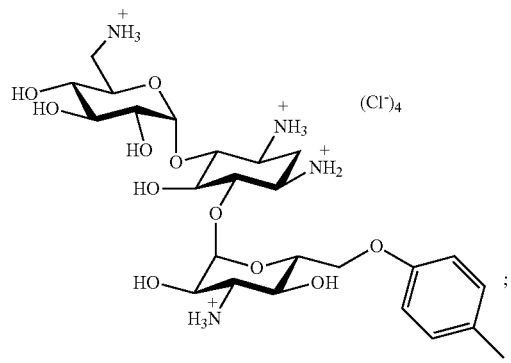
K84
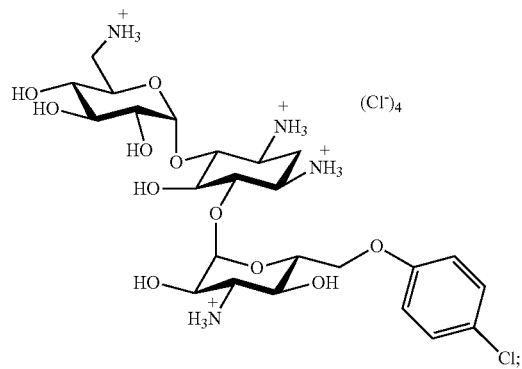
K85
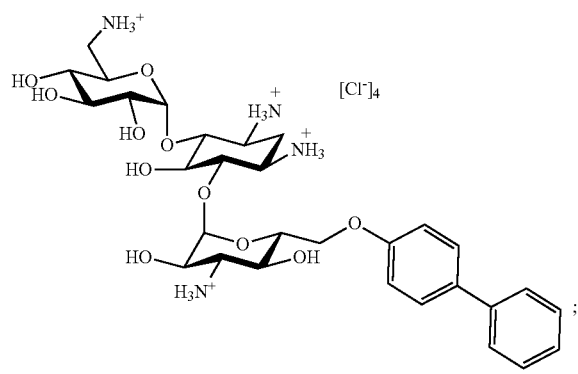

-continued
KI08
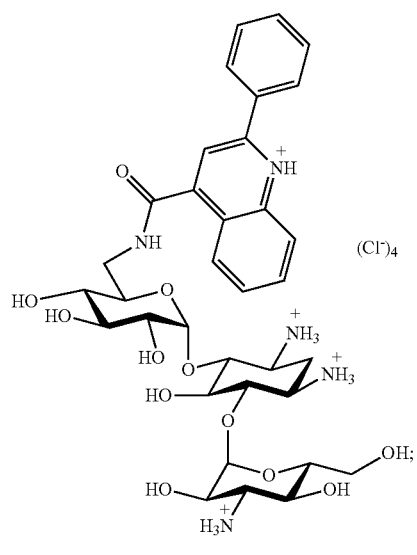
KI09
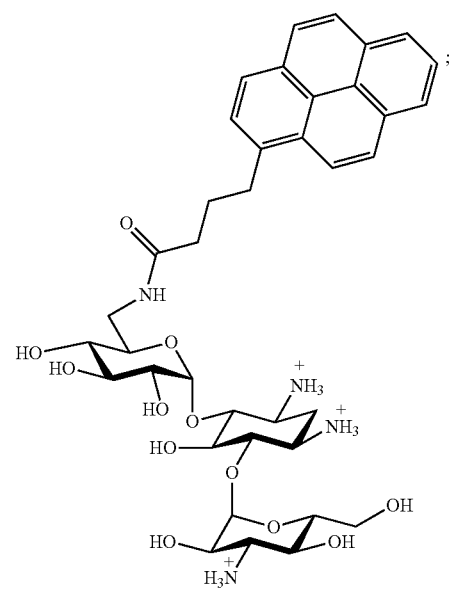
KI07
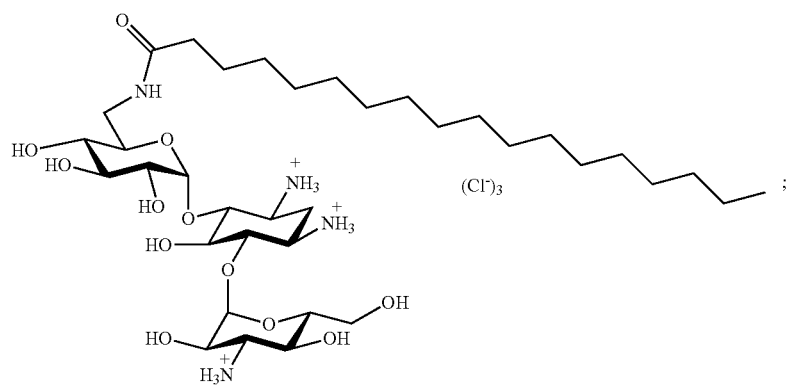
KI10
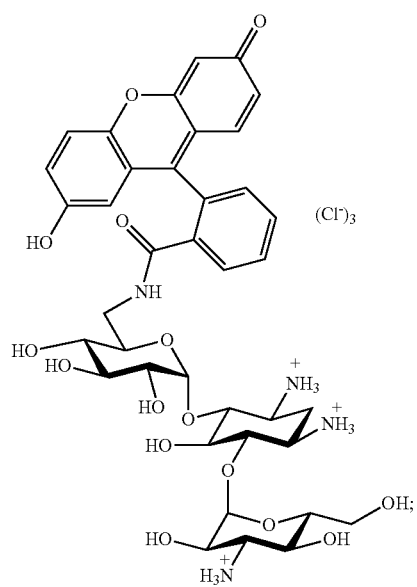
KI12 or
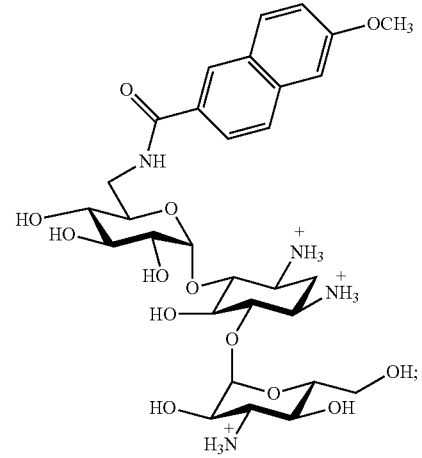

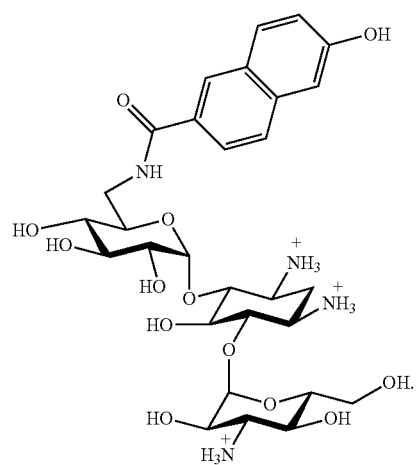
KI13
* * * * *